United States Patent
Babu et al.

(10) Patent No.: US 6,562,861 B1
(45) Date of Patent: May 13, 2003

(54) SUBSTITUTED CYCLOPENTANE AND CYCLOPENTENE COMPOUNDS USEFUL AS NEURAMINIDASE INHIBITORS

(75) Inventors: Yarlagadda S. Babu, Birmingham, AL (US); Pooran Chand, Birmingham, AL (US); John A. Montgomery, Birmingham, AL (US)

(73) Assignee: BioCryst Pharmaceuticals, Inc., Birmingham, AL (US)

(*) Notice: Subject to any disclaimer, the term of this patent is extended or adjusted under 35 U.S.C. 154(b) by 0 days.

(21) Appl. No.: 09/555,131

(22) PCT Filed: Dec. 17, 1998

(86) PCT No.: PCT/US98/26871

§ 371 (c)(1),
(2), (4) Date: May 25, 2000

(87) PCT Pub. No.: WO99/33781

PCT Pub. Date: Jul. 8, 1999

Related U.S. Application Data

(60) Provisional application No. 60/085,252, filed on May 13, 1998, and provisional application No. 60/069,956, filed on Dec. 17, 1997.

(51) Int. Cl.$^7$ ............................................. A61K 31/385
(52) U.S. Cl. ................. 514/436; 514/399; 514/563; 514/613; 514/635; 546/274.7; 546/272.7; 549/20; 562/503; 562/504; 560/122
(58) Field of Search ................. 562/503, 504; 560/122; 514/563, 613, 635, 399, 396, 436, 385; 549/14, 20, 13; 546/272.7, 274.7

(56) References Cited

U.S. PATENT DOCUMENTS

| | | | |
|---|---|---|---|
| 4,426,391 A | | 1/1984 | Alexander et al. |
| 5,739,160 A | * | 4/1998 | Mittendorf et al. |
| 5,789,434 A | | 8/1998 | Kluender et al. ............ 514/414 |

FOREIGN PATENT DOCUMENTS

| | | |
|---|---|---|
| EP | 0 130 119 A2 | 1/1985 |
| EP | 0 743 320 A2 | 11/1996 |
| JP | 49-185 | 1/1974 |
| JP | 59-163365 | 9/1984 |
| JP | 63-179835 | 7/1988 |
| JP | 05065255 | 3/1993 |
| WO | WO 92/16541 | 10/1992 |
| WO | WO 97/47194 | 12/1997 |
| WO | WO 98/34935 | 8/1998 |
| WO | WO 99/54290 | 10/1999 |
| WO | WO 99/54299 | 10/1999 |

OTHER PUBLICATIONS

Stephen C. Bergmeier et al, "Chirospecific Synthesis of (1S, 3R)–1–Amino–3–(hydroxymethyl)cyclopentane, a Precursor for Carbocyclic Nucleoside Synthesis. Intramolecular Aziridine Cyclizations" J. Org. Chem., vol. 58 (1993), pp. 5019–5022.*

Allan et al, Australian J. Chem., vol. 39, 1986 #6 pp. 855–864.*

Collect. Czech. Chem. Commun. vol. 58 (1993) pp. 2159–2179.

Kogyo Kagaku Zashi vol. 60, No. 3 (1957) pp. 355–356.

Chemical Abstracts. vol. 65 15301 c (1966).

Chemical Abstracts. vol. 62 9031 d–e (1965).

Chemical Abstracts. vol. 65 10460 c. (1966).

Chem. Pharm. Bull. 38(12) pp. 3242–3248 (1990).

Tetrahedron vol. 51, No. 37, pp. 10259–10280 (1995).

* cited by examiner

*Primary Examiner*—Jean F. Vollano
(74) *Attorney, Agent, or Firm*—Connolly Bove Lodge & Hutz LLP

(57) ABSTRACT

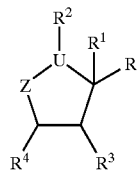

I

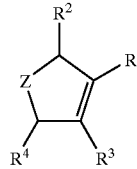

II

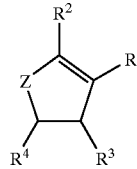

III

Compounds I–III wherein U is CH, O, or S; Z is mono- or di-substituted carbon; R is $(CH_2)_nCO_2H$, $(CH_2)_nSO_3H$, $(CH_2)_nPO_3H_2$, $(CH_2)_nNO_2$, $CH(SCH_3)_3$, esters; R1 is H, hydroxyalkyl, aminoalkyl, alkoxyalkyl; RR1 is O; n is 0–4; R2, R3 is H, hydroxyalkyl, aminoalkyl, alkoxyalkyl, haloalkyl; R4 is $(CH_2)_nOH$, $(CH_2)_nNH_2$, substituted alkyl were prepd. as neuraminidase inhibitors. Thus, (1R,3R,4R, 1'S)-(-)-(1'-acetylamino-2'-ethyl)butyl-4-(aminoimino) methylaminocyclopentan-1-carboxylic acid was prepd. and tested in vitro as neuraminidase inhibitor (IC50<1.mu.M).

41 Claims, No Drawings

SUBSTITUTED CYCLOPENTANE AND CYCLOPENTENE COMPOUNDS USEFUL AS NEURAMINIDASE INHIBITORS

CROSS-REFERENCE TO RELAYED APPLICATIONS

This application claims the.benefit under 35 USC 119 (e) of prior U.S. provisional applications Ser. No. 60/069,956, filed Dec. 17, 1997 and Ser. No. 60/085,252, filed May 13, 1998 and the U.S. national phase under 35 USC 371 of PCT/US98/26871 now abandoned.

TECHNICAL FIELD

This invention relates to novel substituted cyclopentane and cyclopentene compounds and derivatives thereof useful as neuraminidase inhibitors, to pharmaceutical compositions containing said compounds useful for the prevention, treatment or amelioration of viral, bacterial and other infections, and to methods of using said compounds. The present invention is also concerned with novel intermediates or precursors for producing the novel substituted cyclopentane and cyclopentene compounds of the present invention.

BACKGROUND OF THE INVENTION

Despite the wealth of information available, influenza remains a potentially devastating disease of man, lower mammals, and birds. No effective vaccine exists and no cure is available once the infection has been initiated.

Influenza viruses consist of eight pieces of single stranded RNA, packaged in orderly fashion within the virion. Each piece codes for one of the major viral proteins. The replication complex is enclosed with a membrane composed of matrix protein associated with a lipid bilayer. Embedded in the lipid bilayer are two surface glycoprotein spikes, hemagglutinin (HA) and the enzyme neuraminidase (NA). All the viral genes have been cloned and the three dimensional structures of the surface glycoproteins have been determined.

Influenza viruses continually undergo antigenic variation in the two surface antigens, HA and NA, toward which neutralizing antibodies are directed. For this reason, vaccines and a subject's natural immune system have not been very effective. Attention is now being directed to finding other potential antiviral agents acting at others sites of the virion. This invention is directed to novel compounds which are useful in inhibiting the viral surface enzyme NA.

Furthermore, many other organisms carry also NA. Many of these NA-possessing, organisms are also major pathogens of man and/or mammals, including *Vibraeo Cholerae, Clostridium perfringes, Streptococcus pneumonia, Arthrobacter sialophilas*, and other viruses, such as parainfluenza virus, mumps virus, newcastle disease virus, fowl plague virus, and Sendai virus. Compounds of this invention are also directed to inhibiting NA of these organisms.

In viruses, NA exists as a tetramer made of four roughly spherical subunits and a centrally-attached stalk containing a hydrophobic region by which it is embedded in the organism's membrane. Several roles have been suggested for NA. The enzyme catalyzes cleavage of the α-Ketosidic linkage between terminal sialic acid and the adjacent sugar residue. Removal of the sialic acid lowers the viscosity and permits access of the virus to the epithelial cells. NA also destroys the HA receptor on the host cell, thus allowing elution of progeny virus particles from infected cells.

Research indicates that the active site for influenza neuraminidase remains substantially unchanged for the major strains of influenza. For example, a comparison of sequences from influenza A subtypes and influenza B shows conserved residues with crucial structures and functional roles. Even though the sequence homology is only about 30%, many of the catalytic residues are conserved. Furthermore, the three-dimensional structures of influenza A and B neuraminidases have been determined. Superposition of the various structures shows remarkable structural similarity of the active site. Since the active site amino acid residues are conserved in all known influenza A neuraminidases that have been sequenced so far, an inhibitor that is effective against different strains of influenza A and/or B neuraminidase can be designed based on the three dimensional structure of neuraminidase.

In general, the role of NA is thought to be for the mobility of the virus both to and from the site of infections. Compounds that inhibit neuraminidase's activity may protect a subject from infection and/or cure a subject once infection has set in. It is a further object of this invention to provide a method of using compounds of this invention for treating and/or curing a viral infection.

Analogues of neuraminic acid, such as 2-deoxy-2,3-didehydro-N-acetylneuraminic acid (DANA) and its derivatives are known to inhibit HA in vitro; however, these compounds are inactive in vivo. Palese and Schulman, IN CHEMOPROPHYLAXIX AND VIRUS INFECTIONS OF THE UPPER RESPIRATORY TRACT, Vol. 1 (J. S. Oxford, Ed.), CRC Press, 1977, at PS 189–205.

Von Itzstein et al. describes cyclohexane analogs of -D-neuraminic acid of the formula (a)

and (b)

Wherein:
  A is O, C or S in formula (a), and N or C in formula (b);
  $R^1$ is $CO_2H$, $PO_3H_2$, $NO_2$, $SO_2H$, $SO_3H$, tetrazolyl-, $CH_2CHO$, CHO, or $CH(CHO)_2$;
  $R^2$ is H, $OR^6$, F, Cl, Br, CN, $NHR^6$, $SR^6$ or $CH_2X$, where X is $NHR^6$ halogen or $OR^6$;
  $R^3$ and $R^{3'}$ are H, CN, $NHR^6$, $SR^6$, $=NOR^6$, $OR^6$, guanidino, $NR^6$;

$R^4$ is $NHR^6$, $SR^6$, $OR^6$, $CO_2R^6$, $NO_2$, $C(R^6)_3$, $CH_2CO_2R^6$, $CH_2NO_2$ or $CH_2NHR^6$;

$R^5$ is $CH_2YR^6$, $CHYR^6CH_2YR^6$ or $CHYR^6CHYR^6CH_2YR^6$;

$R^6$ is H, acyl, alkyl, allyl, or aryl;

Y is O, S, NH, or H;

and pharmaceutical salts thereof, useful as antiviral agents.

In addition, certain benzene derivatives are suggested in U.S. Pat. No. 5,453,533 as being inhibitors of influenza virus neuraminidase and various others are disclosed in U.S. Pat. No. 5,602,277. Yamamoto et al. describe various sialic acid isomers as having inhibitory activity against neuraminidase in Synthesis of Sialic Acid Isomers With Inhibitory Activity Against Neuraminidase, Tertrahedron Letters, Vol. 33, No. 39, pp. 5791–5794, 1992.

WO 96/26933 to Gilead sciences, Inc. describes certain 6-membered ring compounds as possible inhibitors of neuraminidase.

However, none of these references disclose the cyclopentane and cyclopentene derivatives of the present invention.

SUMMARY OF INVENTION

An aspect of the present invention is directed to compounds represented by the formulae:

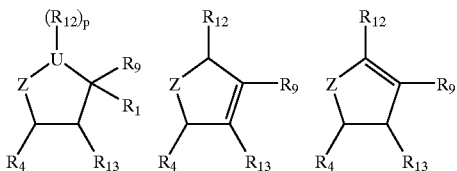

wherein

U is CH, O, or S;

Z is $-C(R_2)(R_3)$, $-CH-N(R_2)(R_3)$, $C(R_3)[(CH_2)nR_2]$, $CH-C(R_3)(R_8)(CH_2)nR_2$, $C[(CH_2)nR_2]-[CH(R_3)(R_8)]$, $C[(R_3)][CH[(CH_2)nR_2](R_8)]$;

$R_1$ is H, $(CH_2)nOH$, $(CH_2)nNH_2$, $(CH_2)nNR_{10}R_{11}$, $(CH_2)nOR_{11}$, $(CH_2)nSR_{11}$, or $(CH_2)n$ halogen $R_9$ is $(CH_2)nCO_2H$, $(CH_2)nSO_3H$, $(CH_2)nPO_3H_2$, $(CH_2)nNO_2$, $CH(SCH_3)_3$, esters thereof, or salts thereof; or $R_1 R_9$ together represent

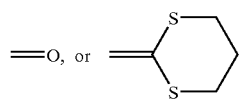

$R_2$ is H, $NHC(O)R_5$, $NHC(S)R_5$, $NHSO_2R_5$, $C(O)NHR_5$, $SO_2NHR_5$, $CH_2S(O)R_5$, or $CH_2SO_2R_5$ $R_3$ and $R_8$ individually is H, $(CH_2)nC(O)R_{10}$, $(CH_2)nCO_2R_{10}$, $(CH_2)mOR_{10}$, $CH(OR_{10})CH(R_{10})m$, $C(O)N(R_{10})m$, $C(O)N(OR_{10})R_{10}$, $(CH_2)nN(R_{10})m$, $CH(R_{10})m$, $(CH_2)n(R_{10})m$, $CH_2CH(OR_{10})CH_2OR_{10}$, $CH(OR_{10})CH(OR_{10})CH_2OR_{10}$, $CH_2OR_{10}$, $CH(OR_{10})CH_2NHR_{10}$, $CH_2CH(OR_{10})CH_2NHR_{10}$, $CH(OR_{10})CH(OR_{10})CH_2NHR_{10}$, $C(=NR_{10})N(R_{10})m$, $NHR_{10}$, $NHC(=NR_{10})N(R_{10})m$, $(CH_2)m-X-W-Y$, $CH_2CH(X-W-Y)CH_2OR_{10}$, $CH(X-W-Y)CH(OR_{10})CH_2OR_{10}$, $CH(X-W-Y)CH_2(OR_{10})$, $CH(OR_{10})CH(X-W-Y)CH_2OR_{10}$, $CH(OR_{10})CH_2(X-W-Y)$, $CH_2CH(X-W-Y)CH_2NHR_{10}$, $CH(X-W-Y)CH_2$ $CH(OR_{10})CH_2NHR_{10}$, $CH(X-W-Y)CH_2$ $(NHR_{10})$, $CH(OR_{10})CH(X-W-Y)CH_2NHR_{10}$, or $CH(NHR_{10})CH_2(X-W-Y)$;

provided that at least one of $R_2$, $R_3$, and $R_8$ is other than H;

$R_4$ is H, $(CH_2)nOH$, $(CH_2)nOR_{11}$, $(CH_2)nOC(O)R_{11}$, $(CH_2)nNHC(NR_{11})NHR_{11}$, $(CH_2)nNR_{10}R_{11}$, $(CH_2)nNH_2$, $(CH_2)nC(=NH)(NH_2)$, $(CH_2)nNHC(=NR_{11})NH_2$, $(CH_2)nNHC(=NR_7)NH_2$, $(CH_2)nCN$, $(CH_2)nN_3$, $C(=NH)NH_2$, $C(NR_7)NH_2$, or $C(NR_{11})NH_2$;

$R_5$ is H, lower alkyl, cyclo alkyl, halogen substituted alkyl, aryl, substituted aryl, or $CF_3$;

$R_7$ is H, $(CH_2)nOH$, $(CH_2)nCN$, $(CH_2)nNH_2$, or $(CH_2)nNO_2$;

$R_{10}$ is H, lower alkyl, lower alkylene, branched alkyl, cyclic alkyl, $(CH_2)n$ aromatic, $(CH_2)n$ substituted aromatic, or when m is 2 both $R_{10}$ groups can also be interconnected to form an N substituted heterocyclic ring, or other 5 or 6 membered heterocyclic ring;

$R_{11}$ is lower alkyl, branched alkyl, $(CH_2)m$ aromatic, $SO_2R_{10}$, $C(O)R_{10}$, or $C(O)OR_{10}$;

$R_{12}$ and $R_{13}$ is H, $(CH_2)nOH$, $(CH_2)nNH_2$, $(CH_2)nNR_{10}R_{11}$, $(CH_2)nOR_{11}$, $(CH_2)nF$, $(CH_2)nOC(O)R_{11}$, $(CH_2)nNHC(O)R_{11}$, or $X-W-Y$;

m is 1 or 2;

n is 0–4;

p is 0 or 1;

X is O, S, $CH_2$, or NH;

W is a spacer group made up of a chain of 1 to 100 atoms, and optionally also comprising of substituted carbon and/or nitrogen atoms and optionally including oxygen or sulphur atoms; and Y is H, OH, SH, $NH_2$, $CH=O$, $CH=CH_2$, $CO_2H$, $CONHNH_2$, or a protected form of one of these end functionalities;

and pharmaceutically acceptable salts thereof.

The present invention is also concerned with compositions for inhibiting influenza virus neuraminidase comprising a pharmaceutically acceptable carrier and an amount effective for inhibiting influenza virus nueraminidase of a compound as defined above.

A further aspect of the present invention involves a method for inhibiting influenza virus that comprises administering to a patient in need thereof a compound as defined above in a amount effective for inhibiting influenza virus nueraminidase.

A still further aspect of the present invention is concerned with treating influenza virus infection comprising administering to a patient in need thereof a compound as defined above in an amount effective for inhibiting influenza virus nueramindase.

Another aspect of the present invention relates to intermediates represented by the following formulae:

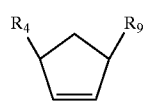

Wherein $R_4$ and $R_9$ are the same defined above; and

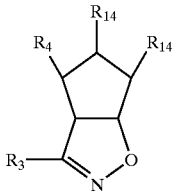

Wherein $R_{14}$ individually is H, O, $(CH_2)nCO_2H$, $(CH_2)nSO_3H$, $(CH_2)nPO_3H_2$, $(CH_2)nNO_2$, $CH(SCH_3)_3$,

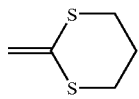

esters thereof or salts thereof and provided at least one of $R_{14}$ is H, and $R_3$ and $R_4$ are as defined above.

BEST AND VARIOUS MODES FOR CARRYING OUT INVENTION

An aspect of the present invention is directed to compounds represented by the formulae:

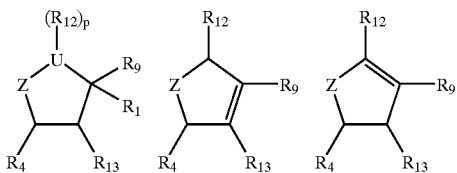

wherein
U is CH, O, or S;
Z is $—C(R_2)(R_3)$, $—CH—N(R_2)(R_3)$, $C(R_3)[(CH_2)nR_2]$, $CH—C(R_3)(R_8)(CH_2)nR_2$, $C[(CH_2)nR_2]—[CH(R_3)(R_8)]$, $C[(R_3)][CH[(CH_2)nR_2](R_8)]$;
$R_1$ is H, $(CH_2)nOH$, $(CH_2)nNH_2$, $(CH_2)nNR_{10}R_{11}$, $(CH_2)nOR_{11}$, $(CH_2)nSR_{11}$, or $(CH_2)n$ halogen
$R_9$ is $(CH_2)nCO_2H$, $(CH_2)nSO_3H$, $(CH_2)nPO_3H_2$, $(CH_2)nNO_2$, $CH(SCH_3)_3$, esters thereof, or salts thereof;
or $R_1$ $R_9$ together represent

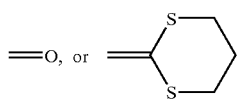

$R_2$ is H, $NHC(O)R_5$, $NHC(S)R_5$, $NHSO_2R_5$, $C(O)NHR_5$, $SO_2NHR_5$, $CH_2S(O)R_5$, or $CH_2SO_2R_5$
$R_3$ and $R_8$ individually is H, $(CH_2)nC(O)R_{10}$, $(CH_2)nCO_2R_{10}$, $(CH_2)mOR_{10}$, $CH(OR_{10})CH(R_{10})m$, $C(O)N(R_{10})m$, $C(O)N(OR_{10})R_{10}$, $(CH_2)nN(R_{10})m$, $CH(R_{10})m$, $(CH_2)n(R_{10})m$, $CH_2CH(OR_{10})CH_2OR_{10}$, $CH(OR_{10})CH(OR_{10})CH_2OR_{10}$, $CH_2OR_{10}$, $CH(OR_{10})CH_2NHR_{10}$, $CH_2CH(OR_{10})CH_2NHR_{10}$, $CH(OR_{10})CH(OR_{10})CH_2NHR_{10}$, $C(=NR_{10})N(R_{10})m$, $NHR_{10}$, $NHC(=NR_{10})N(R_{10})m$, $(CH_2)m—X—W—Y$, $CH_2CH(X—W—Y)CH_2OR_{10}$, $CH(X—W—Y)CH(OR_{10})CH_2OR_{10}$, $CH(X—W—Y)CH_2(OR_{10})$, $CH(OR_{10})CH(X—W—Y)CH_2OR_{10}$, $CH(OR_{10})CH_2(X—W—Y)$, $CH_2CH(X—W—Y)CH_2NHR_{10}$, $CH(X—W—Y)$ $CH(OR_{10})CH_2NHR_{10}$, $CH(X—W—Y)CH_2(NHR_{10})$, $CH(OR_{10})CH(X—W—Y)CH_2NHR_{10}$, or $CH(NHR_{10})CH_2(X—W—Y)$;

provided that at least one of $R_2$, $R_3$, and $R_8$ is other than H;

$R_4$ is H, $(CH_2)nOH$, $(CH_2)nOR_{11}$, $(CH_2)nOC(O)R_{11}$, $(CH_2)nNHC(NR_{11})NHR_{11}$, $(CH_2)nNR_{10}R_{11}$, $(CH_2)nNH_2$, $(CH_2)nC(=NH)(NH_2)$, $(CH_2)nNHC(=NR_{11})NH_2$, $(CH_2)nNHC(=NR_7)NH_2$, $(CH_2)nCN$, $(CH_2)nN_3$, $C(=NH)NH_2$, $C(NR_7)NH_2$, or $C(NR_{11})NH_2$;

$R_5$ is H, lower alkyl, cyclo alkyl, halogen substituted alkyl, aryl, substituted aryl, or $CF_3$;

$R_7$ is H, $(CH_2)nOH$, $(CH_2)nCN$, $(CH_2)nNH_2$, or $(CH_2)nNO_2$;

$R_{10}$ is H, lower alkyl, lower alkylene, branched alkyl, cyclic alkyl, $(CH_2)n$ aromatic, $(CH_2)n$ substituted aromatic, or when m is 2 both $R_{10}$ groups can also be interconnected to form an N substituted heterocyclic ring, or other 5 or 6 membered heterocyclic ring;

$R_{11}$ is lower alkyl, branched alkyl, $(CH_2)m$ aromatic, $SO_2R_{10}$, $C(O)R_{10}$, or $C(O)OR_{10}$;

$R_{12}$ and $R_{13}$ is H, $(CH_2)nOH$, $(CH_2)nNH_2$, $(CH_2)nNR_{10}R_{11}$, $(CH_2)nOR_{11}$, $(CH_2)nF$, $(CH_2)nOC(O)R_{11}$, $(CH_2)nNHC(O)R_{11}$, or $X—W—Y$;

m is 1 or 2;
n is 0–4;
p is 0 or 1;
X is O, S, $CH_2$, or NH;
W is a spacer group made up of a chain of 1 to 100 atoms, and optionally also comprising of substituted carbon and/or nitrogen atoms and optionally including oxygen or sulphur atoms; and
Y is H, OH, SH, $NH_2$, $CH=O$, $CH=CH_2$, $CO_2H$, $CONHNH_2$, or a protected form of one of these end functionalities;
and pharmaceutically aceptable salts thereof.

The present invention also relates to intermediates represented by the following formulae:

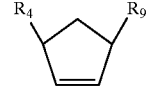

wherein $R_4$ and $R_9$ are the same defined above; and

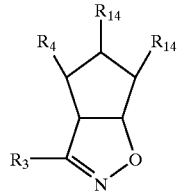

wherein $R_{14}$ individually is H, O, $(CH_2)nCO_2H$, $(CH_2)nSO_3H$, $(CH_2)nPO_3H_2$, $(CH_2)nNO_2$, $CH(SCH_3)_3$,

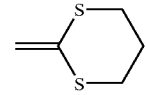

esters thereof or salts thereof and provided at least one of $R_{14}$ is H, and $R_3$ and $R_4$ are as defined above.

The lower alkyl groups contain 1 to about 8 carbon, and preferably 1 to about 3 carbon atoms, and can be straight, branched-chain or cyclic saturated aliphatic hydrocarbon groups.

Examples of suitable alkyl groups include methyl, ethyl, and propyl. Examples of branched alkyl groups include isopropyl and t-butyl. Examples of suitable cyclic aliphatic groups typically contain 3–8 carbon atoms and include cyclopentyl and cyclohexyl. The aromatic or aryl groups are preferably phenyl or alkyl substituted aromatic groups (aralkyl) such as phenyl $C_{1-3}$ alkyl such as benzyl, or halo substituted aryl groups.

Examples of substituted cycloalkyl groups include cyclic aliphatic groups typically containing 3–8 carbon atoms in the ring substituted with alkyl groups typically having 1–6 carbon atoms and/or hydroxy group. Usually 1 or 2 substituted groups are present.

The esters are typically lower alkyl esters having 1 to about 12 carbon atoms and preferably 1 to about 3 carbon atoms and aryl esters containing 6 to 14 carbon atoms. The alkyl esters can be straight-chain, branched-chain or cyclic saturated aliphatic hydrocarbons.

Examples of some alkyl esters are methyl, ethyl, propyl, isopropyl, t-butyl, cyclopentyl and cyclohexyl esters. The aryl esters are preferably phenyl or alkyl substituted aromatic esters (alkaryl) including $C_{1-3}$ alkyl substituted phenyl such as benzyl.

The lower alkylene group can be straight, branched chain or cyclic unsaturated hydrocarbon group and contains 2–8 carbon atoms and preferably 2–3 carbon atoms. Examples of alkylene groups are vinyl, 1-propenyl, allyl, isopropenyl, 2-methyl-2-propenyl and cyclopentenyl.

The N-heterocyclic rings contain 3–7 atoms in the ring. The heterocyclic rings can be substituted such as with a lower alkyl group. Examples of suitable heterocyclic groups are pyrrolidino, azetidino, piperidino, 3,4-didehydropiperidino, 2-methylpiperidino and 2-ethylpiperidino.

Suitable spacer groups W include, but are not limited to, linear peptides, oligosaccharides, polyols, polyethylene glycol groups, hydrocarbon groups and hydrocarbon groups linked together with oxygen or sulphur atoms, or with carbonyl, amido, urea or hydrazide functionalities. Spacer groups W may also comprise combinations of these various groups. The spacer groups can be straight or branched chain.

Suitable protecting groups for functionality Y include, but are not limited to, esters of the OH, SH, $CO_2H$ groups, carbamates of $NH_2$ and $CONHNH_2$ groups, and acetals of the CH=O group.

As used herein, the term "hydrocarbon group" includes saturated and unsaturated straight or branched hydrocarbon groups, including aryl groups, and combinations of such groups.

Pharmaceutically acceptable salts of the compounds of formula (I) include those derived from pharmaceutically acceptable, inorganic and organic acids and bases. Examples of suitable acids include hydrochloric, hydrobromic, sulfuric, nitric, perchloric, fumaric, maleic, phosphoric, glycollic, lactic, salicylic, succinic, toluene-p-sulphonic, tartaric, acetic, citric, methanesulphonic, formic, benzoic, malonic, naphthalene-2-sulphonic, trifluoroacetic and benzenesulphonic acids.

Salts derived from appropriate bases include alkali such as sodium and ammonia.

It is of course understood that the compounds of the present invention relate to all optical isomers and stereoisomers at the various possible atoms of the molecule.

Examples of some particular formulae within the scope of this invention are represented by the following:

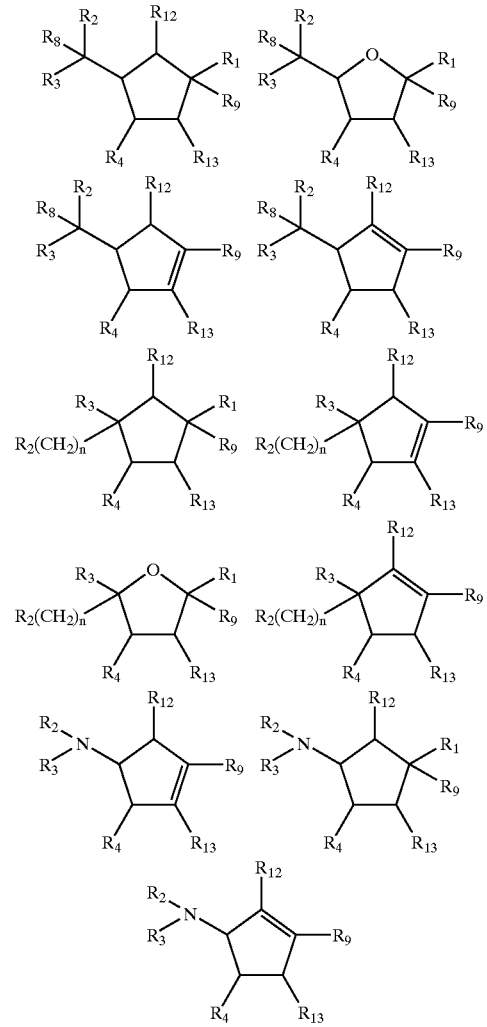

The naming system which has been used herein for the compounds of the following type is as follows:

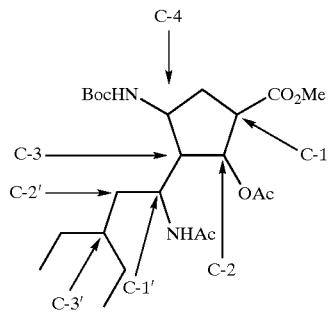

In some cases α and β have been used to show that these groups are trans to each other. These are the cases when we have more than two substituents on cyclopentane ring and only two are fixed.

In fused cyclopent[d]isoxazole system, the numbering is as follows:

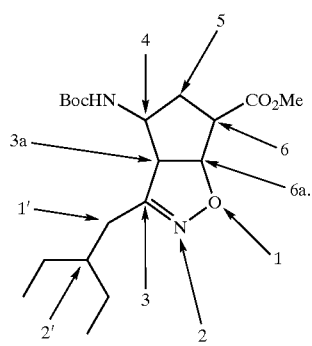
Examples of some specific compounds and intermediates according to the present application are identified in Examples 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208 and 209.
The following schemes illustrate methods for preparing compounds of the present invention.
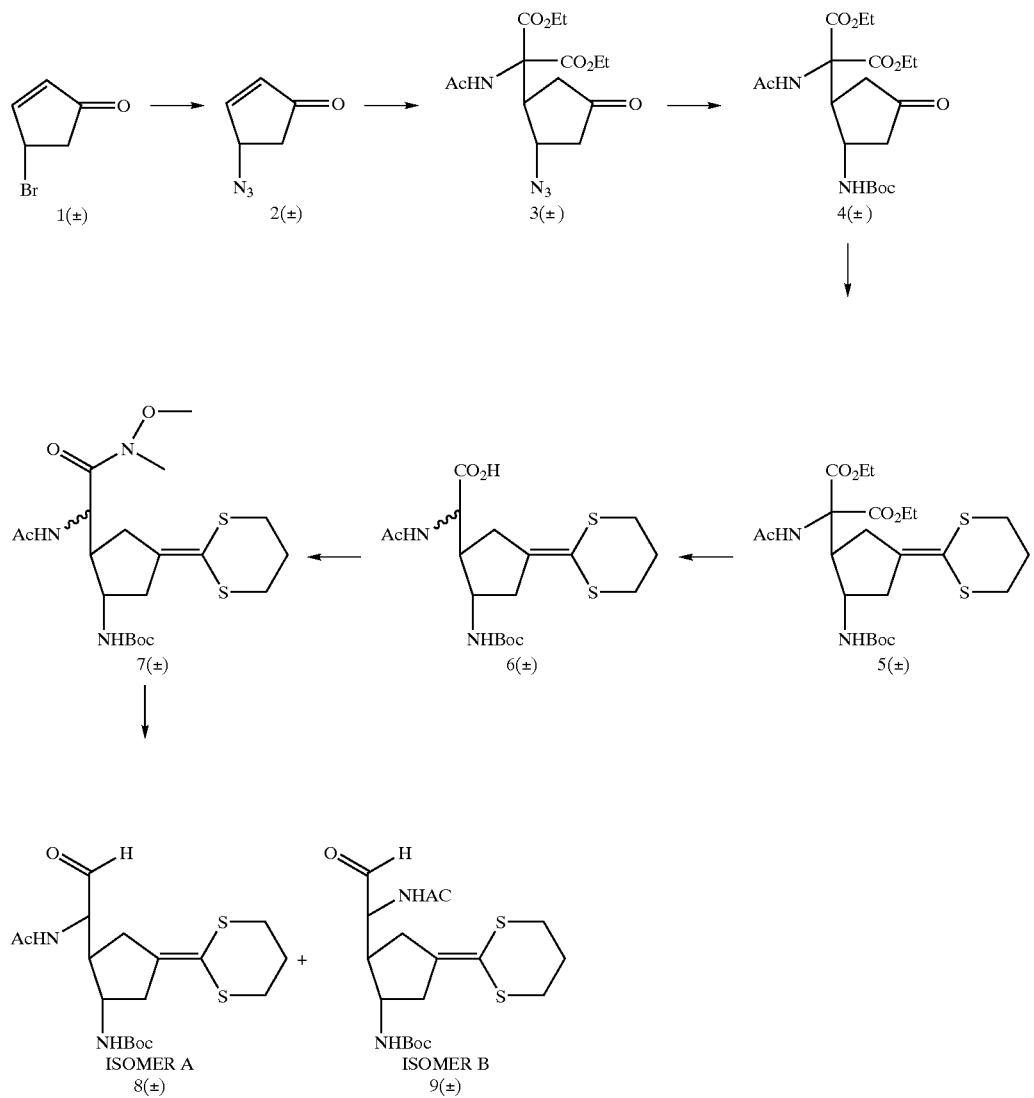
SCHEME 1

SCHEME 2
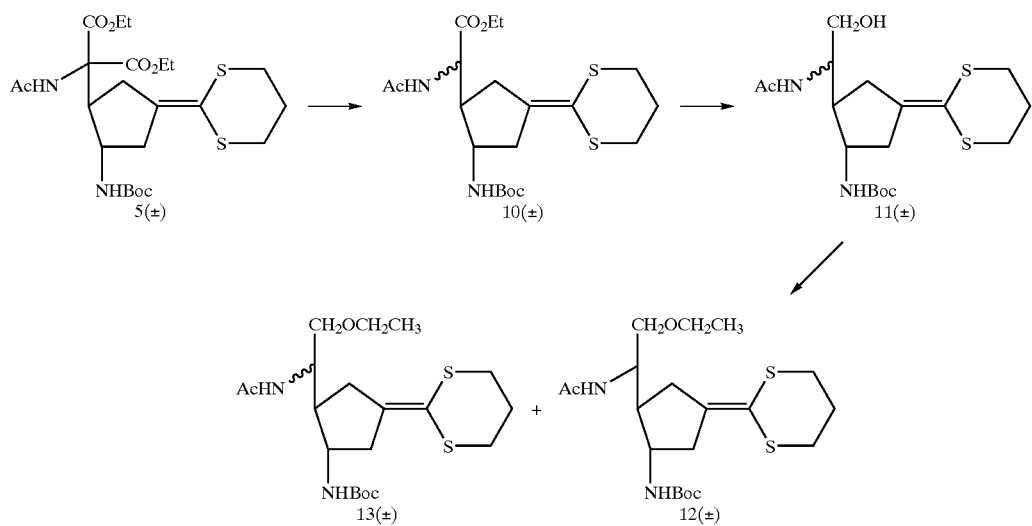
SCHEME 3
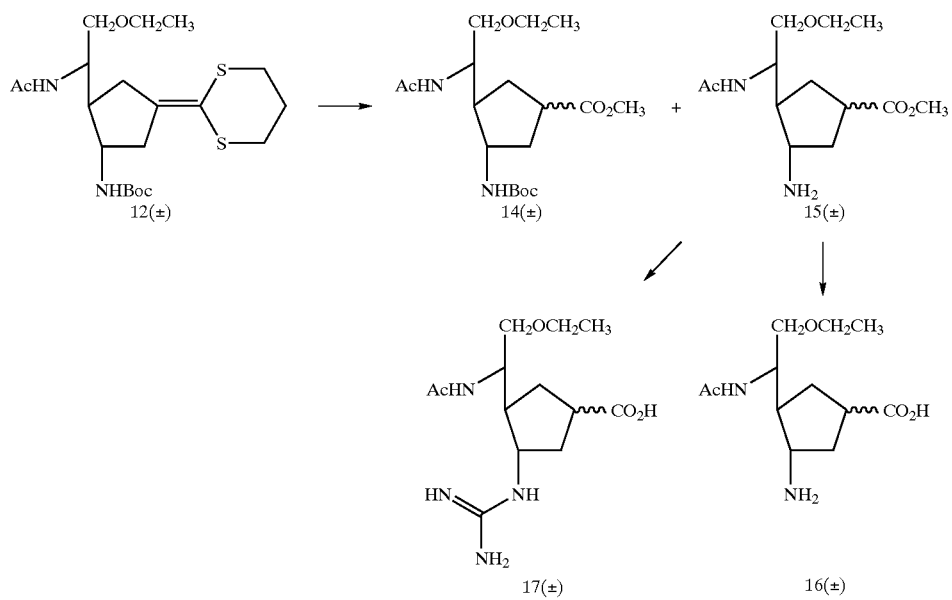
SCHEME 4
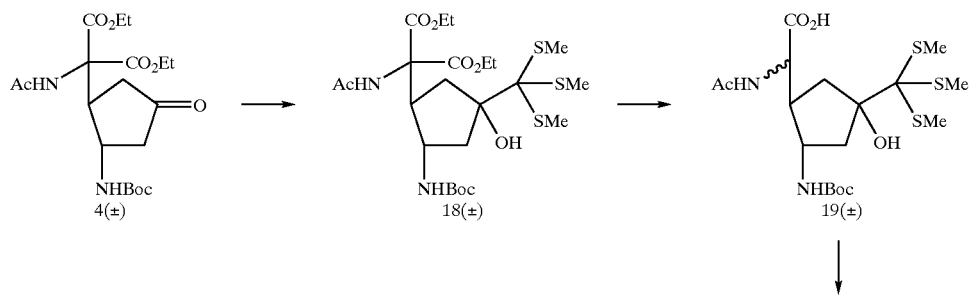

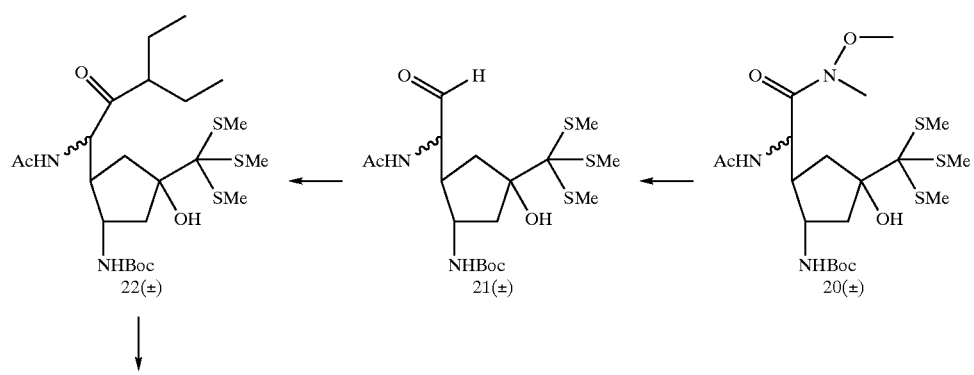
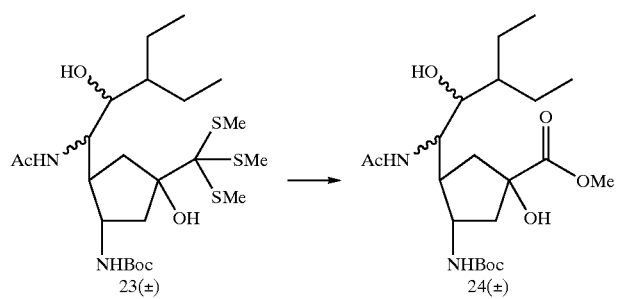
SCHEME 5
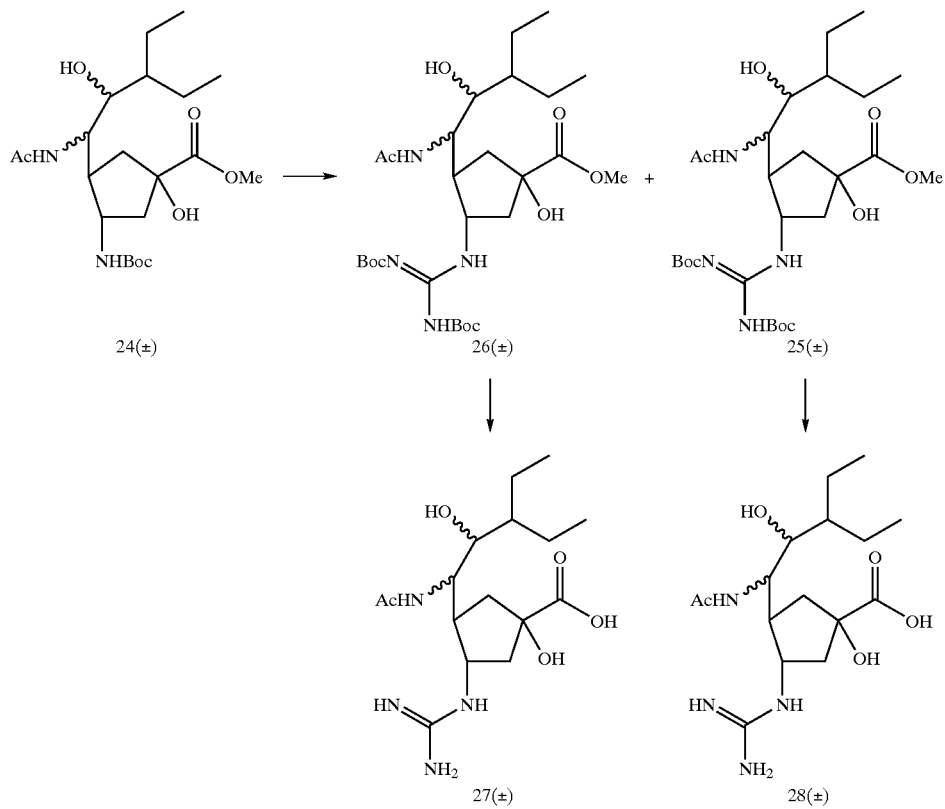

SCHEME 6
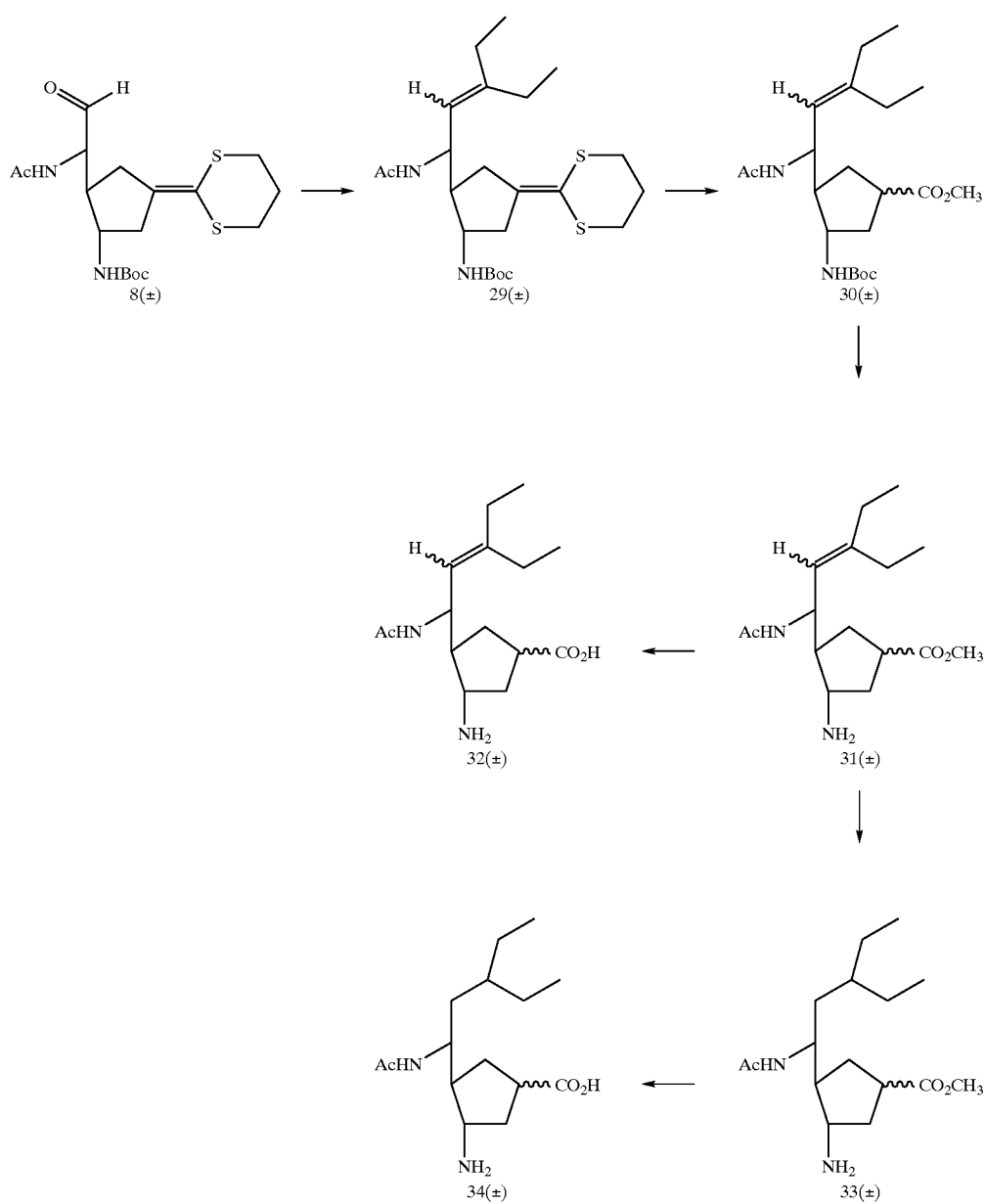
SCHEME 7
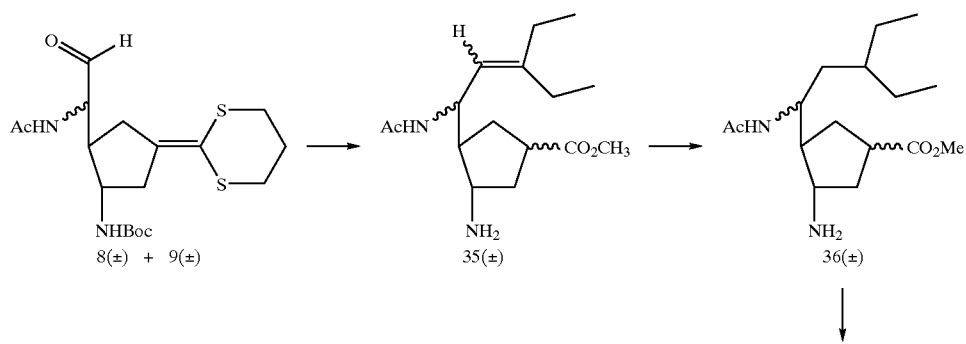

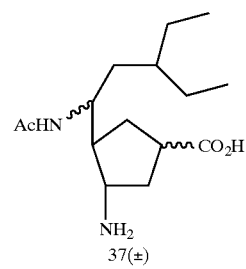
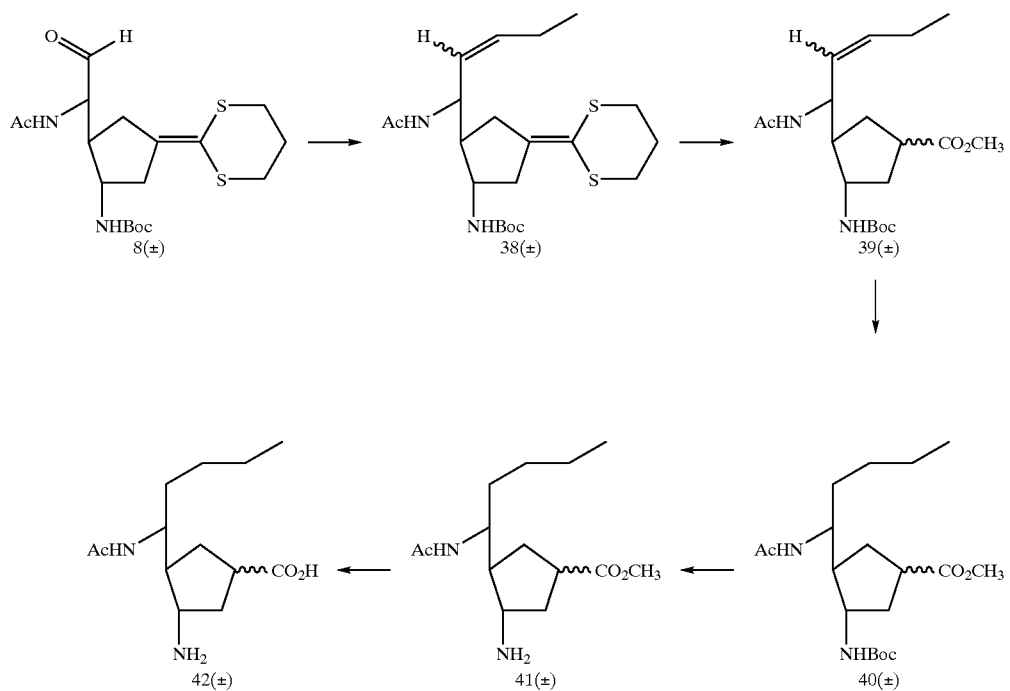
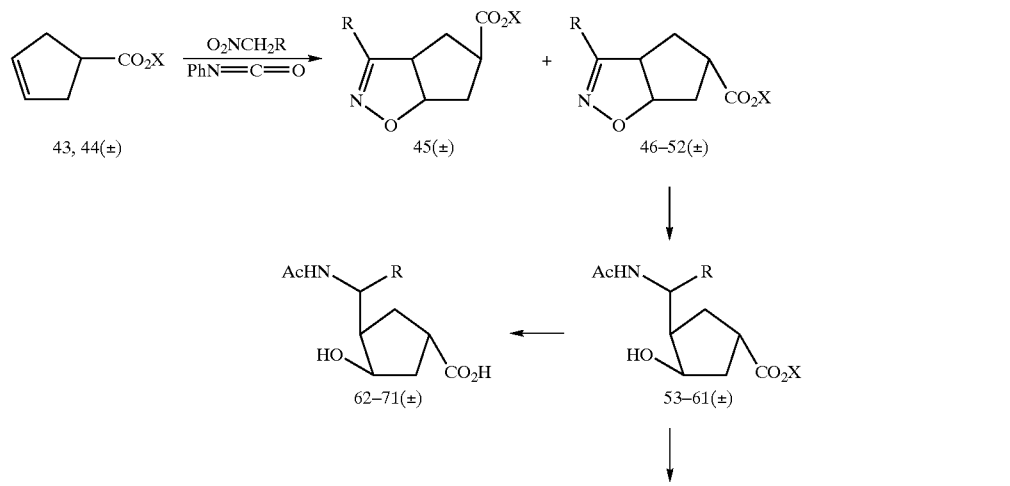

-continued
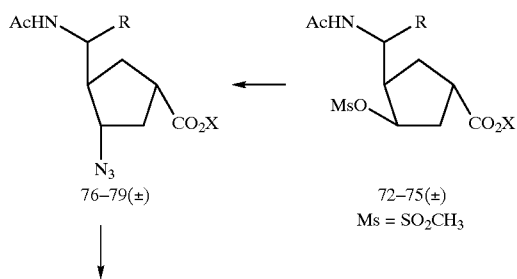
76–79(±)    72–75(±)
            Ms = SO$_2$CH$_3$
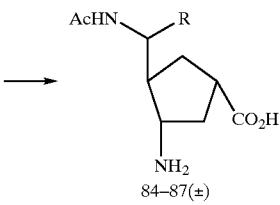
80–83(±)    84–87(±)
45, 46, 53, 54, 62–64, 72, 73, 76, 77, 80, 81, 84, 85 R = (pentyl chain)
47, 55, 56, 65, 66, 74, 78, 82, 86 R = (3-ethylpentyl chain)
48, 57, 67, 75, 79, 83, 87 R = (branched alkyl chain)
49, 58, 68 R = (cyclohexylmethyl)
50, 59, 69 R = (branched alkyl with butyl)
51, 60, 70 R = (methyl branched)
52, 61, 71 R = (cyclohexyl)
53, 55, 62, 65, 72, 76, 80, 84: isomer A at C-1′
54, 56–61, 64, 66–71, 73–75, 77–79, 81–83, 85–87: isomer B at C-1′
63: mixture of isomers A and B at C-1′
44, 49, 50, 51, 52, 58, 59, 60, 61
X = CH$_3$ in compounds:
43, 45, 46, 47, 48, 53, 54, 55, 56, 57, 72,
73, 74, 75, 76, 77, 78, 79, 80, 81, 82, 83
X = C$_2$H$_5$ in compounds:
44, 49, 50, 51, 52, 58, 59, 60, 61
Scheme 10
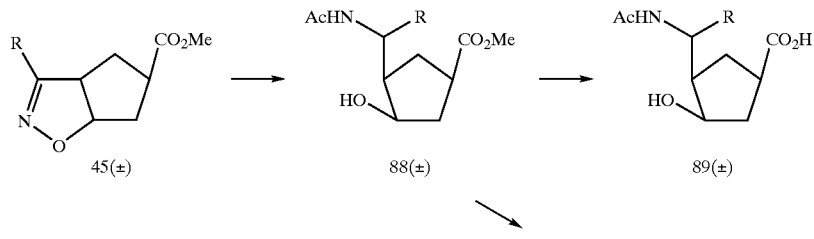
45(±)    88(±)    89(±)

-continued
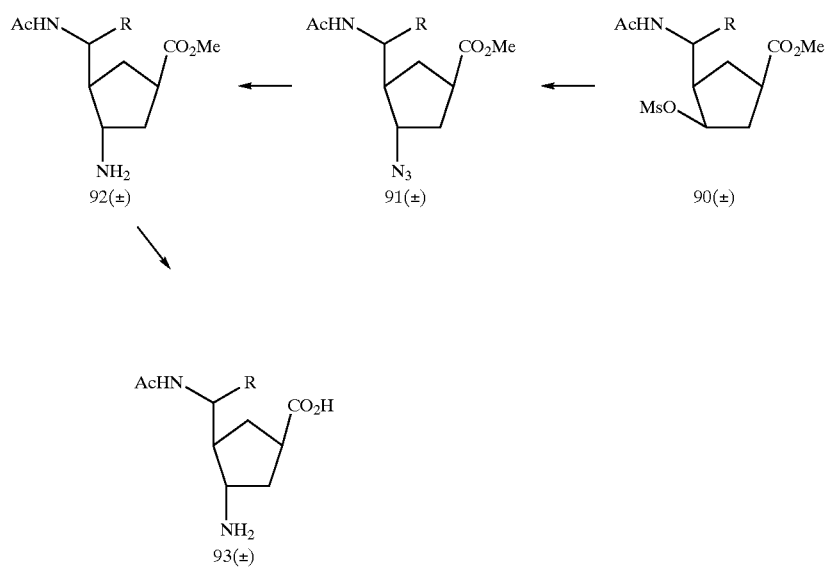
88–93: isomer B at C-1'
Scheme 11
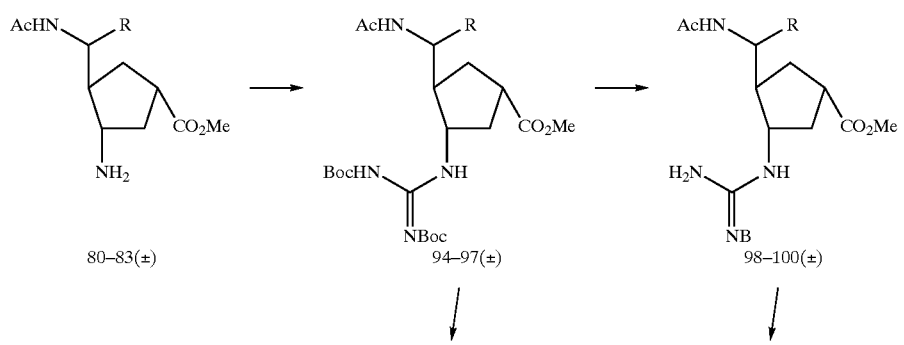
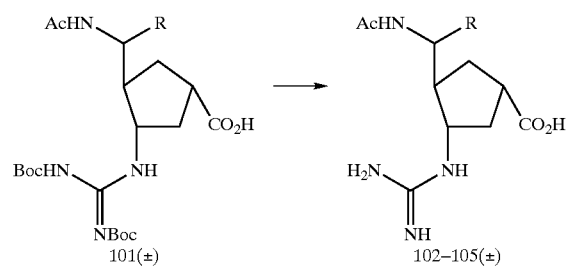

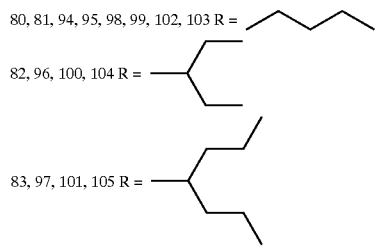
80, 94, 98, 102: isomer A at C-1'
81–83, 96, 97, 99–101, 103–105: isomer B at C-1'
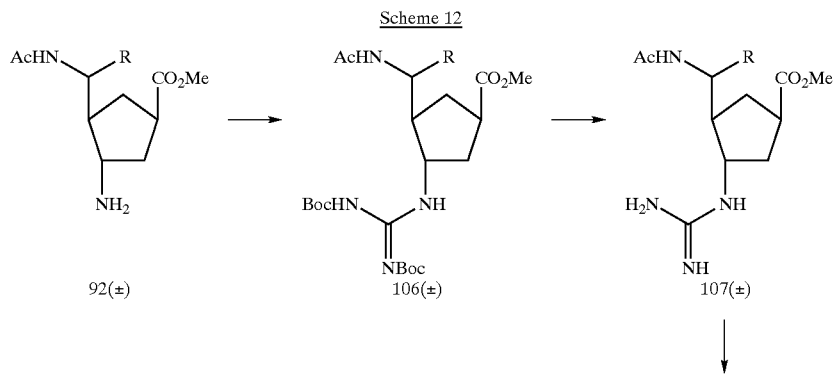
Scheme 12
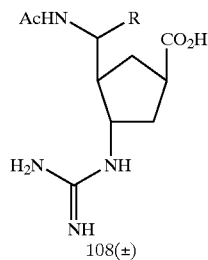
R = 
92, 106–108: isomer B at C-1'
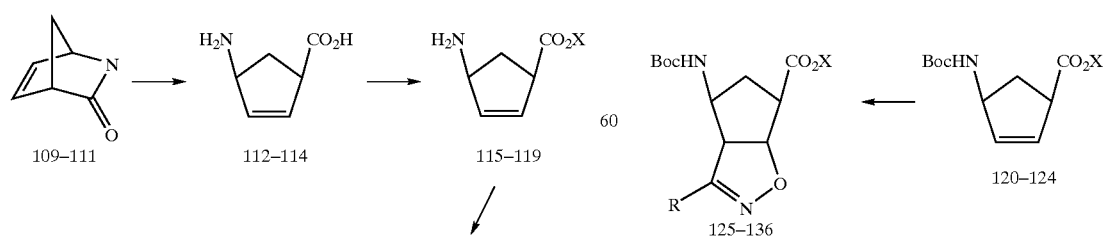
Scheme 13

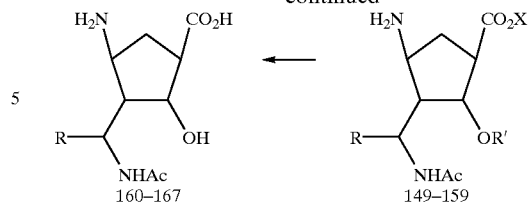
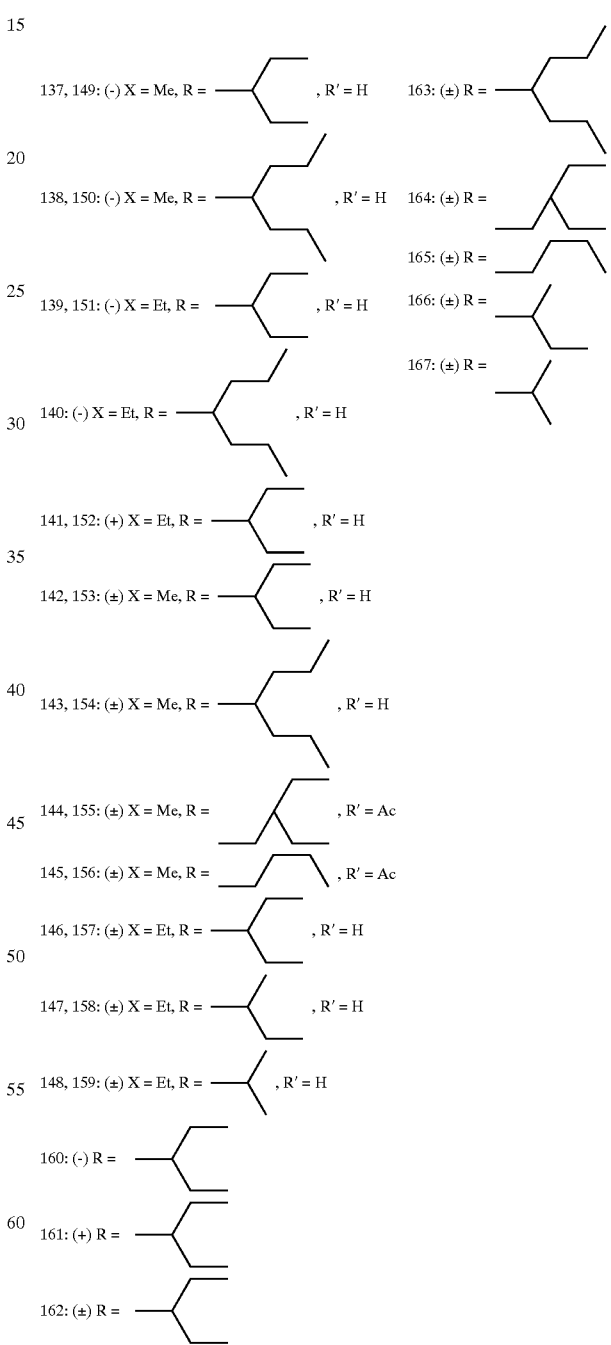
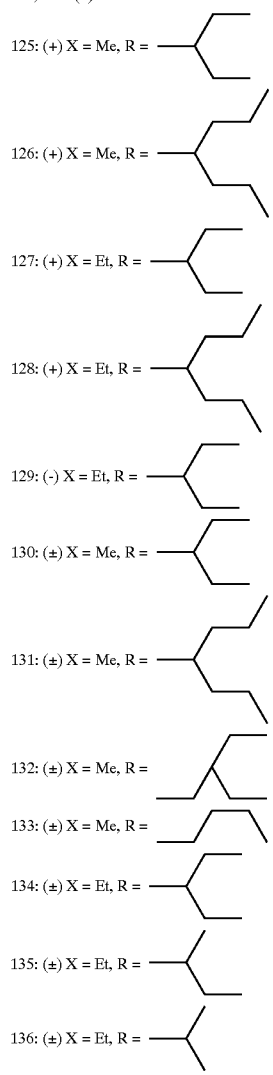
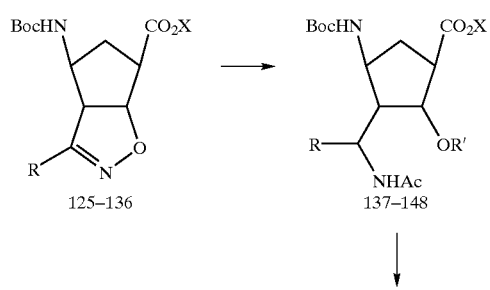

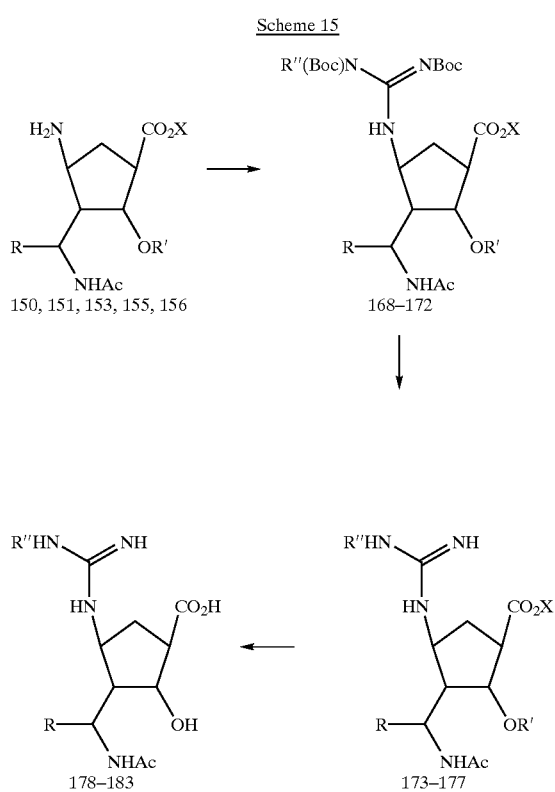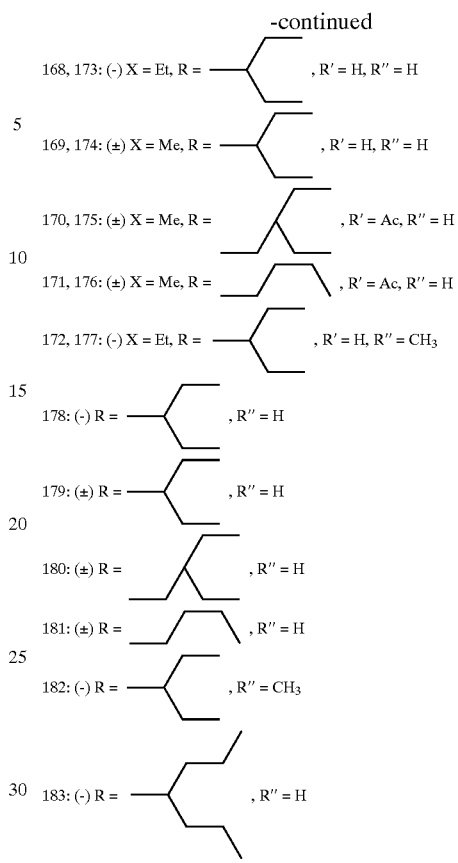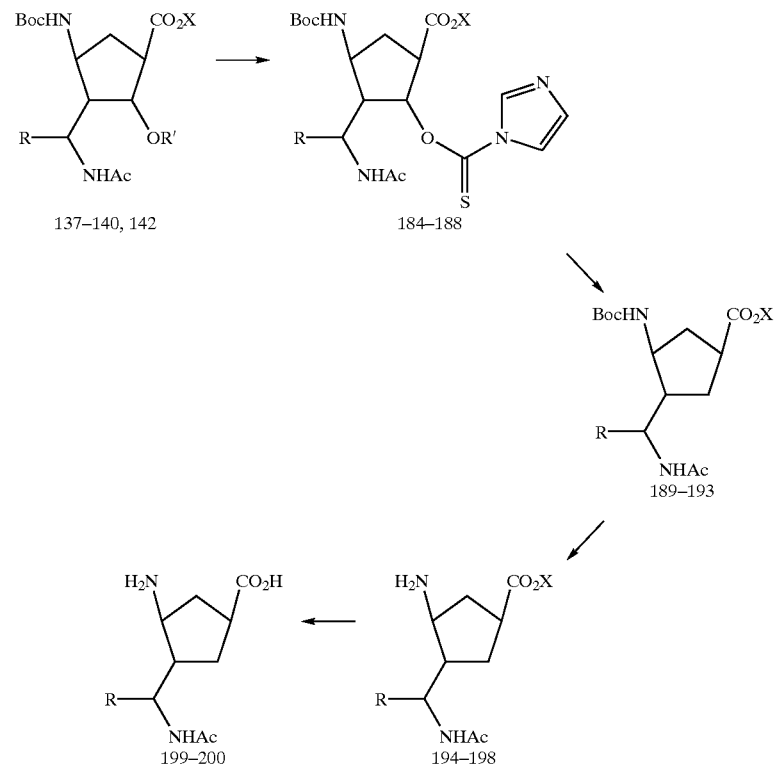

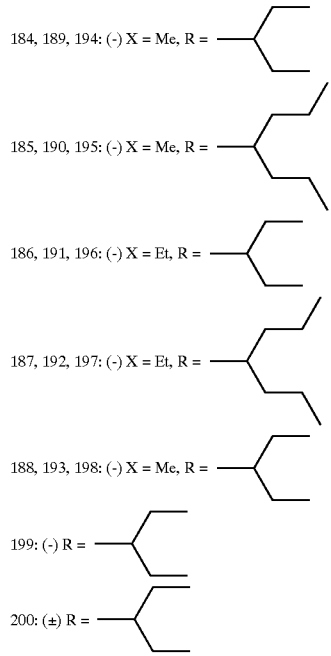
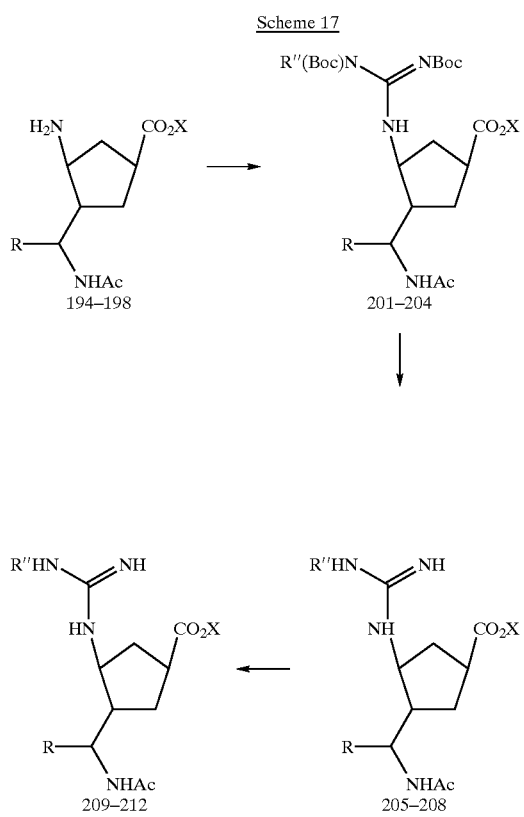
Scheme 17
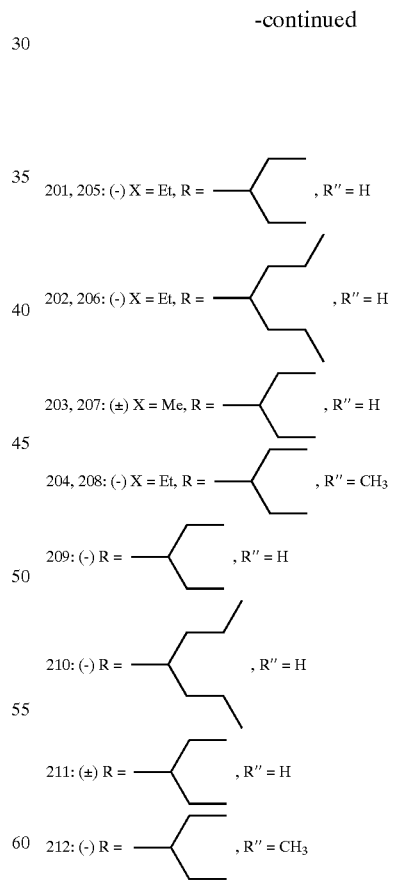

Scheme 18

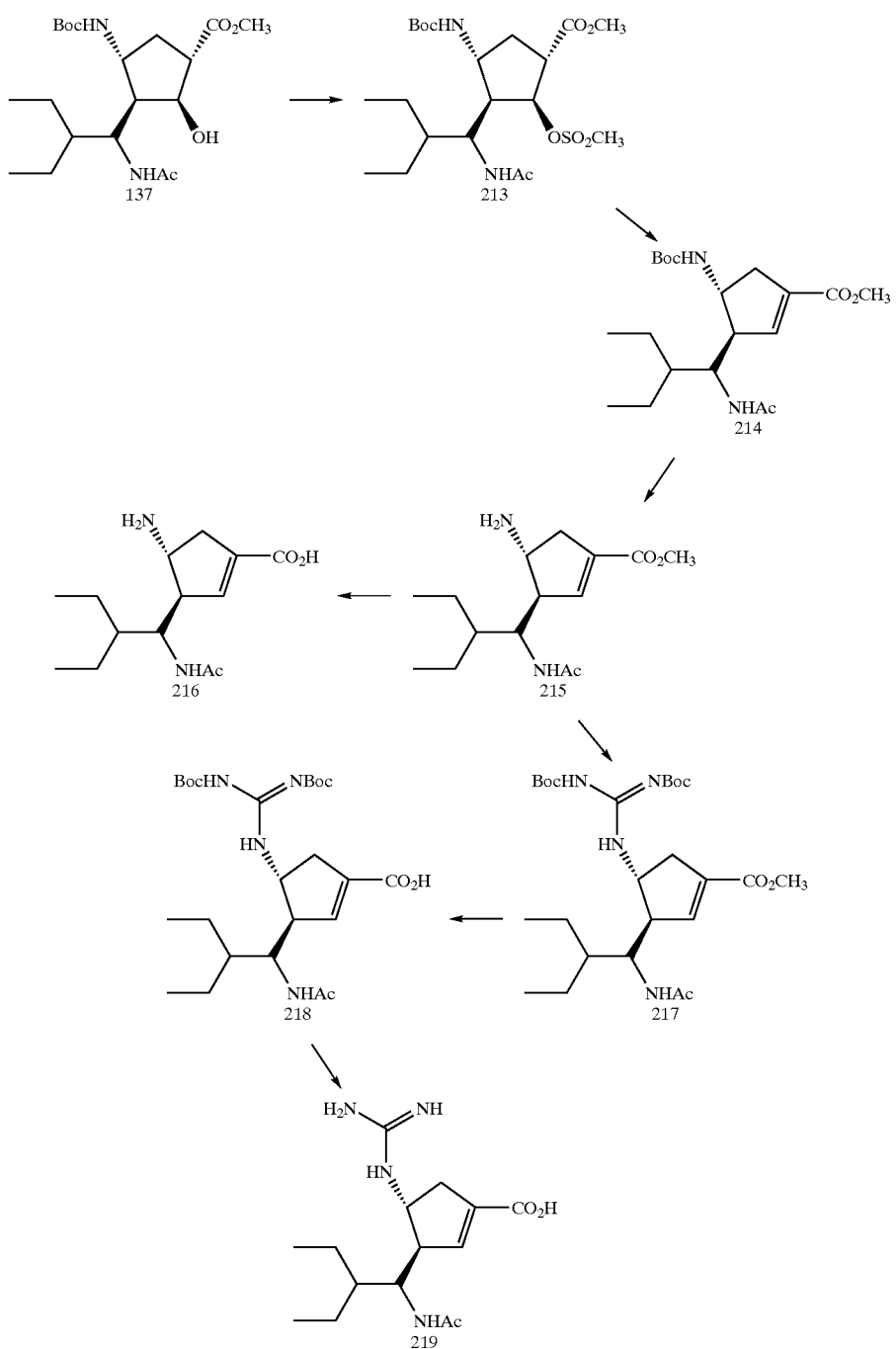

In addition, an important intermediate to the present invention, compounds 125–136, can be prepared by reacting a cyclopentene of the formula

with corresponding nitrile oxide (produced from phenyl isocyanate, and a nitroalkane in the presence of triethylamine or from chloro-oxime and triethylamine) to produce an cyclopent[d]isoxazole ring system. The product can then be hydrogenated in the presence of a $PtO_2$ in an alcohol along with HCl to open the ring and form a corresponding amino compound.

Also, process for preparing compounds of the present invention can be found in U.S. patent application Ser. No. 60/085,252 filed May 13 1998, entitled "Preparation of substituted Cyclopentane and Cyclopentene Compounds and Certain Intermediates" to Chand et al, entire disclosure of which is incorporated herein by reference.

The following non-limiting examples are presented to further illustrate the present invention.

EXAMPLE 1

(±) 4-Azidocyclopent-2-en-1-one (2, Scheme-1)

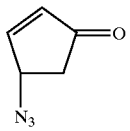

To a solution of sodium azide (2.12 g, 32.6 mmol) in DMF (15 mL) cooled to 0° C. was added dropwise with stirring 4-bromocyclopent-2-en-1-one (1, 3.5 g, 21.7 mmol, prepared by the method of DePuy et. al. J. Org. Chem. 29, 3503, 1964) in DMF (5 mL) over a period of 5 min. The reaction mixture was stirred at 0° C. for 30 min and diluted with ethyl acetate (20 mL). The reaction mixture was washed with water (2×20 mL) and brine (2×20 mL), dried (MgSO$_4$) and filtered. The filtrate was concentrated in vacuo to furnish an oily residue. Purification by flash column chromatography (silica gel, 10–15% ethyl acetate in hexane) gave 1.9 g (71%) of compound 2, as an oil.

$^1$H NMR (CDCl$_3$): δ 2.35 (dd, J=18.6 and 2.4 Hz, 1H), 2.77 (dd, J=18.6 and 6.6 Hz, 1H), 4.67 (dd, J=4.9 and 2.6 Hz, 1H), 6.35 (dd, J=5.6 and 1.5 Hz, 1H), 7.54 (dd, J=5.5 and 2.4 Hz, 1H).

EXAMPLE 2

(±) 3β-[1'-Acetylamino-1'-bis(ethoxycarbonyl)]methyl-4α-azidocyclopentan-1-one (3, Scheme-1)

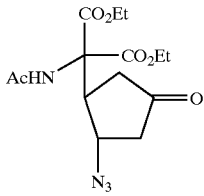

To a solution of diethylacetamido malonate (1.25 g, 5.7 mmol) in ethanol (10 mL) under nitrogen was added freshly cut sodium metal (0.03 g, 1.4 mmol). The reaction was stirred at room temperature until all sodium metal has dissolved. The reaction mixture was cooled to −40° C. and a solution of compound 2 (0.7 g, 5.7 mmol) in ethanol (5 mL) was added dropwise. The reaction mixture was stirred at −40° C. for 30 min and quenched with trifluoroacetic acid (0.1 mL, 1.4 mmol). The solvent was removed in vacuo to furnish crude compound 3 as a white solid. The solid was dissolved in ethyl acetate and washed with water, dried and concentrated in vacuo and the solid obtained was crystallized from ether/hexane to furnish 1.2 g (63%) of compound 3, as a white solid, mp. 121–122° C.

$^1$H NMR (CDCl$_3$): δ 1.26 (t, J=7.2 Hz, 3H), 1.29 (t, J=7.2 Hz, 3H), 2.05 (s, 3H), 2.27 (m, 2H), 2.54 (dd, J=18 and 8 Hz, 1H), 2.78 (dd, J=18 and 8 Hz, 1H), 3.26 (m, 1H), 4.30 (m, 4H), 4.38 (m, 1H), 6.78 (br s, 1H); IR (KBr): 3331, 2981, 2107, 1744, 1605, 1525 cm$^{-1}$; MS (ES$^+$): 341.2 (100%, M+1).

| Analysis: | Calcd for C$_{14}$H$_{20}$N$_4$O$_6$: | C, 49.41; H, 5.92; N, 16.46 |
|---|---|---|
| | Found: | C, 49.47; H, 5.95; N, 16.48 |

EXAMPLE 3

(±) 3β-[1'-Acetylamino-1'-bis(ethoxycarbonyl)]methyl-4α-tert-butoxycarbonylamino-cyclopentan-1-one (4, Scheme-1)

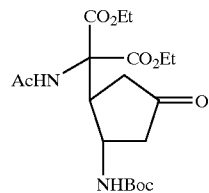

A mixture of compound 3 (0.5 g, 1.5 mmol), di-tert-butyl dicarbonate (0.39 g, 1.77 mmol), and 10% Pd/C (0.14 g) in ethyl acetate (25 mL) was hydrogenated at 45 psi for 1 h. The catalyst was removed by filtration and the filtrate was concentrated in vacuo to furnish crude compound 4. Recrystallization from ether/hexane gave 0.28 g (45%) of compound 4, as a white solid, mp 135–136° C.

$^1$H NMR (CDCl$_3$): δ 1.27 (m, 6H), 1.45 (s, 9H), 2.10 (s, 3H), 2.33 (m, 2H), 2.75 (m, 2H), 3.25 (m, 1H), 4.14 (m, 1H), 4.28 (m, 4H), 4.83 (s, 1H), 6.98 (s, 1H); IR (KBr) 3365, 2980, 1739, 1689, 1519, 1394, 1275 cm$^{-1}$; MS (CI−): 413 (10%, M−1).

| Analysis: | Calcd for C$_{19}$H$_{30}$N$_2$O$_8$: | C, 55.06; H, 7.30; N, 6.76 |
|---|---|---|
| | Found: | C, 54.63; H, 7.17; N, 6.74 |

EXAMPLE 4

(±) 2-{3β-[1'-Acetylamino-1'-bis(ethoxycarbonyl)]methyl-4α-tert-butoxycarbonyl-amino-1-cyclopentylidene}-1,3-dithiane (5, Scheme-1)

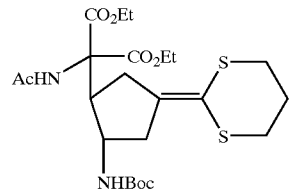

To a mixture of 2-trimethylsilyl-1,3-dithiane (7.88 g, 41.5 mmol) in THF (100 mL) at 0° C. was added dropwise under nitrogen n-BuLi (1.6 M solution in hexane, 28.6 mL, 45.7 mmol) and stirred at 0° C. for 45 min. The anion was cooled to −40° C. and a solution of compound 4 (4.3 g, 10.4 mmol) in THF (50 mL) was added dropwise and the reaction mixture was stirred at −40° C. for 5 h and warmed to −20°

C. The reaction was quenched with saturated NH₄Cl (50 mL) and warmed to room temperature, ether was added and the organic layer separated. The aqueous layer extracted with ether (2×50 mL). The organic layers were combined, dried (MgSO₄) and concentrated. The residue obtained was purified by flash column chromatography (silica gel, 30–35% ethyl acetate in hexane) to furnish 3.16 g (59%) of compound 5, as a colorless oil that solidified on standing, mp 66–68° C.

$^1$H NMR (CDCl₃): δ 1.26 (m, 6H), 1.44 (s, 9H), 2.05 (s, 3H), 2.11 (m, 2H) 2.22 (m, 2H), 2.84 (m, 5H), 2.98 (m, 2H), 3.77 (m, 1H), 4.23 (m, 4H), 4.85 (d, 1H), 6.95 (br s, 1H); IR (KBr): 3388, 2979, 2934, 1743, 1690, 1512, 1368, 1242, 1169 cm$^{-1}$; MS (ES+): 517.7 (35%, M+1).

| Analysis: | Calcd for C₂₃H₃₆N₂O₇S₂: | C, 53.47; H, 7.02; N, 5.42 |
|---|---|---|
|  | Found: | C, 53.50; H, 7.07; N, 5.41 |

EXAMPLE 5

(±) 2-{3β-(1'-Acetylamino-1'-carboxy)methyl-4α-tert-butoxycarbonylamino-1-cyclopentylidene}-1,3-dithiane (6, Mixture of Isomers at C-1', Scheme-1)

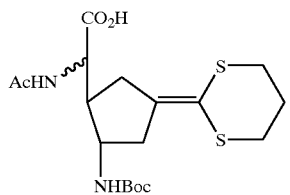

To a solution of compound 5 (7.5 g, 14.53 mmol) in ethanol (75 mL) and water (25 mL) was added 1 N NaOH (50.9 mL, 50.9 mmol) and heated at reflux for 2 h. The reaction mixture was quenched with glacial acetic acid (4.6 mL, 76.3 mmol) and heated at gentle reflux for 2 h. The solid obtained was collected by filtration, washed with water and dried in vacuo at toluene reflux temperature to furnish 1.63 g (27%) of compound 6, as a white solid. The filtrate was extracted with ethyl acetate (3×100 mL), dried (MgSO₄) and after filtration, the filtrate was concentrated in vacuo to furnish 3.5 g (58%) of compound 6. Recrystallization from ethanol gave compound 6, as a white solid, mp 174–176° C.

$^1$H NMR (CDCl₃): δ 1.35 and 1.36 (two s, 9H), 1.82 (s, 3H), 2.08 (m, 5H), 2.27 (m, 2H), 2.80 (m, 4H), 3.54 (m, 1H), 3.71 (m, 1H), 4.06 (m, 0.6H), 4.22 (m, 0.4H), 6.48 (d, J=6 Hz, 0.6H), 6.98 (m, 0.4H) 7.65 (d, J=8 Hz, 1H). The ratio of isomers at NHAc carbon atom (A and B) was 3:2; IR (KBr): 3371, 2977, 1689, 1530, 1172 cm$^{-1}$.

| Analysis: | Calcd for C₁₈H₂₈N₂O₅S₂.0.75H₂O: | C, 50.27; H, 6.91; N, 6.51 |
|---|---|---|
|  | Found: | C, 50.03; H, 6.54; N, 6.41 |

EXAMPLE 6

(±) 2-{3β-[1'-Acetylamino-1'-[(N-methoxy-N-methyl)aminocarbonyl]methyl]-4α-tert-butoxycarbonylamino-1-cyclopentylidene}-1,3-dithiane (7, mixture of isomers at C-1', Scheme-1)

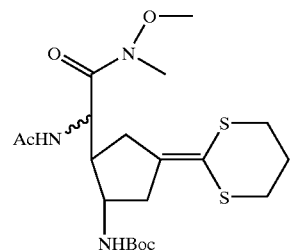

To a solution of compound 6 (5.13 g, 12.33 mmol) in THF (120 mL) at 0° C. was added dropwise, methyl chloroformate (1.01 mL, 13.56 mmol) and triethylamine (2.2 mL, 15.42 mmol) and stirred at 0° C. for 45 min. A solution of N, O-dimethylhydroxylamine hydrochloride (3.68 g, 37 mmol) and triethylamine (7 mL) in THF (25 mL) that was previously stirred for 30 min was added dropwise to the above mixture. The reaction mixture stirred further at room temperature for 16 h. It was then concentrated and to the residue, were added 0.1 N NaOH (100 mL) and ethyl acetate (100 mL). The organic layer was collected. The aqueous layer further extracted with ethyl acetate (2×75 mL). The organic layers were combined and dried (MgSO₄). After filtration, the filtrate was concentrated and the residue obtained was purified by flash column chromatography {silica gel, 90% ethyl acetate in hexane and 25% [chlororform:methanol:ammonium hydroxide (80:18:2)] in methylene chloride} to furnish 4.2 g (74%) of compound 7, as a white solid, mp 122–126° C. An analytical sample was prepared by re-crystallization from ether-hexane.

$^1$H NMR (CDCl₃): δ 1.44 (s, 9×0.5H), 1.45 (s, 9×0.5H), 2.02 (s, 3×0.5H), 2.03 (s, 3×0.5H), 2.17 (m, 4H), 2.35 (m, 0.5H), 2.58 (m, 2H), 2.77 (m, 6H), 3.19 (s, 3×0.5H), 3.22 (s, 3×0.5H), 3.57 (m, 0.5H), 3.77 (s, 3×0.5H), 3.78 (s, 3×0.5H), 3.90 (m, 0.5H), 4.60 (d, J=8 Hz, 0.5H), 4.89 (br s, 0.5H), 5.01 (br s, 0.5H), 5.16 (m, 0.5H) 6.34 (br s, 0.5H), 6.89 (br s, 0.5H). The ratio of the isomers at NHAc carbon atom (A and B) was 1:1; IR (KBr): 3341, 3269, 2978, 2936, 1715, 1681, 1653, 1521, 1156, 1171 cm$^{-1}$.

| Analysis: | Calcd for C₂₀H₃₃N₃O₅S₂: | C, 52.26; H, 7.24; N, 9.14 |
|---|---|---|
|  | Found: | C, 52.34; H, 7.20; N, 9.09 |

EXAMPLE 7

(±) 2-{3β-(1'-Acetylamino-1'-formyl)methyl-4α-tert-butoxycarbonylamino-1-cyclo pentylidene}-1,3-dithiane (8, Isomer-A at C-1', and 9, Isomer-B at C-1', Scheme-1)

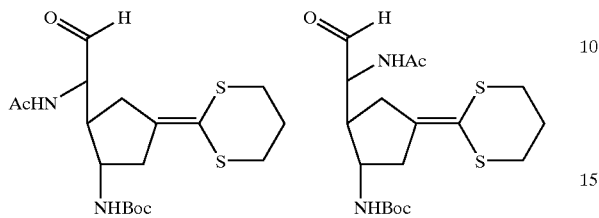

To a solution of compound 7 (0.23 g, 0.5 mmol) in THF (5 mL) at 0° C. was added dropwise lithium tri-tert-butoxyaluminohydride (1 M solution in THF, 1.1 mL, 1.1 mmol) and stirred at room temperature for 16 h. The reaction mixture was quenched carefully with 1 N HCl (1.0 mL, pH 4) and stirred for 5 min. To the reaction mixture were added, ether (10 mL), and 1.0 M aqueous sodium potassium tartrate (10 mL) and stirred at room temperature for 30 min. The organic layer was separated and the aqueous layer was extracted further with ether (2×10 mL). The organic layers were combined, dried ($MgSO_4$) and concentrated in vacuo to furnish crude aldehyde as a white solid. The crude product was purified by flash column chromatography (silica gel, 50–80% ethyl acetate in hexane) to furnish 0.08 g (40%, isomer A) of compound 8, as a white solid, mp 188–192° C. (dec).

$^1$H NMR ($CDCl_3$): δ 1.41 (s, 9H), 2.10 (m, 4H), 2.16 (s, 3H), 2.52 (m, 1H), 2.69 (dd, J=17.5 and 7.7 Hz, 1H), 2.83 (m, 5H), 3.73 (m, 1H), 4.54 (d, J=8.8 Hz, 1H), 4.77 (dd, J=9.6 and 2.1 Hz, 1H), 7.45 (d, J=9.6 Hz, 1H), 9.49 (s, 1H); IR (KBr): 3337, 2982, 1729, 1681 1535, 1166 cm$^{-1}$; MS (ES+): 401.4 (100%, M+1).

| Analysis: | Calcd for $C_{18}H_{28}N_2O_4S_2$: | C, 53.97; H, 7.05; N, 6.99 |
|---|---|---|
| | Found: | C, 53.93; H, 7.09; N, 6.93 |

Further elution gave compound 9 (0.07g, 35%, isomer B), mp>180° C.

$^1$H NMR ($CDCl_3$): δ 1.45 (s, 9H), 2.08 (s, 3H), 2.13 (m, 3H), 2.41 (m, 1H), 2.55 (m, 1H), 2.67 (dd, J=17.2 and 8 Hz, 1H), 2.84 (m, 5H), 3.70 (m, 1H), 4.38 (m, 1H), 4.79 (m, 1H), 6.76 (br s, 1H), 9.65 (s, 1H); IR (KBr): 3335, 2979, 1730, 1686, 1533, 1165 cm$^{-1}$; MS (ES+): 401.2 (20%, M+1).

| Analysis: | Calcd for $C_{18}H_{28}N_2O_4S_2$: | C, 53.97; H, 7.05; N, 6.99 |
|---|---|---|
| | Found: | C, 54.03; H, 7.05; N, 6.97 |

EXAMPLE 8

(±) 2-{3β-(1'-Acetylamino-1'-ethoxycarbonyl)methyl-4α-tert-butoxycarbonylamino-1-cyclopentylidene}-1,3-dithiane (10, Mixture of Isomers at C-1', Scheme-2)

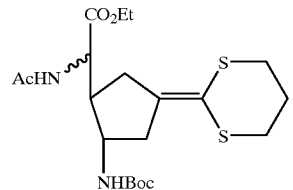

To a solution of compound 5 (3.06 g, 5.94 mmol) in ethanol (20 mL) and water (15 mL) was added 1 N NaOH (19.29 mL, 19.29 mmol) and stirred at room temperature for 16 h. The reaction mixture was quenched with glacial acetic acid (1.74 mL, 28.94 mmol) and heated at 80–90° C. for 1 h. The solid obtained was collected by filtration, washed with water and hexane and dried to furnish 1.43 g (54%) of compound 10, as a white solid, mp 157–167° C.

$^1$H NMR ($CDCl_3$): δ 1.86 (m, 3H), 1.44 (s, 9H), 2.04 (s, 1.2H), 2.09 (s, 1.8H), 2.14 (m, 3H), 2.57 (m, 2H), 2.69 (m, 1H), 2.87 (m, 5H), 3.67 (m, 0.4H), 3.87 (m, 0.6 H), 4.19 (m, 2H), 4.49 (d, J=8.6 Hz, 0.6H), 4.68 (m, 0.4H), 4.77 (dd, J=8.9 and 3.6 Hz, 1H), 6.48 (br s, 0.4H), 6.99 (d, J=8.5 Hz, 0.6H) The ratio of isomers A and B was 3:2; IR (KBr): 3338, 2982, 1740, 1681, 1545, 1530, 1170 cm$^{-1}$; MS (ES+): 445.6 (20%, M+1).

| Analysis: | Calcd for $C_{20}H_{32}N_2O_5S_2$: | C, 54.02; H, 7.25; N, 6.30 |
|---|---|---|
| | Found: | C, 54.15; H, 7.26; N, 6.30 |

EXAMPLE 9

(±) 2-{3β-(1'-Acetylamino-2'-hydroxy)ethyl-4α-tert-butoxycarbonylamino-1-cyclopentylidene}-1,3-dithiane (11, Mixture of Isomers at C-1', Scheme-2)

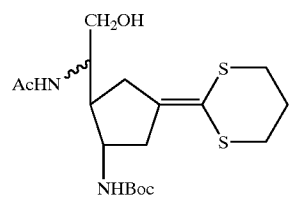

To a solution of compound 10 (0.44 g, 1 mmol) in THF (10 mL) at 0° C. was added dropwise lithium borohydride (2 M solution in THF, 1.0 mL, 2.0 mmol) and Lithium 9-BBN (1M solution in THF, 0.1 mL, 0.1 mmol). The reaction mixture was stirred at room temperature for 16 h and quenched carefully with 1 N NaOH (3 mL) and brine (3 mL) and stirred for 5 min. The reaction was acidified with glacial acetic acid and ether (10 mL) was added. The organic layer was separated and the aqueous layer extracted further with ether (2×10 mL). The organic layers were combined, dried (MgSO$_4$) and concentrated in vacuo to furnish crude alcohol as a white solid. The crude was crystallized from ethanol to furnish 0.09 g (22%) of compound 11, as a white solid, mp 222–226° C. The filtrate was purified by flash column chromatography (silica gel, 75% ethyl acetate in hexane) to furnish 0.21 g (52%) of compound 11, as a white solid.

$^1$H NMR (DMSOd$_6$): δ 1.34 (s, 9H), 1.81 (s, 3H), 2.07 (m, 6H), 2.69 (dd, J17.3 and 6.9 Hz, 1H), 2.82 (m, 4H), 3.62 (m, 2H), 3.66 (t, J=7.4 Hz, 1H), 3.73 (m, 1H), 4.59 (t, J=5.2 Hz, 1H), 6.80 (d, J=7.1 Hz, 1H), 7.43 (d, J=9.0 Hz, 1 H); IR (KBr): 3350, 1685, 1535, 1173, 1050 cm$^{-1}$; MS (ES+): 403.5 (100%, M+1).

| Analysis: | Calcd for C$_{18}$H$_{30}$N$_2$O$_4$S$_2$: | C, 53.70; H, 7.51; N, 6.96 |
|---|---|---|
| | Found: | C, 53.69; H, 7.56; N, 6.88 |

EXAMPLE 10

(±) 2-{3β-(1'-acetylamino-2'-ethoxy)ethyl-4α-(tert-butoxycarbonyl)amino-1-cyclopentylidene}-1,3-dithiane (12, Isomer-A at C-1', and 13, Mixture of Isomers at C-1', Scheme-2)

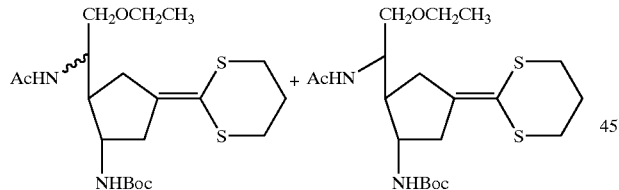

To a stirred solution of compound 11 (1.5 g, 3.73 mmol) in DMF (20 mL) at 0° C. was added 95% NaH (0.125 g, 4.95 mmol). After stirring for 1 h, ethyl iodide (0.4 mL, 6.4 mmol) was added dropwise and the reaction mixture stirred for 3 h. To the reaction mixture was added water (20 mL) and organic layer was separated. The aqueous layer was further extracted with EtOAc (4×15 mL). The combined organic extracts were washed with brine, dried (MgSO$_4$), filtered through Celite, and the filtrate concentrated in vacuo to give the crude product. Purification by radial PLC (SiO$_2$, 50% EtOAc/hexane) first afforded compound 12 (0.75 g, 47%, isomer A) as a white solid, followed by a mixture of isomers A & B, compound 13 (11%).

EXAMPLE 11

(±) Methyl-3β-(1'-acetylamino-2'-ethoxy)ethyl-4α-(tert-butoxycarbonyl)aminocyclopentan-1-carboxylate (14, Isomer-A at C-1' and Mixture at C-1', Scheme-3) and (±) Methyl 3β-(1'-Acetylamino-2'-ethoxy)ethyl-4α-aminocyclopentan-r-1-carboxylate (15, Isomer-A at C-1' and Mixture at C-1, Scheme-3)

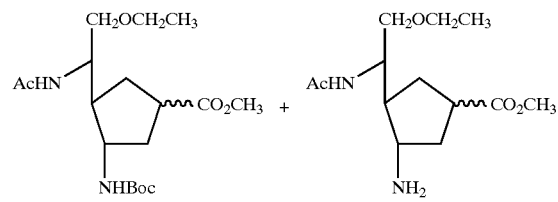

To a stirred solution of compound 12 (0.7 g, 1.63 mmol) in MeOH (48 mL) at room temperature was added 6 N HCl (4.0 mL, 24 mmol) and the reaction mixture was stirred for 24 h. To this mixture was added NaOH (1.4 g, 35 mmol) and stirred for 1 h. The reaction mixture was acidified with glacial acetic acid, filtered, and the filtrate concentrated in vacuo to give the crude product. Purification by flash column chromatography (silica gel, 75% EtOAc/hexane) gave 0.15g (34%) of compound 14, as a brown oil. Further elution with (CHCl$_3$/MeOH/NH$_4$OH, 8:1.8:0.2) provided 0.163 g (37%) of compound 15, as yellow oil.

$^1$HNMR (DMSO-d$_6$): δ 1.11 (m, 3H), 1.58 (m, 2H), 1.82 (s, 3H), 2.14–1.83 (m, 3H), 3.28–2.73 (m, 3H), 3.49–3.30 (m, 3H), 3.58 (s, 3H), 3.84–3.78 (m, 2H), 4.14 (m, 1H), 7.79–7.94 (m, 1H); IR (NaCl): 3256, 3065, 2975, 1732, 1657, 1556, 1440, 1376, 1298 cm$^{-1}$; MS (ES+): 273.0 (100%, M+1).

| Analysis: | Calcd. For C$_{13}$H$_{24}$N$_2$O$_4$: | C, 57.33; H, 8.88; N, 10.29 |
|---|---|---|
| | Calcd. For C$_{13}$H$_{24}$N$_2$O$_4$.0.2 CHCl$_3$: | C, 53.52; H, 8.23; N, 9.45 |
| | Found: | C, 53.24; H, 8.46; N, 9.04 |

EXAMPLE 12

(±) 3β-(1'-Acetylamino-2'-ethoxy)ethyl-4α-aminocyclopentan-1-carboxylic Acid (16, Isomer-A at C-1' and Mixture at C-1, Scheme-3)

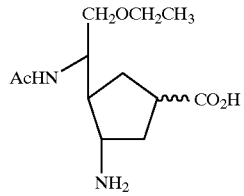

A mixture of compound 15 (0.124 g, 0.046 mmol), 1 N NaOH (0.2 mL, 0.2 mmol) and water (0.2 mL) was stirred at room temperature for 1 h. The reaction mixture was neutralized with glacial acetic acid and diluted with water to provide compound 16 as 29.2 mmolar aqueous solution.

MS (ES+): 259.0 (100%, M+1).

EXAMPLE 13

(±) 3β-(1'-Acetylamino-2'-ethoxy)ethyl-4α-[(aminoimino)methyl]aminocyclopentan-1-carboxylic Acid (17, Isomer-A at C-1' and Mixture at C-1, Scheme-3)

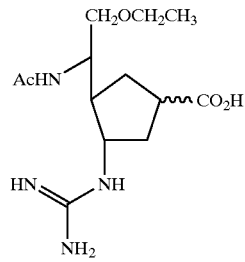

A mixture of compound 15 (0.0166 g, 0.0611 mmol), aminoiminomethane sulfonic acid (0.1 g, 0.81 mmol), and potassium carbonate (0.1 g, 0.72 mmol) in water was stirred at room temperature for 6 h. To this mixture was added 1 N NaOH (2 mL, 2 mmol) and the mixture stirred for 45 min. The reaction mixture was neutralized with glacial acetic acid, filtered through a plug of cotton, and diluted with water to provide compound 17 as 4.4 mmolar aqueous solution.

MS (ES+): 301.0 (100%, M+1).

EXAMPLE 14

(±) t-3-[1'-Acetylamino-1'-di(ethoxycarbonyl)]methyl-c-4-tert-butoxycarbonylamino-t-1-[(trismethylthio)methyl]cyclopentan-r-1-ol (18, Scheme-4)

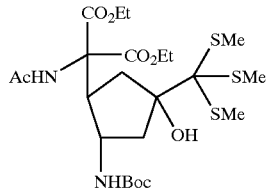

To tris(methylthio)methane (1.6 mL, 12 mmol) in THF (20 mL) at −78° C. was added dropwise, under nitrogen, n-BuLi (2.5 M solution in hexane, 5.3 mL, 13.3 mmol) and stirred at −78° C. for 30 min. To this anion at −78° C. was added, a solution of compound 4 (1.0 g, 2.4 mmol) in THF (15 mL) drop-wise and the reaction mixture was stirred at −78° C. for 3 h. It was then quenched with saturated NH$_4$Cl (15 mL) and warmed to room temperature. Ether was added and the organic layer separated. The aqueous layer extracted with ether (4×10 mL). The organic layers were combined, dried (MgSO$_4$) and concentrated in vacuo. The residue obtained was purified by radial PLC (50% ethyl acetate in hexane) to furnish compound 18 (0.48 g, 35%) as a colorless semisolid.

$^1$H NMR (CDCl$_3$): δ 1.28 (m, 6H), 1.43 (s, 9H), 1.76 (d, J=17 Hz, 1H), 2.03 (s, 3H), 2.13 (m, 1H), 2.25 (s, 9H), 2.42 (m, 1H), 2.51 (m, 1H), 2.98 (m, 1H), 3.17 (s, 1H), 3.93 (m, 1H), 4.26 (m, 4H), 5.40 (d, J=9 Hz, 1H), 7.57 (s, 1H); IR (NaCl): 3383, 2981, 1738, 1688, 1526, 1369, 1274, 1206, 1168 cm$^{-1}$; MS (ES+): 569.3 (100%, M+1).

| Analysis: | Calcd for $C_{23}H_{40}N_2O_8S_3$: | C, 48.57; H, 7.09; N, 4.93 |
|---|---|---|
| | Found: | C, 48.74; H, 7.00; N, 4.91 |

EXAMPLE 15

(±) t-3-[1'-Acetylamino-1'-carboxy)]methyl-c-4-tert-butoxycarbonylamino-t-1-[(trismethylthio)methyl]cyclopentan-r-1-ol (19, Mixture of Isomers at C-1', Scheme-4)

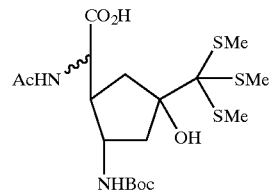

The reaction of compound 18 (3.66 g, 6.4 mmol) as described for compound 6 gave 2.25 g (75%) of compound 19, as tan solid, mp 220–223° C. (dec).

$^1$H NMR (CDCl$_3$): δ 1.36 (s, 9H), 1.49 (m, 1H), 1.81 (m, 5H), 2.16 (s, 9H), 2.48 (m, 2H), 2.61 (m, 1H), 3.66 (m, 1H), 4.03 (m, 1H), 4.93 (m, 1H), 6.40 (m, 1H), 7.52 (m, 1H); IR (KBr) 3400, 2979, 2921, 1684, 1585, 1417, 1368, 1250, 1168 cm$_{-1}$; MS (ES+): 469.3 (20%, M+1).

| Analysis: | Calcd for | C, 43.62; H, 6.71; N, 5.65 |
|---|---|---|
| | $C_{18}H_{32}N_2O_6S_2 \cdot 1.5H_2O$: | |
| | Found: | C, 43.88; H, 6.47; N, 5.28 |

EXAMPLE 16

(±) t-3-[1'-Acetylamino-1'-[(N-methoxy-N-methyl)aminocarbonyl]methyl]-c-4-tert-butoxycarbonylamino-t-1-[(trismethylthio)methyl]cyclopentan-r-1-ol (20, Mixture of Isomers at C-1', Scheme-4)

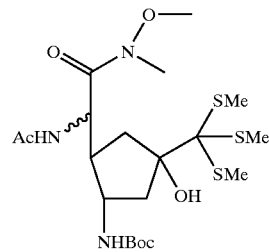

The reaction of compound 19 (6.34 g, 13.5 mmol) as described for compound 7 gave 3.85 g (56%) of compound 20, as white solid, mp 142–143° C.

$^1$H NMR (CDCl$_3$): δ 1.41 (s, 9H), 1.77 (m, 1H), 2.01 (m, 5H), 2.39 (s, 9H), 2.49 (m, 2H), 3.21 (s, 3H), 3.36 (m, 1H), 3.85 (s, 3H), 4.34 (br s, 1H), 5.11 (br s, 1H), 5.51 (m, 1H), 7.26–7.69 (m, 1H); IR (KBr): 3427, 3315, 1681, 1637 cm$^{-1}$; MS (ES+): 512.5 (M+1).

| Analysis: | Calcd for C$_{20}$H$_{37}$N$_3$O$_6$S$_3$: | C, 46.94; H, 7.29; N, 8.21 |
|---|---|---|
| | Found: | C, 47.13; H, 7.34; N, 8.16 |

EXAMPLE 17

(±) t-3-(1'-Acetylamino-1'-formyl)methyl-c-4-tert-butoxycarbonylamino-t-1-[(trismethylthio)methyl]cyclopentan-r-1-ol (21, Mixture of Isomers at C-1', Scheme-4)

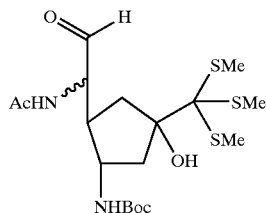

The reaction of compound 20 (1.12 g, 2.18 mmol) as described for compounds 8 and 9 gave 0.29 g (25%) of compound 21, as light yellow solid, mp 78–79° C.

$^1$H NMR (CDCl$_3$): δ 1.44 (s, 9H), 1.75–2.18 (m, 5H), 2.08 (s, 9H), 2.46 (m, 2H), 2.58 (m, 1H), 3.10 (s, 0.5H), 3.26 (s, 0.5H), 3.82 (m, 1H), 4.13 (m, 0.5H), 4.53 (m, 0.5H), 5.37 (d, J=8.8 Hz, 0.5H), 5.58 (d, J=8.5 Hz, 0.5H), 8.03 (m, 1H), 9.42 (s, 0.5H), 9.61 (s, 0.5H); IR (KBr): 3329, 2979, 2921, 1683, 1527, 1367, 1169 cm$^{-1}$; MS (ES+): 453.4 (100%, M+1).

| Analysis: | Calcd for C$_{18}$H$_{32}$N$_2$O$_5$S$_3$: | C, 47.76; H, 7.13; N, 6.19 |
|---|---|---|
| | Found | C, 47.70; H, 7.17; N, 6.11 |

EXAMPLE 18

(±) t-3-[(1'-Acetylamino-3'-ethyl-2'-oxo)pentyl]-c-4-tert-butoxycarbonylamino-t-1-[(trismethylthio)methyl]cyclopentan-r-1-ol (22, Mixture of Isomers at C-1', Scheme-4)

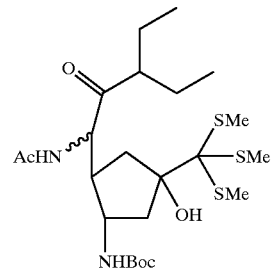

Dry Mg (17.1 g, 704 mmol) and iodine (1 crystal) were heated in a dry round bottom flask until the iodine sublimed. The heating was stopped and the purple vapors were allowed to settle on the Mg. THF (250 mL) and a few drops of 3-bromopentane were added to the reaction mixture, which was then heated to initiate the reaction. The remaining 3-bromopentane (100 mL, 805 mmol) was added dropwise to the reaction mixture at a rate that maintained a gentle reflux. After cooling to room temperature, the solution was transferred to a clean dry flask. To this mixture was added compound 21 (4.0 g, 8.84 mmol) in dry THF (100 mL) and the mixture allowed to stir at room temperature for 16 h. The reaction mixture was quenched with water (100 mL) and extracted with Et$_2$O (3×50 mL). The combined ether layers were washed with brine (3×50 mL) and dried (Na$_2$SO$_4$). The solvent was removed in vacuo to yield a crude mixture, which was purified by flash column chromatography (silica gel, 20% EtOAc/hexane) to provide 1.44 g (33%) of compound 22.

EXAMPLE 19

(±) t-3-[(1'-Acetylamino-3'-ethyl-2'-hydroxy)pentyl]-c-4-tert-butoxycarbonylamino-t-1-[(trismethylthio)methyl]cyclopentan-r-1-ol (23, Mixture of Isomers at C-1' and C-2', Scheme-4)

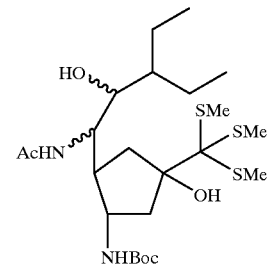

Compound 22 (1.4 g, 2.62 mmol) was combined with NaBH$_4$ (0.2 g, 5.29 mmol) in dry MeOH (20 mL), stirred at room temperature for 1 h and neutralized with glacial acetic acid. The solvent was removed in vacuo to provide a residue, which was taken up in H$_2$O and extracted with EtOAc (3×50 mL). The combined organic extracts were dried (MgSO$_4$) and concentrated to yield a crude reaction mixture which was purified by flash chromatography (silica gel, 50% EtOAc/hexane followed by 10% MeOH/EtOAc) to yield compound 23 (0.75 g, 53%).

EXAMPLE 20

(±) Methyl c-3-[(1'-Acetylamino-3'-ethyl-2'-hydroxy)pentyl]-t-4-tert-butoxycarbonyl-amino-t-1-hydroxycyclopentan-r-1-carboxylate (24, Mixture of Isomers at C-1' and C-2', Scheme-4)

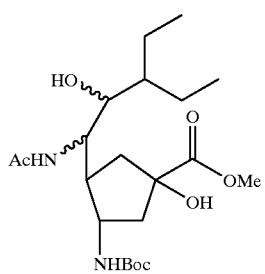

A mixture of compound 23 (0.74 g, 1.38 mmol) in MeOH/H$_2$O(12:1, 35 mL), HgCl$_2$ (1.43 g, 5.27 mmol) and HgO (0.49 g, 2.26 mmol) was stirred at room temperature for 2 h. The reaction mixture was filtered through Celite and the Celite washed with MeOH (25 mL). The filtrate was concentrated in vacuo leaving a white residue, which was partitioned, between H$_2$O (50 mL) and EtOAc (50 mL). The EtOAc layer was separated and the aqueous layer was further extracted with EtOAc (2×50 mL). The combined organic layers were washed with brine (2×50 mL), and dried (MgSO$_4$). After filtration, the filtrate was concentrated to yield a crude reaction mixture. The crude mixture was purified by flash chromatography (silica gel, 60% EtOAc/hexane) to provide compound 24 (0.27 g, 43%).

EXAMPLE 21

(±) Methyl c-3-[(1'-Acetylamino-3'-ethyl-2'-hydroxy)pentyl]-t-4-[(tert-butoxycarbonyl-amino-tert-butoxycarbonylimino)methyl]amino-t-1-hydroxycyclopentan-r-1-carboxylate (25, One Isomer at C-1' or C-2' and Mixture at Other and 26, Mixture at Both C-1' and C-2', Scheme-5)

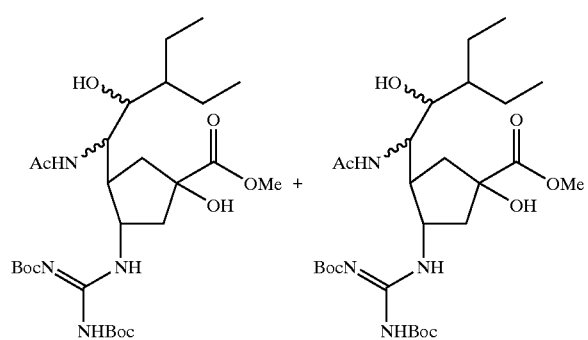

A mixture of compound 24 (0.23 g, 0.52 mmol) in CH$_2$Cl$_2$ (10 mL) and TFA (1 mL) was stirred for 16 h at room temperature. The mixture was concentrated in vacuo and traces of TFA were removed by co-evaporation with CH$_2$Cl$_2$ (2×5 mL). The residue was dried under high vacuum. To the residue were added dry DMF (5 mL), Et$_3$N (0.5 mL, 3.6 mmol), bis-(tert-butoxycarbonyl)-2-methyl-2-thiopseudourea (0.15 g, 0.52 mmol), and HgCl$_2$ (0.15 g, 0.55 mmol). The mixture was stirred at room temperature for 4 h. The mixture was diluted with EtOAc and filtered through Celite. The filtrate was washed with H$_2$O (2×50 mL), brine (2×50 mL) and dried (Na$_2$SO$_4$). After filtration, the filtrate was concentrated to provide crude product, which was purified by radial PLC (SiO$_2$) using 30% EtOAc/hexane as the eluent to first provide 0.06 g (20%) of compound 25, followed by 0.085 g (28%) of compound 26.

EXAMPLE 22

(±) c-3-[(1'-Acetylamino-3'-ethyl-2'-hydroxy)pentyl]-t-4-[aminoiminomethyl]-amino-t-1-hydroxycyclopentan-r-1-carboxylic Acid (27, Mixture of Isomers at C-1' and C-2', Scheme-5]

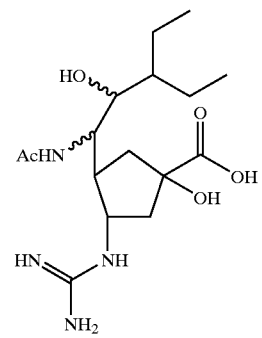

A mixture of compound 26 (0.075 g, 0.13 mmol) in CH$_2$Cl$_2$ (3 mL) was stirred with TFA (0.5 mL) for 16 h at room temperature. The reaction mixture was concentrated and dried under high vacuum to provide methyl c-3-[(1'-acetylamino-3'-ethyl-2'-hydroxy)pentyl]-t-4-[aminoiminomethyl]amino-t-1-hydroxycyclopentan-r-1-carboxylate; MS (ES+): 373 (M+1).

The above product (0.015 g, 0.04 mmol) was stirred with 1 N NaOH (0.1 mL, 0.1 mmol) and water (0.2 mL) for 16 h. The solution was neutralized with acetic acid, filtered through cotton and diluted with H$_2$O to obtain a 13.2 mmolar solution of Compound 27.

EXAMPLE 23

(±) c-3-[(1'-Acetylamino-3'-ethyl-2'-hydroxy)pentyl]-t-4-[aminoiminomethyl]-amino-t-1-hydroxycyclopentan-r-1-carboxylic Acid (28, One Isomer at C-1' or C-2' and Mixture at Other, Scheme-5)

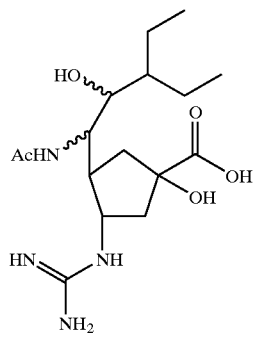

The reaction of compound 25 (0.045 g, 0.078 mmol) as described for compound 27 gave 5.37 mmolar solution of compound 28.

EXAMPLE 24

(±) 2-{3β-(1'-Acetylamino-3'-ethyl)-2'-pentenyl-4α-tert-butoxycarbonylamino-1-cyclopentylidene}-1,3-dithiane (29, Isomer-A at C-1', Mixture at C-2', Scheme-6)

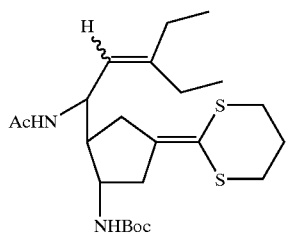

To a suspension of propyltriphenylphosphonium bromide (0.5 g, 1.3 mmol) in THF (15 mL) at −78° C. was added sodium bis(trimethylsilyl)amide, NaHMDS (1 M solution in THF, 1.3 mL, 1.3 mmol) dropwise. After stirring for 30 min, the reaction mixture was allowed to warm to 0° C. and stirred for 30 min. To this mixture was added, compound 8 (0.21 g, 0.52 mmol) in THF (10 mL) and the reaction mixture was stirred for 1 h. Additional amount of, NaHMDS (2.6 mL, 2.6 mmol) was added dropwise and the reaction mixture was stirred for 30 min followed by a dropwise addition of ethyl bromide (0.3 mL). The reaction mixture was allowed to warm to room temperature and stirred for 2 h. Water (20 mL) was added and the layers were separated. The aqueous layer was extracted with ether (4×15 mL). The combined organic extracts were washed with brine, dried (MgSO$_4$), filtered through Celite and the filtrate concentrated in vacuo to give the crude product. Purification by radial PLC (silica gel, 50–75% EtOAc/hexane) furnished compound 29 (0.045 g, 20%) as a white solid.

$^1$H NMR (CDCl$_3$): δ 0.99–0.94 (m, 3H), 1.19–1.12 (m, 3H), 1.48 (s, 9H), 1.74–1.52 (m, 2H), 2.00 (s, 3H), 2.15–2.02 (m, 6H), 2.78–2.55 (m, 2H), 2.99–2.82 (m, 4H), 3.22–3.16 (m, 2H), 5.13–4.93 (m, 1H), 5.49–5.47 (m, 1H), 5.58–5.57(m, 1H), 6.96 (bs, 1H); MS (ES+): 455.6 (100%, M+1).

| Analysis: | Calcd. for C$_{23}$H$_{38}$N$_2$O$_3$S$_2$ | C, 60.75; H, 8.42; N, 6.16 |
|---|---|---|
| | Calcd. for C$_{23}$H$_{38}$N$_2$O$_3$S$_2$.0.2 CH$_2$Cl$_2$ | C, 59.08; H, 8.21; N, 5.94 |
| | Found | C, 58.92; H, 8.21; N, 6.02 |

EXAMPLE 25

(±) Methyl 3β-(1'-Acetylamino-3'-ethyl)-2'-pentenyl-4α-(tert-butoxycarbonyl)aminocyclopentan-1-carboxylate (30, Isomer-A at C-1', Mixture of Isomers at C-1 and C-2', Scheme-6)

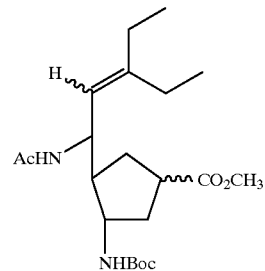

To a stirred solution of compound 29 (0.019 g, 0.042 mmol) in MeOH (1 mL) at room temperature was added 6 N HCl (0.1 mL, 0.6 mmol) and the reaction mixture was stirred for 24 h. The reaction mixture was concentrated in vacuo to give a brown residue of compound 30, which was used as such for the reaction in the following example.

EXAMPLE 26

(±) Methyl 3β-(1'-Acetylamino-3'-ethyl)-2'-pentenyl-4α-aminocyclopentan-1 Carboxylate (31, Isomer-A at C-1', Mixture of Isomers at C-1 and C-2', Scheme-6)

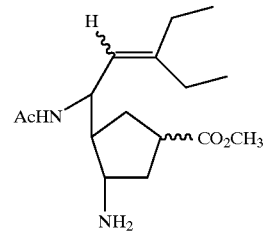

To a mixture of compound 30 (0.042 mmol) in CH$_2$Cl$_2$ (1 mL) was added CF$_3$CO$_2$H (0.1 mL, 1.3 mmol) and the mixture was stirred for 4 h and concentrated in vacuo to furnish compound 31 as a brown solid and used as such for the reaction in the following example.

EXAMPLE 27

(±) 3β-(1'-Acetylamino-3'-ethyl)-2'-pentenyl-4α-aminocyclopentan-1-carboxylic Acid (32, Isomer-A at C-1', Mixture of Isomers at C-1 and C-2', Scheme-6)

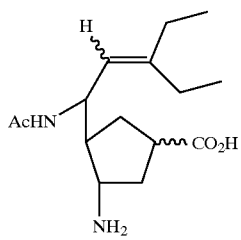

To a solution of compound 31 (0.042 mmol) in MeOH (1 mL), was added 1 N NaOH (0.7 mL, 0.7 mmol) and stirred for 1 h at room temperature. The reaction mixture was neutralized with glacial acetic acid and diluted with water to obtain a 20 mmolar solution of compound 32.

EXAMPLE 28

(±) Methyl 3β-(1'-Acetylamino-3'-ethyl)pentyl-4α-aminocyclopentan-1-carboxylate (33, Isomer-A at C-1', Mixture at C-1, Scheme-6)

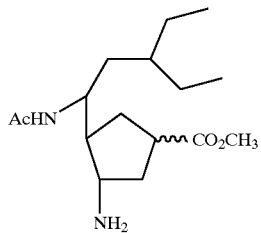

A mixture of 31 (0.2 mmol) and $PtO_2$ (0.1 g) in EtOH (10 mL) was hydrogenated under 45 psi pressure for 16 h. The catalyst was removed by filtration and the filtrate was concentrated in vacuo to furnish compound 33 (59%) as yellow oil.

$^1$H NMR (360 MHz, $CDCl_3$): δ 8.40–8.45 (bs, 2H), 7.73–7.70 (m, 1H), 3.62 (s, 3H), 3.28–2.50 (m, 3H), 2.10–1.87 (m, 4H), 1.83 (s, 3H), 1.44–1.24 (m, 3H), 1.19–1.15 (m, 8H), 0.85–0.84 (m, 3H); IR (NaCl): 3358, 2946, 2834, 1451, 1418, 1029 cm$^{-1}$; MS (ES+): 299.0 (100%, M+1).

| Analysis: | Calcd. for $C_{16}H_{30}N_2O_3$: | C, 64.39; H, 10.13; N, 9.39 |
|---|---|---|
| | Calcd. for $C_{16}H_{30}N_2O_3 \cdot 2.25\ CF_3CO_2H$: | C, 44.37; H, 5.86; N, 5.05 |
| | Found: | C, 44.25; H, 6.04; N, 5.17 |

EXAMPLE 29

(±) 3β-(1'-Acetylamino-3'-ethyl)pentyl-4α-aminocyclopentan-1-carboxylate (34, Isomer-A at C-1', Mixture at C-1, Scheme-6)

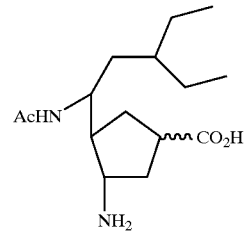

A mixture of 33 (0.0089 g, 0.03 mmol) and 1 N NaOH (0.2 mL, 0.2 mmol) in water (0.4 mL) was stirred at room temperature for 1 h. The reaction mixture was neutralized with AcOH and diluted with water to provide compound 34 as 12.1 mmolar aqueous solution.

MS (ES+): 285.1 (100%, M+1).

EXAMPLE 30

(±) Methyl 3β-(1'-Acetylamino-3'-ethyl)-2'-pentenyl-4α-aminocyclopentan-1 Carboxylate (35, Mixture of Isomers at C-1, C-1' and C-2', Scheme-7)

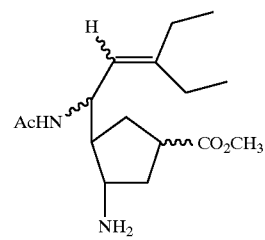

This was prepared from the mixture of compounds 8 and 9 (1.74 g, 4.5 mmol) following the same procedures as for compound 29, 30 and 31. It was obtained as yellow oil.

EXAMPLE 31

(±) Methyl 3β-(1'-Acetylamino-3'-ethyl)pentyl-4α-aminocyclopentan-1-carboxylate (36, Mixture of Isomers at C-1' and C-1, Scheme-7)

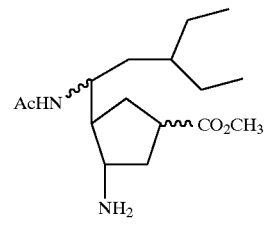

This was prepared from 35 following the same procedures as for compound 33.

$^1$H NMR (360 MHz, $CDCl_3$): δ 0.85–0.84 (m, 3H), 1.15–1.51 (m, 11H), 1.83 (s, 3H), 2.10–1.92 (m, 4H), 3.01–2.86 (m, 3H), 3.61 (s, 3H), 7.4–7.71 (m, 1H), 8.40–8.45 (bs, 2H); IR (NaCl) 3358, 2946, 2834, 1451, 1418, 1029 cm$^{-1}$; MS (ES+): 299.0 (100%, M+1).

| Analysis: | Calcd. for C$_{16}$H$_{30}$N$_2$O$_3$ | C, 64.39; H, 10.13; N, 9.39 |
|---|---|---|
| | Calcd. for C$_{16}$H$_{30}$N$_2$O$_3$.3 CF$_3$CO$_2$H.2 H$_2$O: | C, 39.05; H, 5.51; N, 4.41 |
| | Found: | C, 38.79; H, 5.13; N, 4.34 |

EXAMPLE 32

(±) 3β-(1'-Acetylamino-3'-ethyl)pentyl-4α-aminocyclopentan-1-carboxylic Acid (37, Mixture of Isomers at C-1 and C-1', Scheme-7)

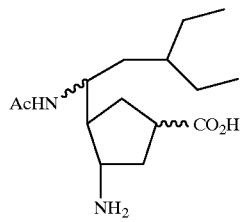

The reaction of compound 36 (0.010 g, 0.034 mmol) as described for compound 34 gave 9.8 mmolar solution of compound 37.

MS (ES+): 285.1 (100%, M+1).

EXAMPLE 33

(±) 2-{3β-(1'-Acetylamino)-2'-pentenyl-4α-tert-butoxycarbonylamino-1-cyclopentylidene}-1,3-dithiane (38, Isomer-A at C-1', Mixture at C-2', Scheme-8)

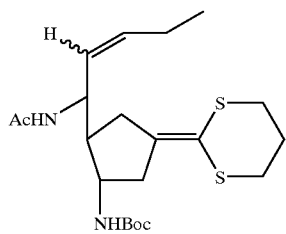

To a suspension of propyltriphenylphosphonium bromide (0.28 g, 0.73 mmol) in THF (10 mL) at −78° C. was added NaHMDS (1 M solution in THF, 0.73 mL, 0.73 mmol) dropwise. After stirring for 10 min., the reaction mixture was allowed to warm to 0° C., stirred for 20 min., and cooled to −78° C. To this mixture was added compound 8 (0.097 g, 0.24 mmol) in THF (6 mL) and the reaction mixture was stirred for 1 h. Water (10 mL) was added and the layers were separated. The aqueous layer was extracted with ether (4×10 mL). The combined organic extracts were washed with brine, dried (MgSO$_4$), filtered through Celite. After filtration, the filtrate was concentrated in vacuo to give 0.16 g of the crude product. Purification by radial PLC (silica gel, 50–75% EtOAc/hexane) furnished 0.093 g (91%) of compound 38, as a white solid, mp 175–177° C.

$^1$H NMR (360 MHz, CDCl$_3$): δ 0.95–1.0 (m, 3H), 1.45 (s, 9H), 1.97–2.27 (m, 10H), 2.56–2.72 (m, 1H), 2.82–2.86 (m, 5H), 3.82–3.88 (m, 1H), 4.45 (m, 1H), 4.71 (m, 1H), 5.33–5.44 (m, 1H), 5.58–5.75 (m, 1H) 6.54–6.61 (m, 1H); IR (KBr): 3342, 2970, 2935, 1683, 1646, 1537, 1367, 1296, 1170 cm$^{-1}$; MS (ES+): 427.5 (100%, M+1).

| Analysis: | Calcd. for C$_{21}$H$_{34}$N$_2$O$_3$S$_2$: | C, 59.12; H, 8.03; N, 6.57 |
|---|---|---|
| | Found : | C, 59.21; H, 8.04; N, 6.51 |

EXAMPLE 34

(±) Methyl 3β-(1'-Acetylamino)-2'-pentenyl-4α-tert-butoxycarbonylaminocyclopentan-1-carboxylate (39, Isomer-A at C-1' and Mixture at C-2', Scheme-8)

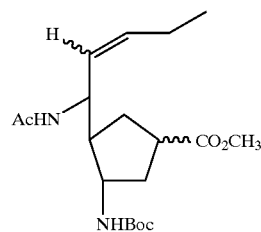

The reaction of compound 38 (4.0 g, 9.4 mmol) as described for compounds 30 gave 2.7 g (78%) of compound 39, as an oil.

EXAMPLE 35

(±) Methyl 3β-(1'-Acetylamino)pentyl-4α-tert-butoxycarbonylaminocyclopentan-1-carboxylate (40, Isomer-A at C-1', Mixture at C-1, Scheme-8)

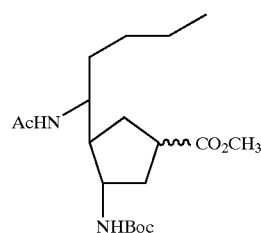

The reaction of compound 39 (0.145 g, 0.39 mmol) as described for compound 33 gave 0.14 g (97%) of compound 40, as a thick oil.

EXAMPLE 36

(±) Methyl 3β-(1'-Acetylamino)pentyl-4α-aminocyclopentan-1-carboxylate (41, Isomer-A at C-1', Mixture at C-1, Scheme-8)

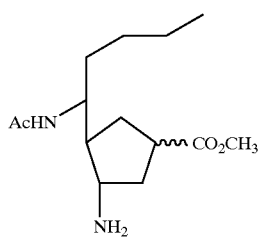

A mixture of compound 40 (0.08 g, 0.22 mmol) and TFA (0.5 mL, 6.5 mmol) in $CH_2Cl_2$ (8 mL) was stirred at room temperature for 16 h. The reaction mixture was concentrated in vacuo to give 0.112 g of compound 41.

EXAMPLE 37

(±) 3β-(1'-Acetylamino)pentyl-4α-aminocyclopentan-1-carboxylic Acid (42, Isomer-A at C-1', Mixture at C-1, Scheme-8)

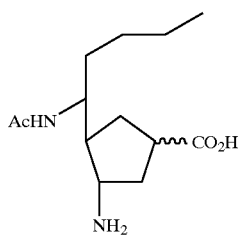

The reaction of compound 41 (0.112 g) as described for compound 34 gave 31.9 mmolar solution of compound 42.

MS (ES+): 257.4 (100%, M+1).

EXAMPLE 38

(±) Methyl Cyclopent-3-ene-1-carboxylate (43, Scheme 9), and (±) Ethyl Cyclopent-3-ene-1-carboxylate (44, Scheme 9)

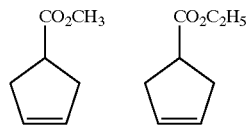

These compounds were prepared from cis-1,4-dichloro-2-butene and dimethylmalonate following the procedure of Depres et. al., J. Org. chem. 1984, 49, 928–931. The resultant acid was esterified according to the standard methods to give 43 or 44.

EXAMPLE 39

(±) Methyl 3-Butyl-4,5,6,6a-tetrahydro-3aH-cyclopenta[d]isoxazole-5-carboxylate (45, Scheme 9, Ester Group and Isooxazoline Ring are cis to Each Other), and (±) Methyl 3-Butyl-4,5,6,6a-tetrahydro-3aH-cyclopenta[d]isoxazole-5-carboxylate. (46, Scheme 9, Ester Group and Isooxazoline Ring are trans to Each Other)

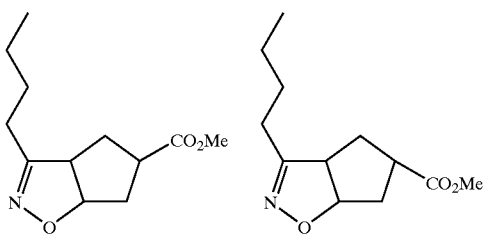

To a refluxing solution of methyl 3-cyclopenten-1-carboxylate 43 (10.21 g, 80.9 mmol) and phenyl isocyanate (17.5 mL, 161 mmol) in dry benzene (50 mL) was added dropwise, a mixture of 1-nitropentane (10.8 mL, 87.8 mmol) and $Et_3N$ (20 drops) in dry benzene (30 mL) over a period of 1 h. The mixture was heated at reflux for an additional hour. The solids were removed by filtration, and washed with $Et_2O$. The combined filtrate was concentrated to yield orange oil, which was purified by flash chromatography (silica gel, 0 to 50% ethyl acetate in hexanes). The fractions containing the desired compound were pooled together and evaporated to yield 46 (8.1 g, 45%), as yellow oil.

$^1$H NMR ($CDCl_3$): δ ppm 0.83 (t, J=7.2 Hz, 3H), 1.24–1.38 (m, 2H), 1.39–1.58 (m, 2H), 1.85–2.20 (m, 4H), 2.22–2.39 (m, 2H), 2.62–2.73 (m, 1H), 3.54–3.67 (m, 1H), 3.63 (s, 3H), 4.95–5.03 (m, 1H); MS (ES+): 225.9 (M+1).

| Analysis: | Calcd for $C_{12}H_{19}NO_3$: | C, 63.97; H, 8.52; N, 6.21 |
|---|---|---|
| | Found: | C, 63.77; H, 8.46; N, 6.25 |

Further elution gave 45 (2.0 g, 11%), as yellow oil.

$^1$H NMR ($CDCl_3$): δ ppm 0.90 (t, J=15.0 Hz, 3H), 1.27–1.40 (m, 2H), 1.41–1.63 (m, 2H), 1.92–2.05 (m, 1H), 2.13–2.45 (m, 5H), 2.78–2.86 (m, 1H), 3.48–3.58 (m, 1H), 3.62 (s, 3H), 4.91–5.03 (m, 1H); MS (ES+): 225.8 (M+1)

| Analysis: | Calcd for $C_{12}H_{19}NO_3$: | C, 63.97; H, 8.52; N, 6.21 |
|---|---|---|
| | Found: | C, 63.80; H, 8.54; N, 6.16 |

EXAMPLE 40

(±) Methyl 3-(1'-Ethylpropyl)-4,5,6,6a-tetrahydro-3aH-cyclopenta[d]isoxazole-5-carboxylate (47, Scheme 9, Ester Group and Isooxazoline Ring are trans to Each Other)

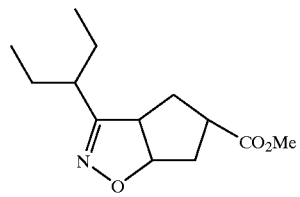

It was prepared following the procedure for compound 46 using 1-nitro-2-ethylbutane (20.3 g, 0.156 mol) and 43 (20 g, 0.158 mol) in 53% yield, as yellow oil.

$^1$H NMR (CDCl$_3$): δ ppm 0.8 (m, 6H), 1.5 (m, 4H), 1.9 (m, 2H), 2.0 (m, 1H), 2.1 (m, 1H), 2.2 (m, 1H), 2.5 (m, 1H), 3.6 (s, 3H), 3.7 (m, 1H), 4.8 (m, 1H); MS (ES+): 240 (100%, M+1).

| Analysis: | Calcd for C$_{13}$H$_{21}$NO$_3$: | C, 65.28; H, 8.78; N, 5.85 |
|---|---|---|
| | Found: | C, 65.26; H, 8.78; N, 5.92 |

EXAMPLE 41

(±) Methyl 3-(1'-Propylbutyl)-4,5,6,6a-tetrahydro-3aH-cyclopenta[d]isoxazole-5-carboxylate (48, Scheme 9, Ester Group and Isooxazoline Ring are trans to Each Other)

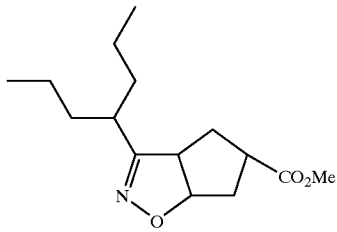

It was prepared following the procedure for compound 46 using 1-nitro-2-propylpentane (73.06 g, 460 mmol) and 43 (63 g, 515 mmol) in 45% yield as yellow oil.

$^1$H NMR (CDCl$_3$): δ ppm 0.90 (t, J=7.3 Hz, 6H), 1.24–1.37 (m, 4H), 1.42–1.55 (m, 3H), 1.63 (m, 1H), 1.98 (m, 2H), 2.06 (m, 1H), 2.39 (m, 2H), 2.79 (m, 1H), 3.61 (t, J=8.4 Hz, 1H), 3.69 (s, 3H), 5.01 (dd, J=8.5 and 5.3 Hz, 1H); MS (ES+): 225.8 (M+1).

| Analysis: | Calcd for C$_{15}$H$_{25}$NO$_3$: | C, 67.39; H, 9.42; N, 5.24 |
|---|---|---|
| | Found: | C, 67.25; H, 9.36; N, 5.17 |

EXAMPLE 42

(±) Ethyl 3-(Cyclohexylmethyl)-4,5,6,6a-tetrahydro-3aH-cyclopenta[d]isoxazole-5-carboxylate (49, Scheme 9, Ester Group and Isooxazoline Ring are trans to Each Other)

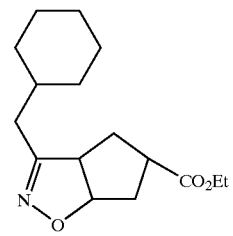

It was prepared following the procedure for compound 46 using 1-nitro-2-cyclohexylethane (3.3 g, 21 mmol) and 44 (2.68 g, 19.1 mmol) in 31% yield, as yellow oil.

$^1$H NMR (CDCl$_3$): δ ppm 0.97 (m, 2H), 1.22 (m, 6H), 1.63 (m, 6H), 2.01 (m, 4H), 2.23 (dd, J=8.9 and 15 Hz, 1H), 2.33 (dd, J=6.2 and 14 Hz, 1H), 2.74 (m, 1H), 3.62 (t, J=8.6 Hz, 1H), 4.13 (m, 2H), 5.03 (dd, J=5.5 and 8.6 Hz); MS (ES+): 280.4 (M+1).

| Analysis: | Calcd for C$_{16}$H$_{25}$NO$_3$: | C, 68.79; H, 9.02; N, 5.01 |
|---|---|---|
| | Found: | C, 68.81; H, 8.96; N, 5.06 |

EXAMPLE 43

(±) Ethyl 3-(1'-Ethylpentyl)-4,5,6,6a-tetrahydro-3aH-cyclopenta[d]isoxazole-5-carboxylate (50, Mixture of Isomers at C-1', Scheme 9, Ester Group and Isooxazoline Ring are trans to Each Other)

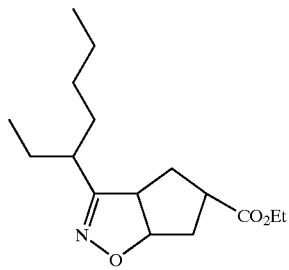

It was prepared following the procedure for compound 46 using 1-nitro-2-ethylhexane (5.75 g, 36 mmol) and 44 (4.6 g, 33 mmol) in 34% yield, as yellow oil.

EXAMPLE 44

(±) Ethyl 3-(1'-Methylethyl)-4,5,6,6a-tetrahydro-3aH-cyclopenta[d]isoxazole-5-carboxylate (51, Scheme 9, Ester Group and Isooxazoline Ring are trans to Each Other)

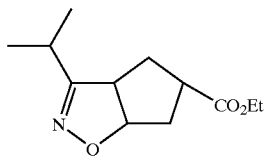

It was prepared following the procedure for compound 46 using 1-nitro-2-methylpropane (6.2 g, 60 mmol) and 44 (0.7 g, 50 mmol) in 41.5% yield, as yellow oil.

EXAMPLE 45

(±) Ethyl 3-Cyclohexyl-4,5,6,6a-tetrahydro-3aH-cyclopenta[d]isoxazole-5-carboxylate (52, Scheme 9, Ester Group and Isooxazoline Ring are trans to Each Other)

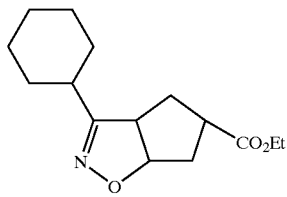

It was prepared following the procedure for compound 46 using 1-nitro-2-propylpentane (2.86 g, 20 mmol) and 44 (2.8 g, 20 mmol) in 39.6% yield, as yellow oil.

EXAMPLE 46

(±) Methyl t-3-(1'-Acetylaminopentyl)-t-4-hydroxycyclopentan-r-1-carboxylate (53, Isomer-A at C-1', Scheme 9)

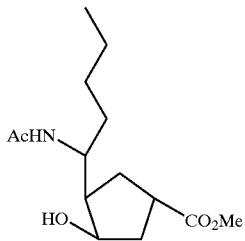

To a solution of compound 46 (3.0 g, 13.3 mmol) in THF (10 ml) was added acetic anhydride (25 mL, 27 mmol) and Raney Nickel (3 g). The mixture was hydrogenated at 35 psi for 16 h. The catalyst was removed by filtration through Celite and the filtrate was concentrated in vacuo. The crude product was purified by flash column chromatography (silica gel, 40% to 100% EtOAc in hexanes). The desired fractions were pooled together and concentrated. The residue was dissolved in MeOH (10 mL) and sodium pellets (10 mg) were added and stirred for 4 h. The reaction mixture was neutralized with AcOH and concentrated in vacuo. After the addition of water (20 ml), the mixture was extracted with EtOAc (2×20 ml). The organic layers were combined, dried (MgSO$_4$) and concentrated in vacuo. The residue was purified by flash column chromatography (silica gel, 50–80% EtOAc in hexanes). The appropriate fractions were pooled together and concentrated to give 53 in 20% yield, as a colorless oil.

$^1$H NMR (CDCl$_3$): δ ppm 0.90 (t, J=6.5 Hz, 3H), 1.32 (m, 6H), 1.90 (m, 4H), 2.05 (s, 3H), 2.09 (m, 1H), 3.19 (m, 1H), 3.67 (s, 3H), 3.81 (m, 1H), 4.07 (s, 1H), 4.52 (s, 1H), 5.38 (d, J=8.7 Hz, 1H); IR (NaCl) 3285, 2952, 1733, 1626, 1549, 1436, 1202 cm$^{-1}$; MS (ES+): 272.3 (100%, M+1).

| Analysis: | Calcd for C$_{14}$H$_{25}$NO$_4$: | C; 61.97; H; 9.29; N; 5.16 |
|---|---|---|
| | Calcd for C$_{14}$H$_{25}$NO$_4$.0.25H$_2$O: | C; 60.96; H; 9.31; N; 5.08 |
| | Found: | C; 60.79; H; 9.01; N; 5.13 |

EXAMPLE 47

(±) Methyl t-3-(1'-Acetylaminopentyl)-t-4-hydroxycyclopentan-r-1-carboxylate (54, Isomer-B at C-1', Scheme 9)

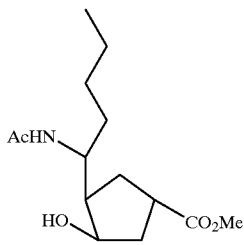

To a solution of compound 46 (3.5 g, 15.6 mmol) in THF (150 ml) was added acetic anhydride (29 mL, 31 mmol), and Platinum oxide (0.8 g). The mixture was hydrogenated at 50 psi for 24 h. The catalyst was removed by filtration through Celite and the filtrate concentrated in vacuo. The crude product was dissolved in EtOAc (50 mL), neutralized with concentrated NH$_4$OH and water (25 mL) was added. The organic layer was separated, the aqueous layer was further extracted with EtOAc (2×20 mL). The organic layers were combined, and dried (MgSO$_4$). After filtration, the filtrate was concentrated in vacuo. The residue was recrystallized from ether to give 54 in 24% yield, as white solid.

$^1$H NMR (CDCl$_3$): δ ppm 0.89 (t, J=6.5 Hz, 3H), 1.35 (m, 5H), 1.97 (m, 6H), 2.00 (s, 3H), 2.73 (s, 1H), 3.10 (m, 1H), 3.67 (s, 3H), 4.13 (m, 1H), 4.28 (d, J=2.6 Hz, 1H), 5.28 (d, J=9.2 Hz, 1H); IR (KBr) 3537, 3286, 2951, 1700, 1640, 1559, 1219 cm$^{-1}$; MS (ES+): 272.4 (100%, M+1).

| Analysis: | Calcd for C$_{14}$H$_{25}$NO$_4$: | C, 61.97; H, 9.29; N, 5.16 |
|---|---|---|
| | Found: | C, 61.78; H, 9.09; N, 5.08 |

EXAMPLE 48

(±) Methyl t-3-(1-Acetylamino-2-ethyl)butyl-t-4-hydroxycyclopentan-r-1-carboxylate (55, Isomer-A at C-1', Scheme 9)

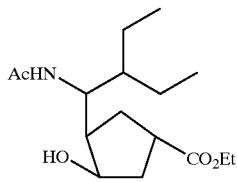

To a solution of compound 47 (0.5 g, 2 mmol) in a mixture of $CH_3CN:H_2O$ (15:1, 50 mL) was added $Mo(CO)_6$ (0.2 g, 0.8 mmol) and $NaBH_4$ (91 mg, 2.4 mmol). The reaction mixture was refluxed for 3 h, cooled to room temperature and evaporated to dryness. To the resulting mixture, were added EtOAc (50 mL), acetic anhydride (3.78 mL, 40 mmol) and the reaction mixture stirred for 16 h at room temperature. The reaction mixture was then evaporated to dryness and the residue was purified by flash column chromatography (silica gel, 0 to 100% EtOAc in hexanes). The appropriate fractions were pooled together and concentrated to give 55 in 20% yield, as white solid.

$^1H$ NMR (DMSO-d6): δ ppm 0.8 (t, J=7.2 Hz, 3H), 0.9 (t, J=7 Hz, 3H), 1.0 (m, 1H) 1.2 (m, 2H), 1.4 (m, 2H), 1.6 (m, 1H), 1.7 (m, 2H), 1.8 (m, 2H), 1.88 (s, 3H), 3.0 (m, 1H), 3.6 (s, 3H), 3.9 (m, 2H), 4.5 (s, 1H), 7.5 (d, J=9.5 Hz, 1H); MS (ES+): 244.13 (M+1).

EXAMPLE 49

(±) Methyl t-3-[(1'-Acetylamino-2'-ethyl)butyl]-t-4-hydroxycyclopentan-r-1-carboxylate (56, Isomer-B at C-1', Scheme 9)

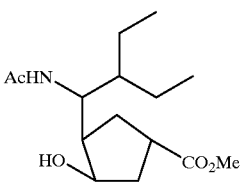

This was obtained in 61% yield as colorless oil from 47 (15 g, 62.7 mmol) using the same procedure as for compound 54.

$^1H$ NMR (DMSO-d6): δ ppm 0.8 (m, 6H), 1.0 (m, 2H), 1.3 (m, 2H), 1.4 (m, 1H), 1.7 (m, 1H), 1.8 (s, 3H), 1.9 (m, 3H), 2.0 (m, 1H), 3.0 (m, 1H), 3.6 (s, 3H), 4.0 (m, 1H), 4.1 (dd, J=1.4 and 10.4 Hz, 1H), 4.5 (d, 1H, J=4.3 Hz), 7.3 (d, J=10.2 Hz, 1H); MS (ES+): 286.3 (100% M+1).

| Analysis: | Calcd for $C_{15}H_{27}NO_4$ 0.75 $H_2O$: | C: 60.31; H: 9.54; N: 4.69 |
|---|---|---|
| | Found: | C: 60.24; H: 9.51; N: 4.59 |

EXAMPLE 50

(±) Methyl t-3-(1'-Acetylamino-2'-propyl)pentyl-t-4-hydroxycyclopentan-r-1-carboxylate (57, Isomer-B at C-1', Scheme 9)

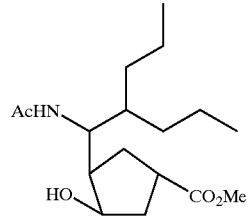

To a mixture of compound 48 (14 g, 52 mmol) dissolved in $MeOH/H_2O/AcOH$ (120/15/15 mL) was added $PtO_2$ (1.4 g) and the mixture was hydrogenated at 50 psi for 16 h. The catalyst was removed by filtration, and the filtrate concentrated to give the amino derivative. The above crude product was dissolved in $CH_2Cl_2$ (250 ml), acetic anhydride (55 ml, 520 mmol) was added, and the reaction mixture stirred for 45 min at room temperature. To the mixture was added concentrated $NH_4OH$ to pH 8. The organic layer was separated, washed with brine, dried and concentrated in vacuo. The residual oil was crystallized from ether/hexane to furnish compound 57 in 64% yield, as white solid.

$^1H$ NMR ($CDCl_3$): δ ppm 0.9 (m, 6H), 1.06 (m, 1H), 1.14 (m, 1H), 1.32 (m, 4H), 1.44 (m, 2H), 1.52 (m, 1H), 1.96 (m, 5H), 2.00 (s, 3H), 2.59 (d, J=3.1 HZ, 1H), 3.10 (m, 1H), 3.67 (s, 3H), 4.21 (m, 1H), 4.27 (m 1H), 5.29 (d, J=10 Hz, 1H); IR (KBr) : 3493, 3277, 2955, 2930, 2870, 1734, 1713, 1642, 1560, 1442, 1372, 1216 $cm^{-1}$; MS (ES+): 314.5 (20%, M+1).

| Analysis: | Calcd. for $C_{17}H_{31}NO_4$: | C: 65.14; H: 9.97; N: 4.47 |
|---|---|---|
| | Found: | C: 65.19; H: 10.04; N: 4.50 |

EXAMPLE 51

(±) Ethyl t-3-(1'-Acetylamino-2'-cyclohexyl)ethyl-t-4-hydroxycyclopentan-r-1-carboxylate (58, Isomer-B at C-1', Scheme 9)

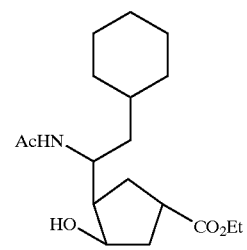

This was obtained in 68.5% yield as yellow oil from 49 (0.5 g, 1.79 mmol) using the same procedure as for compound 54.

$^1H$ NMR ($CDCl_3$): δ ppm 0.82–0.99 (m, 2H), 1.10–1.23 (m, 4H), 1.25 (t, 3H), 1.28–1.42 (m, 4H), 1.58–1.70 (m, 4H), 1.97–2.05 (m, 3H), 2.00 (s, 3H), 2.80 (d, 1H), 3.06 (m, 1H), 4.12 (m, 3H), 4.26 (m, 2H), 5.18 (d, 1H); MS (ES+): 326.5 (M+1).

| Analysis: | Calcd. for $C_{18}H_{31}NO_4 \cdot 0.25\ H_2O$: | C, 65.52; H, 9.62; N, 4.25 |
|---|---|---|
| | Found: | C, 65.48; H, 9.63; N, 4.27. |

EXAMPLE 52

(±) Ethyl t-3-(1'-Acetylamino-2'-ethyl)hexyl-t-4-hydroxycyclopentan-r-1-carboxylate (59, Isomer-B at C-1' and Mixture at C-2', Scheme 9)

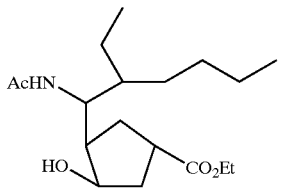

This was obtained in 34% yield as oil from 50 (1.0 g, 3.55 mmol) using the same procedure as for compound 54.

EXAMPLE 53

(±) Ethyl t-3-(1'-Acetylamino-2'-methyl)propyl-t-4-hydroxycyclopentan-r-1-carboxylate (60, Isomer-B at C-1', Scheme 9)

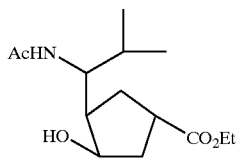

This was obtained in 15.5% yield as oil from 51 (0.98 g, 4.1 mmol) using the same procedure as for compound 54.

MS (ES+): 272.1 (M+1).

EXAMPLE 54

(±) Ethyl t-3-(1'-Acetylamino-1'-cyclohexyl)methyl-t-4-hydroxycyclopentan-r-1-carboxylate (61, Isomer-B at C-1', Scheme 9)

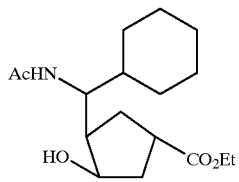

This was obtained in 17% yield as oil from 52 (1 g, 3.77 mmol) using the same procedure as for compound 54.

MS (ES+): 312.0 (M+1).

EXAMPLE 55

(±) t-3-(1'-Acetylaminopentyl)-t-4-hydroxycyclopentan-r-1-carboxylic Acid (62, Isomer-A at C-1', Scheme 9)

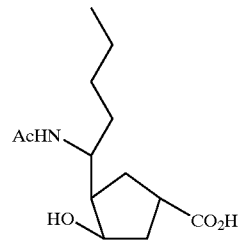

To a mixture of 53 (0.1 g, 0.37 mmol) in THF (2 mL) and EtOH (2 mL) was added 1N NaOH (0.93 mL, 0.93 mmol) and water (2 mL). The mixture was stirred for 30 min. The solvent was removed, the residue was taken up in $H_2O$ and extracted with EtOAc (5 mL). The aqueous layer was acidified (pH 4) and extracted with EtOAc (2×5 mL). The organic extracts from the acidic mixture were combined, and dried ($MgSO_4$). After filtration, the filtrate was concentrated and triturated with ether/hexane to give compound 62 (84%) as white solid.

$^1$H NMR (DMSO-d6): δ ppm 0.85 (t, J=5.0 Hz, 3H), 1.26 (m, 6H), 1.74 (m, 5H), 1.86 (s, 3H), 2.92 (m, 1H), 3.54 (m, 1H), 3.90 (s, 1H), 4.60 (s, 1H), 7.87 (d, J=8.6 Hz, 1H), 11.96 (s, 1H); IR (KBr): 3259, 3112, 1727, 1607, 1200 cm$^{-1}$; MS (ES+) 258.4 (100%, M+1).

| Analysis: | Calcd. for $C_{13}H_{23}NO_4$: | C, 60.68; H, 9.01; N, 5.44 |
|---|---|---|
| | Found: | C, 60.63; H, 9.00; N, 5.45 |

EXAMPLE 56

(±) t-3-(1'-Acetylaminopentyl)-t-4-hydroxycyclopentan-r-1-carboxylic Acid (63, Mixture of Isomers at C-1', Scheme 9)

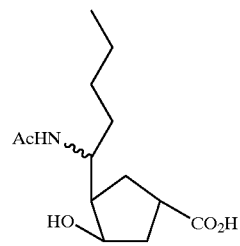

To a mixture of compound 46 (3.0 g, 13.3 mmol) in THF (100 ml) was added acetic anhydride (25 mL, 270 mmol) and Raney Nickel (3 g). The mixture was hydrogenated at 35 psi for 16 h. The catalyst was removed by filtration through Celite and the filtrate was concentrated in vacuo. The crude product was purified by flash column chromatography (silica gel, 40–100% EtOAc in hexanes). The appropriate fractions were combined together and concentrated.

To the above obtained ester (0.15 g), were added THF (2 mL), EtOH (2 mL) and 1 N NaOH (2 mL, 2 mmol). The reaction mixture was stirred at room temperature for 30 min and concentrated in vacuo to remove organic solvent. The aqueous layer was washed with EtOAc and acidified to pH 4 using 1 N HCl. The aqueous layer was saturated with sodium chloride and extracted with EtOAc (2×5 mL). The organic extracts from the acidic layer were combined, and dried (MgSO$_4$). After filtration, the filtrate was concentrated in vacuo. The residue was triturated with ether/hexane (1:1) to furnish compound 63, as white solid.

$^1$H NMR (DMSO-d6): δ 0.83 (m, 3H), 1.3 (m, 5H), 1.9 (m, 6H), 2.9 (m, 1H), 3.35 (s, 3H), 3.5 (m, 0.4H), 3.85 (m, 0.6H), 3.95 (s, 0.4H), 4.05 (s, 0.6H), 4.6 (s, 0.6H), 4.7 (s, 0.4H), 7.44 (d, J=9.5 Hz, 0.6H), 8.0 (d, J=9.5 Hz, 0.4H), 12.0 (s, 1H); IR (KBr) 3303, 2951, 2934, 1726, 1688, 1650, 1550, 1202 cm$^{-1}$; MS (ES+): 258.4 (100%, M+1).

| Analysis: | Calcd for C$_{13}$H$_{23}$NO$_4$: | C, 60.68; H, 9.01; N, 5.44 |
|---|---|---|
| | Found: | C, 60.67; H, 8.96; N, 5.42 |

EXAMPLE 57

(±) t-3-(1'-Acetylaminopentyl)-t-4-hydroxycyclopentan-r-1-carboxylic Acid (64, Isomer-B at C-1', Scheme 9)

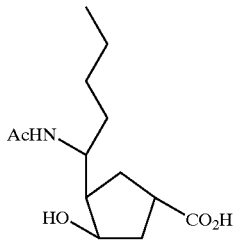

This was obtained in 61% yield as a hygroscopic solid from 54 (0.15 g, 0.48 mmol) using the same procedure as for compound 62.

$^1$H NMR (DMSO-d6): δ ppm 0.83 (t, J=6.5 Hz, 3H), 1.26 (m, 5H), 1.47 (m, 2H), 1.61 (m, 1H), 1.71 (m, 1H), 1.79 (s, 3H), 1.91 (m, 1H), 2.02 (m, 1H), 2.56 (m, 1H), 3.37 (m, 1H), 3.68 (m, 1H), 3.80 (dd, J=13.0 and 6.6 Hz, 1H), 7.44 (d, J=9.5 Hz, 1H), 11.8 (brs, 1H); IR (NaCl) 3303, 2957, 2934, 1708, 1628, 1556, 1376 and 1221 cm$^{-1}$; MS (ES+): 258.3 (100%, M+1).

| Analysis: | Calcd for C$_{13}$H$_{23}$NO$_4$: | C, 60.68; H, 9.01; N, 5.44 |
|---|---|---|
| | Calcd for C$_{13}$H$_{23}$NO$_4$·0.33 H$_2$O: | C, 59.30; H, 9.06; N, 5.32 |
| | Found: | C, 59.08; H, 8.85; N, 5.13 |

EXAMPLE 58

(±) t-3-(1'-Acetylamino-2'-ethyl)butyl-t-4-hydroxycyclopentan-r-1-carboxylic Acid (65, Isomer-A at C-1', Scheme 9)

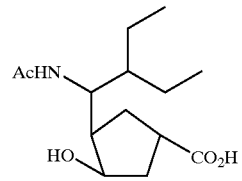

A mixture of compound 55 (8.4 mg, 0.03 mmol), 1N sodium hydroxide (0.1 ml, 0.1 mmol), and water (0.2 ml) was stirred at room temperature for 2 h. The mixture was neutralized with 1N hydrochloric acid and diluted with water to obtain 29.4 mmolar solution.

MS (ES+): 272.2 (M+1).

EXAMPLE 59

(±) t-3-(1'-Acetylamino-2'-ethyl)butyl-t-4-hydroxycyclopentan-r-1-carboxylic Acid (66, Isomer-B at C-1', Scheme 9)

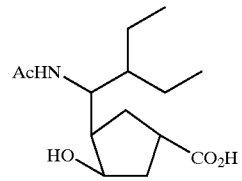

This was obtained as 44.2 mmolar solution from 56 (5.3 mg, 0.0177 mmol) using the same procedure as for compound 65.

MS (ES+): 272.2 (M+1).

EXAMPLE 60

(±) t-3-(1'-Acetylamino-2'-propyl)pentyl-t-4-hydroxycyclopentan-r-1-carboxylic Acid (67, Isomer-B at C-1', Scheme 9)

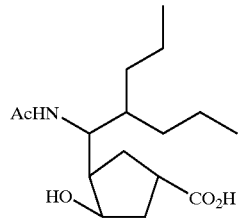

To a solution of compound 57 (0.15 g, 0.48 mmol) in THF (2 mL) and MeOH (2 mL) was added 1 N NaOH (1.9 mL, 1.9 mmol) and water (1 ml). After stirring at room temperature for 1 h, the mixture was acidified to pH 3 using 6 N HCl. The solid was collected by filtration and dried in vacuo to yield compound 67 in 96% yield, as white solid.

$^1$H NMR (DMSO-d6): δ ppm 0.80 (t, J=7.0 Hz, 3H), 0.88 (t, J=7.0 Hz, 3H), 0.99 (m, 2H), 1.11 (m, 1H), 1.22 (m, 2H), 1.41 (m, 3H), 1.52 (m, 1H), 1.66 (m, 1H), 1.78 (s, 3H), 1.83 (m, 3H), 1.92 (m, 1H), 2.86 (m, 1H), 3.95 (d, J=2.8 Hz, 1H), 4.07 (dt, J=10.8 and 1.4 Hz, 1H), 4.42 (d, J=4.2 Hz, 1H), 7.24 (d, J=10.3 Hz, 1H), 11.92 (s, 1H); IR (KBr) 3369, 2962, 2934, 1695, 1596, 1548, 1217 cm$^{-1}$; MS (ES+): 300.4 (100%, M+1).

| Analysis: | Calcd for $C_{16}H_{29}NO_4$: | C, 64.19; H, 9.76; N; 4.68 |
|---|---|---|
|  | Found: | C, 64.04; H, 9.73, N; 4.68 |

EXAMPLE 61

(±) t-3-(1'-Acetylamino-2'-cyclohexyl)ethyl-t-4-hydroxycyclopentan-r-1-carboxylic Acid (68, Isomer-B at C-1', Scheme 9)

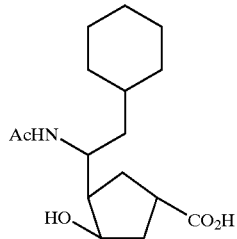

This was obtained as 50 mmolar solution from 58 (6.5 mg, 0.02 mmol) using the same procedure as for compound 65.

MS (ES+): 320.4 (M+Na).

EXAMPLE 62

(±) t-3-(1'-Acetylamino-2'-ethyl)hexyl-t-4-hydroxycyclopentan-r-1-carboxylic Acid (69, Isomer-B at C-1' and Mixture at C-2', Scheme 9)

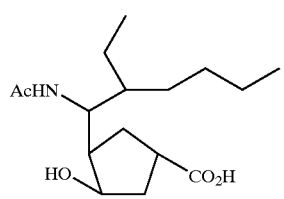

This was obtained as 76 mmolar solution from 59 (10 mg, 0.0306 mmol) using the same procedure as for compound 65.

MS (ES+): 300.5 (M+1).

EXAMPLE 63

(±) t-3-(1'-Acetylamino-2'-methyl)propyl-t-4-hydroxycyclopentan-r-1-carboxylic Acid (70, Isomer-B at C-1', Scheme 9)

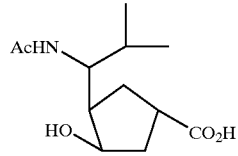

This was obtained as 80 mmolar solution from 60 (10 mg, 0.032 mmol) using the same procedure as for compound 65.

MS (ES+): 266.0 (M+Na).

EXAMPLE 64

(±) t-3-(1'-Acetylamino-1-cyclohexyl)methyl-t-4-hydroxycyclopentan-r-1-carboxylic Acid (71, Isomer-B at C-1', Scheme 9)

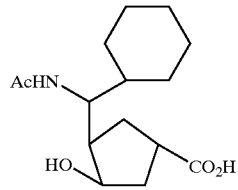

This was obtained as 80 mmolar solution from 61 (10 mg, 0.032 mmol) using the same procedure as for compound 65.

MS (ES+): 305.9 (M+Na).

EXAMPLE 65

(±) Methyl t-3-(1'-Acetylaminopentyl)-t-4-methanesulfonyloxycyclopentan-r-1-carboxylate (72, Isomer-A at C-1', Scheme 9)

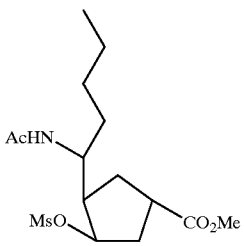

Methanesulfonyl chloride (0.3 mL, 3.87 mmol) and Et$_3$N (0.75 mL, 5.38 mmol) were added to a mixture of 53 (0.59 g, 2.17 mmol) and DMAP (30 mg, 0.24 mmol) in dry CH₂Cl₂ (10 mL) cooled to 4° C. After stirring at this temperature overnight, the reaction was quenched with H₂O and extracted with CH₂Cl₂ (2×50 mL). The combined organic extracts were washed with brine, and dried (MgSO₄). After filtration, the filtrate was concentrated in vacuo to yield compound 72 (83%) as an oil.

EXAMPLE 66

(±) Methyl t-3-(1'-Acetylaminopentyl)-t-4-methanesulfonyloxycyclopentan-r-1-carboxylate (73, Isomer-B at C-1', Scheme 9)

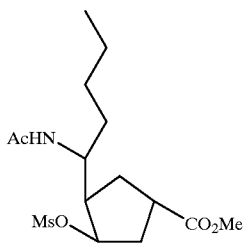

This was prepared from 54 (2.13 g, 7.85 mmol) using the same procedure as for compound 72 in 41% yield. It was re-crystallized from ether/hexane to give the desired compound as a white solid.

¹H NMR (CDCl₃): δ ppm 0.91 (m, 3H), 1.20–1.45 (m, 4H), 1.53–1.80 (m, 2H), 1.98 (s, 3H), 2.01–2.21 (m, 4H), 2.48–2.51 (m, 1H), 3.02 (s, 3H), 3.04–3.10 (m, 1H), 3.65 (s, 3H), 4.00–4.15 (m, 1H), 5.15–5.25 (m, 2H); MS (ES+): 350.4 (M+1).

| Analysis: | Calcd for C₁₅H₂₇NO₆S: | C, 51.56; H, 7.79; N, 4.01 |
|---|---|---|
| | Found: | C, 51.44; H, 7.75; N, 4.25 |

EXAMPLE 67

(±) Methy-t-3-(1'-Acetylamino-2'-ethyl)butyl-t-4-methanesulfonyloxycyclopentan-r-1-carboxylate (74, Isomer-B at C-1', Scheme 9)

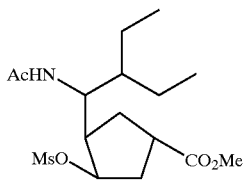

This was prepared from 56 (5.18 g, 18.2 mmol) using the same procedure as for compound 72 in 20% yield, as yellow oil.

EXAMPLE 68

(±) Methyl t-3-(1'-Acetylamino-2'-propyl)pentyl-t-4-methanesulfonyloxycyclopentan-r-1-carboxylate (75, Isomer-B at C-1', Scheme 9)

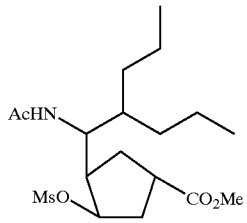

This was prepared from 57 (1.92 g, 6.13 mmol) using the same procedure as for compound 72 in 81% yield.

EXAMPLE 69

(±) Methyl t-3-(1'-Acetylaminopentyl)-c-4-azidocyclopentan-r-1-carboxylate (76, Isomer-A at C-1', Scheme 9)

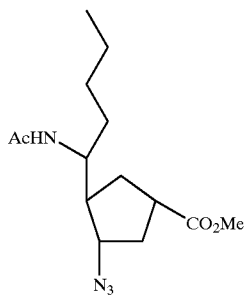

To a mixture of compound 72 (0.6 g, 1.72 mmol) in dry DMF (6 mL) was added sodium azide (0.47 g, 7.2 mmol) and heated to 80° C. for 3 h. The reaction was quenched with H₂O (5 mL) and extracted with EtOAc (2×10 mL). The combined extracts were washed with H₂O (2×5 mL), and dried (MgSO₄). After filtration, the filtrate was concentrated to yield a crude oil which was separated on a silica gel flash column using a mixture of 8 parts of dichloromethane and 2 parts of [chloroform (80): methanol (18): ammonium hydroxide (2)] as an eluent to give 0.45 g (88%) of 76, as white solid.

EXAMPLE 70

(±) Methyl-t-3-(1'-Acetylaminopentyl)-c-4-azidocyclopentan-r-1-carboxylate (77, Isomer-B at C-1', Scheme 9)

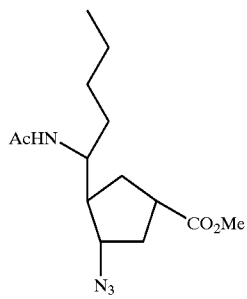

This was prepared from 73 (2.4 g, 6.87 mmol) using the same procedure as for compound 76 in 85% yield, as white solid.

$^1$H NMR (CDCl$_3$): δ ppm 0.90 (m, 3H), 1.20–1.40 (m, 5H), 1.58–1.69 (m, 2H), 1.95–2.13 (m, 3H), 2.01 (s, 3H), 2.29–2.39 (m, 1H), 2.75–2.80 (m, 1H), 3.50–3.61 (m, 1H), 3.65 (s, 3H), 4.05–4.10 (m, 1H), 5.20 (d, 1H, J=6 Hz); MS (ES+): 297.4 (M+1); IR (KBr): 3200, 3085, 2091, 1737, 1645 cm$^{-1}$.

| Analysis: | Calcd for C$_{14}$H$_{24}$N$_4$O$_3$: | C, 56.74; H, 8.16; N, 18.90 |
|---|---|---|
| | Found: | C, 56.83; H, 8.14; N, 18.81 |

EXAMPLE 71

(±) Methyl t-3-[(1'-Acetylamino-2'-ethyl)butyl]-c-4-azidocyclopentan-r-1-carboxylate (78, Isomer-B at C-1', Scheme 9)

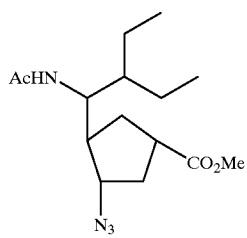

This was prepared from 74 (1 g, 2.7 mmol) using the same procedure as for compound 76 in 74% yield.

EXAMPLE 72

(±) Methyl t-3-(1'-Acetylamino-2'-propyl)pentyl-c-4-azidocyclopentan-r-1-carboxylate (79, Isomer-B at C-1', Scheme 9)

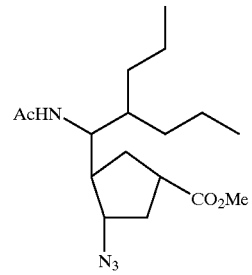

This was prepared from 75 (0.56 g, 1.44 mmol) using the same procedure as for compound 76 in 31% yield.

$^1$H NMR (CDCl$_3$): δ ppm 0.9 (m, 6H), 1.04 (m, 1H), 1.17 (m, 2H), 1.37 (m, 7H), 1.69 (m, 1H), 2.01 (s, 3H), 2.02 (m, 1H), 2.08 (m, 1H), 2.37 (m, 1H), 2.84 (m, 1H), 3.52 (dd, J=15 and 7.5 HZ, 1H), 3.69 (s, 3H), 4.07 (m, 1H), 5.17 (d, J=10 Hz, 1H); IR (KBr): 3280, 2959, 2872, 2104, 1725, 1645, 1560, 1438, 1372 cm$^{-1}$; MS (ES+): 339.5 (100%, M+1).

| Analysis: | Calcd for C$_{17}$H$_{30}$N$_4$O$_3$: | C, 60.33; H, 8.93; N, 16.55 |
|---|---|---|
| | Found: | C, 60.60; H, 8.85; N, 16.31 |

EXAMPLE 73

(±) Methyl t-3-(1'-Acetylaminopentyl)-c-4-aminocyclopentan-r-1-carboxylate (80, Isomer-A at C-1', Scheme 9)

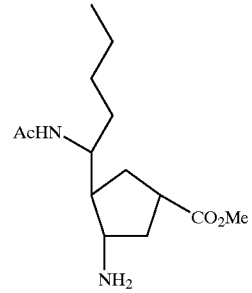

To a mixture of compound 76 (0.45 g, 1.5 mmol) in MeOH (10 mL) was added PtO$_2$ (50 mg) and the mixture was hydrogenated at 50 psi for 12 h. The catalyst was filtered off, washed with MeOH and the filtrate concentrated to dryness. The residue was purified using a column chromatography [silica gel, elution with EtOAc followed by a mixture of chloroform (80): methanol (18): ammonium hydroxide (2)] to give compound 78 (27%).

MS (ES+): 257.4 (M+1).

EXAMPLE 74

(±) Methyl t-3-(1'-Acetylaminopentyl)-c-4-aminocyclopentan-r-1-carboxylate (81, Isomer-B at C-1', Scheme 9)

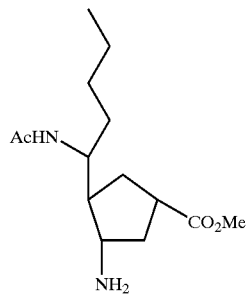

This was prepared from 77 (95 mg, 0.32 mmol) using the same procedure as for compound 80 in 65% yield, as hydrochloride.

$^1$H NMR (DMSO-d6): δ ppm 0.85 (t, 3H), 1.10–1.45 (m, 5H), 1.71–1.90 (m, 5H), 1.91 (s, 3H), 2.00–2.09 (m, 1H), 2.15–2.28 (m, 1H), 2.75–2.85 (m, 1H), 2.92–3.05 (m, 1H), 3.65 (s, 3H), 3.90–4.01 (m, 1H), 7.95–8.15 (m, 3H); MS (ES+): 271.4 (M+1); IR (KBr): 3400, 3240, 1733, 1645 cm$^{-1}$.

| Analysis: | Calcd for $C_{14}H_{26}N_2O_3$.HCl: | C, 54.80; H, 8.87; N, 9.11 |
|---|---|---|
| | Found: | C, 54.77; H, 8.80; N, 8.72 |

EXAMPLE 75

(±) Methy t-3-[(1'-Acetylamino-2'-ethyl)butyl]-c-4-aminocyclopentan-r-1-carboxylate (82, Isomer-B at C-1', Scheme 9)

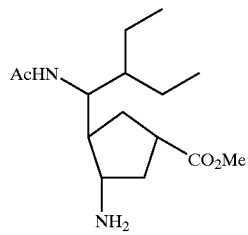

This was prepared from 78 (0.5 g, 1.6 mmol) using the same procedure as for compound 80 in 35% yield as white solid.

$^1$H NMR (DMSO-d6): δ ppm 0.75 (t, 3H, J=7.2 Hz), 0.8 (t, 3H, J=7.2 Hz), 1.2 (m, 2H), 1.3 (m, 1H), 1.4 (m, 2H), 1.8 (m, 3H), 1.9 (s, 3H), 2.2 (m, 2H), 2.9 (m, 2H), 3.6 (m, 3H), 3.8 (m, 1H), 8.0 (m, 3H).

EXAMPLE 76

(±) Methyl t-3-(1'-Acetylamino-2'-propyl)pentyl-c-4-aminocyclopentan-r-1-carboxylate (83, Isomer-B at C-1', Scheme 9)

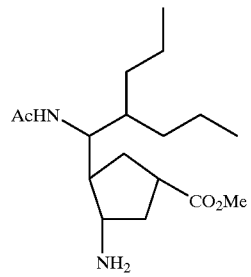

This was prepared from 79 (0.7 g, 2.1 mmol) using the same procedure as for compound 80 in 90% yield, as hydrochloride.

$^1$H NMR (DMSO-d6): δ ppm 0.85 (m, 6H), 1.26 (m, 8H), 1.4 (m, 1H), 1.77 (m, 2H), 1.84 (m, 1H), 1.88 (s, 3H), 2.20 (m, 2H), 2.83 (m, 1H), 2.92 (m, 1H), 3.61 (s, 3H), 3.83 (t, J=8.5 Hz, 1H), 7.92 (d, J=9 Hz, 1H), 7.98 (s, 2H); IR (KBr): 3321, 2958, 2933, 2872, 1725, 1641, 1614, 1368, 1166 cm$^{-1}$; MS (ES+): 313.4 (100%, M+1).

| Analysis: | Calcd for $C_{17}H_{32}N_2O_3$.HCl: | C, 58.52; H, 9.53; N, 8.03 |
|---|---|---|
| | Calcd. for $C_{17}H_{32}N_2O_3$.HCl.0.75H$_2$O: | C, 56.50; H, 9.34; N, 7.75 |
| | Found: | C, 56.33; H, 9.24; N, 7.48. |

EXAMPLE 77

(±) t-3-(1'-Acetylaminopentyl)-c-4-aminocyclopentan-r-1-carboxylic Acid (84, Isomer-A at C-1', Scheme 9)

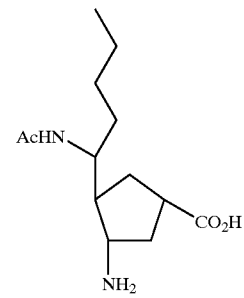

A mixture of compound 80 (4.6 mg, 0.0017 mmol), 1N sodium hydroxide (0.1 ml, 0.1 mmol), and water (0.2 ml) was stirred at room temperature for 2 h. The mixture was neutralized with 1N hydrochloric acid and diluted with water to yield the desired compound as 10.6 mmolar solution.

MS (ES+): 257.0 (M+1).

EXAMPLE 78

(±) t-3-(1'-Acetylaminopentyl)-c-4-aminocyclopentan-r-1-carboxylic Acid (85, Isomer-B at C-1', Scheme 9)

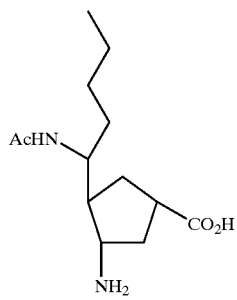

It was prepared from 81 (10.9 mg, 0.036 mmol) using the same procedure as for compound 84, as 35.4 mmolar solution.

MS (ES+): 257.3 (M+1).

EXAMPLE 79

(±) t-3-[(1'-Acetylamino-2'-ethyl)butyl]-c-4-aminocyclopentan-r-1-carboxylic Acid (86, Isomer-B at C-1', Scheme 9)

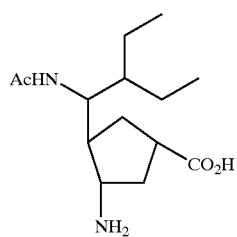

It was prepared from 82 (10 mg, 0.036 mmol) using the same procedure as for compound 84, as 35.9 mmolar solution.

MS (ES+): 271.4 (M+1).

EXAMPLE 80

(±) t-3-(1'-Acetylamino-2'-propyl)pentyl-c-4-aminocyclopentan-r-1-carboxylic Acid (87, Isomer-B at C-1', Scheme 9)

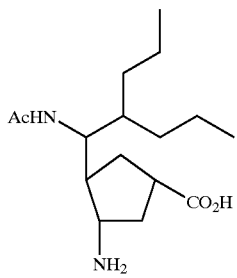

It was prepared from 83 (10.5 mg, 0.03 mmol) using the same procedure as for compound 84, as 13.4 mmolar solution.

MS (ES+): 299.4 (M+1).

EXAMPLE 81

(±) Methyl c-3-(1'-Acetylaminopentyl)-c-4-hydroxycyclopentan-r-1-carboxylate (88, Isomer-B at C-1', Scheme 10)

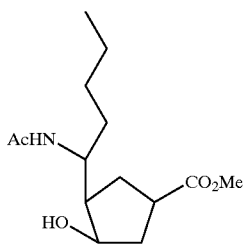

It was prepared from 45 (2.0 g, 8.9 mmol) in 88% yield using the same procedure as for compound 54. The product was re-crystallized from ether.

EXAMPLE 82

(±) c-3-(1'-Acetylaminopentyl)-c-4-hydroxycyclopentan-r-1-carboxylic Acid (89, Isomer-B at C-1', Scheme 10)

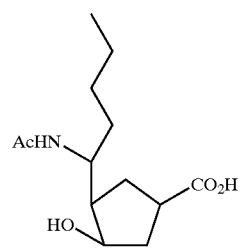

To a mixture of 88 (174 mg, 0.64 mmol) in THF/MeOH (4 mL, 1:1) was added 1N NaOH (1.6 mL, 1.6 mmol) and the mixture was stirred for 30 min. The solvent was removed, the residue was taken up in $H_2O$ (10 mL) and extracted with EtOAc (2×10 mL). The aqueous layer was acidified (pH 4), extracted with EtOAc (2×10 mL). The combined organic extracts from the acidic layer were dried ($MgSO_4$). After filtration, the filtrate was concentrated. The residue was triturated with ether/hexane to give the compound 89 in 69% yield, as white solid.

$^1$H NMR (DMSO-d6): δ ppm 0.85 (t, 3H), 1.13–1.28 (m, 5H), 1.51–1.87 (m, 5H), 1.75 (s, 3H), 1.98–2.07 (m, 1H), 2.52–2.68 (m, 1H), 3.75–3.84 (m, 1H), 3.89 (br s, 1H), 4.39 (br s, 1H), 7.41 (s, 1H), 11.90 (s, 1H); MS (ES+): 258.0 (M+1); IR (KBr): 3500–2850, 3529, 3318, 1700, 1601, 1565 $cm^{-1}$.

| Analysis: | Calcd for $C_{13}H_{23}NO_4$: | C, 60.68; H, 9.01; N, 5.44 |
|---|---|---|
| | Found: | C, 60.57; H, 8.95; N, 5.40 |

EXAMPLE 83

(±) Methyl c-3-(1'-Acetylaminopentyl)-c-4-methanesulfonyloxycyclopentan-r-1-carboxylate (90, Isomer-B at C-1', Scheme 10)

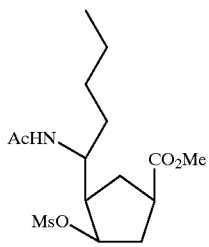

It was prepared from 88 (1.4 g, 5.16 mmol) in 20% yield using the same procedure as for compound 72.

$^1$H NMR (CDCl$_3$): δ 0.90 (t, 3H, J=6.5 Hz), 1.21–1.48 (m, 5H), 1.61–1.75 (m, 1H), 1.92–2.30 (m, 7H), 2.50 (dd, 1H, J=4.0 and 1.1 Hz), 2.81–2.95 (m, 1H), 3.09 (s, 3H), 3.68 (s, 3H), 4.02–4.15 (m, 1H), 5.10 (s, 1H), 5.45 (d, 8.7 Hz, 1H); IR (KBr) 3327, 1725, 1648 cm$^{-1}$; MS (ES+): 350.0 (M+1).

| Analysis: | Calc for C$_{15}$H$_{27}$NO$_6$S | C, 51.56; H, 7.79, N, 4.01 |
|---|---|---|
| | Found | C, 51.82; H, 7.84; N, 4.02 |

EXAMPLE 84

(±) Methyl-c-3-(1'-Acetylaminopentyl)-t-4-azidocyclopentan-r-1-carboxylate (91, Isomer-B at C-1', Scheme 10)

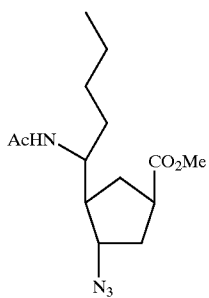

It was prepared from 90 (0.712 g, 2.04 mmol) in 68% yield using the same procedure as for compound 76.

EXAMPLE 85

(±) Methyl c-3-(1'-Acetylaminopentyl)-t-4-aminocyclopentan-r-1-carboxylate (92, Isomer-B at C-1', Scheme 10)

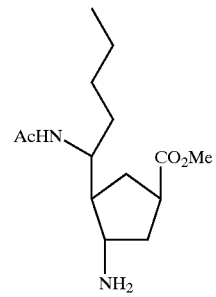

It was prepared from 91 (50 mg, 0.17 mmol) in 90% yield using the same procedure as for compound 80, and obtained as hydrochloride.

$^1$H NMR (DMSO-d6): δ ppm 0.85 (m, 3H), 1.3 (m, 6H), 1.5 (m, 1H), 1.8 (m, 4H), 2.1 (m, 3H), 3.1 (m, 2H), 3.6 (s, 3H), 4.0 (m, 1H), 7.9 (m, 1H), 8.2 (m, 3H); IR (KBr): 3249, 2955, 2933, 2871, 2361, 1732, 1645, 1548, 1437; MS (ES+): 271.0 (100%, M+1).

| Analysis: | Calcd for C$_{14}$H$_{26}$N$_2$O$_3$.HCl.0.7H$_2$O: | C, 52.71; H, 8.99; N, 8.78 |
|---|---|---|
| | Found: | C, 53.09; H, 8.59; N, 8.20. |

EXAMPLE 86

(±) c-3-(1'-Acetylaminopentyl)-t-4-aminocyclopentan-r-1-carboxylic Acid (93, Isomer-B at C-1', Scheme 10)

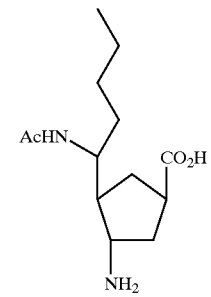

It was prepared from 92 (9.3 mg, 0.029 mmol) using the same procedure as for compound 84, as 28.5 mmolar solution.

MS (ES+): 257.0 (M+1).

EXAMPLE 87

(±) Methyl t-3-(1'-Acetylaminopentyl)-c-4-[(tert-butoxycarbonylamino-tert-butoxycarbonylimino)methyl]aminocyclopentan-r-1-carboxylate (94, Isomer-A at C-1', Scheme 11)

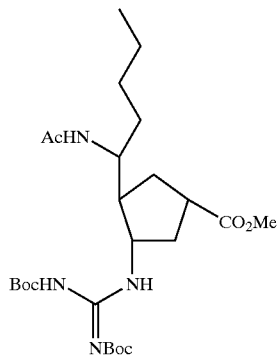

To a mixture of compound 80 (0.1 g, 0.38 mmol) in dry DMF (4 mL) were added Et$_3$N (0.19 mL, 1.32 mmol), 1,3-bis(tert-butoxycarbonyl)-2-methyl-2-thiopseudourea (0.42 g, 0.12 mmol) and HgCl$_2$ (0.11 g, 0.42 mmol). The reaction mixture was stirred at room temperature for 16 h. The mixture was diluted with EtOAc (20 mL) and filtered through Celite. The filtrate was washed with water, brine, and dried (MgSO$_4$). After filtration, the filtrate was concentrated in vacuo. The crude product was purified by flash column chromatography (silica gel, 60–70% EtOAc in hexane) to yield compound 94 in 34% yield, as colorless oil.

MS (ES+): 513.6 (M+1).

EXAMPLE 88

(±) Methyl t-4-(1'-Acetylaminopentyl)-c-4-[(tert-butoxycarbonylamino-tert-butoxycarbonylimino)methyl]aminocyclopentan-r-1-carboxylate (95, Isomer-B at C-1', Scheme 11)

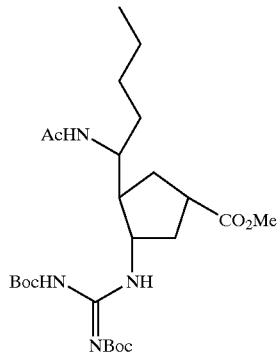

It was prepared from 81 (1.3 g, 4.81 mmol) in 64% yield using the same procedure as for compound 94, and obtained as white solid.

$^1$H NMR (CDCl$_3$): δ 0.90 (m, 3H), 1.4 (m, 6H), 1.48 (s, 9H), 1.50 (s, 9H), 1.71–1.85 (m, 1H), 1.88 (s, 3H), 2.15–2.30 (m, 3H), 2.75–2.85 (m, 1H), 3.70 (s, 3H), 3.91–4.00 (m, 1H), 4.42–4.51 (m, 1H), 7.10 (m, 1H), 8.25 (m, 1H), 11.30 (m, 1H); IR (KBr) 3323, 1721, 1716, 1612 cm$^{-1}$; MS (ES+):513.7(M+1)

| Analysis: | Calc for C$_{25}$H$_{44}$N$_4$O$_7$ | C, 58.57; H, 8.65; N, 10.93 |
| --- | --- | --- |
| | Found | C, 58.30; H, 8.57; N, 10.93 |

EXAMPLE 89

(±) Methy t-3-[(1'-Acetylamino-2'-ethyl)butyl]-c-4-[(tert-butoxycarbonylamino-tert-butoxycarbonylimino)methyl]aminocyclopentan-r-1-carboxylate (96, Isomer-B at C-1', Scheme 11)

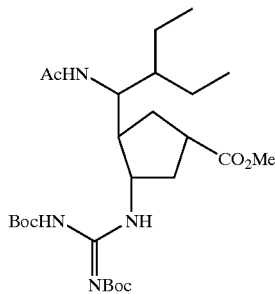

It was prepared from 82 (0.26 g, 1 mmol) in 50% yield using the same procedure as for compound 94 and obtained as white solid.

EXAMPLE 90

(±) Methyl t-3-(1'-Acetylamino-2'-propyl)pentyl-c-4-[(tert-butoxycarbonylamino-tert-butoxycarbonylimino)methyl]aminocyclopentan-r-1-carboxylate (97, Isomer-B at C-1', Scheme 11)

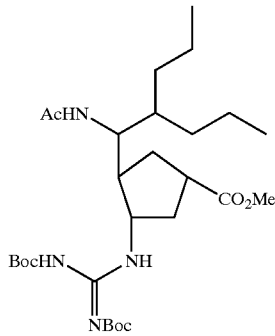

It was prepared from 83 (0.58 g, 1.87 mmol) in 91% yield as white solid using the same procedure as for compound 94.

$^1$H NMR (CDCl$_3$): δ ppm 0.88 (m, 6H), 0.97 (m, 1H), 1.10–1.46 (m, 7H), 1.48 (s, 9H), 1.49 (s, 9H), 1.70 (m, 1H), 1.83 (m, 2H), 1.97 (s, 3H), 2.06 (m, 1H), 2.13 (m 1H), 2.42 (m, 1H), 2.87 (m, 1H), 3.70 (s, 3H), 3.95 (m, 1H), 4.43 (m, 1H), 5.66 (d, J=9.9 Hz, 1H), 8.56 (d, J=8.6 Hz, 1H), 11.44 (s, 1H); IR (KBr): 3323, 2958, 2932, 2872, 1724, 1641, 1614, 1418, 1368, 1166, 1126, 1056 cm$^{-1}$; MS (ES+): 555.8 (100%, M+1).

| Analysis: | Calcd for $C_{28}H_{50}N_4O_7$: | C, 60.63; H, 9.09; N, 10.10 |
|---|---|---|
| | Found: | C, 60.69; H, 9.01; N, 10.10 |

EXAMPLE 91

(±) Methyl t-3-(1'-Acetylaminopentyl)-c-4-[(aminoimino)methyl]aminocyclopentan-r-1-carboxylate (98, Isomer-A at C-1', Scheme 11)

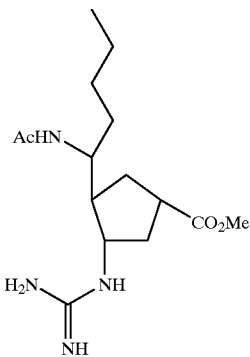

To a mixture of compound 94 (66 mg, 0.13 mmol) in $CH_2Cl_2$ (2 ml) was added trifluoroacetic acid (0.1 ml, 1.3 mmol). The reaction was stirred at room temperature for 16 h. The reaction mixture was then evaporated to dryness to yield compound 98 (63%) as a hygroscopic solid.

MS (ES+): 313.0 (100%, M+1)

| Analysis: | Calcd for | C, 47.88; H, 6.85; N, 13.14 |
|---|---|---|
| | $C_{15}H_{28}N_4O_3 \cdot CF_3COOH$: | |
| | Calcd for | C, 46.41; H, 6.99; N, 12.74 |
| | $C_{15}H_{28}N_4O_3 \cdot$ | |
| | $CF_3COOH \cdot 0.75 H_2O$: | |
| | Found: | C, 46.44; H, 6.88; N, 12.67 |

EXAMPLE 92

(±) Methyl t-3-(1'-Acetylaminopentyl)-c-4-[(aminoimino)methyl]aminocyclopentan-r-1-carboxylate (99, Isomer-B at C-1', Scheme 11)

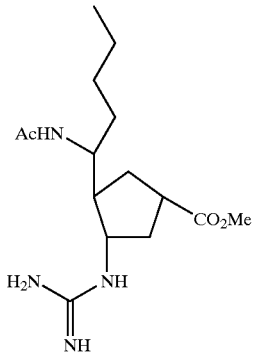

It was prepared from 95 (0.3 g, 0.59 mmol) in 89% yield as a white solid using the same procedure as for compound 98.

$^1$H NMR (DMSO-d6): δ ppm 0.80 (m, 3H), 1.2 (m, 6H), 1.5 (m, 1H), 1.8 (m, 6H), 2.2 (m, 1H), 2.7 (m, 1H), 3.5 (m, 1H), 3.6 (s, 3H), 3.8 (m, 1H), 7.0 (br s, 3H), 7.8 (m, 2H); IR (KBr) 3365, 3182, 2958, 2873, 1675, 1655, 1552 cm$^{-1}$; MS (ES+): 313 (100%, M+1).

| Analysis: | Calcd for | C, 46.84; H, 6.63; N, 12.62 |
|---|---|---|
| | $C_{15}H_{28}N_4O_3 \cdot 1.15\ CF_3CO_2H$: | |
| | Found: | C, 47.19; H, 6.83; N, 12.33 |

EXAMPLE 93

(±) Methyl t-3-[(1'-Acetylamino-2'-ethyl)butyl]-c-4-[(aminoimino)methyl]aminocyclopentan-r-1-carboxylate (100, Isomer-B at C-1', Scheme 11)

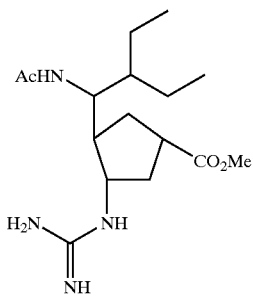

It was prepared from 96 (0.32 g, 0.55 mmol) in 85% yield as a white hygroscopic solid using the same procedure as for compound 98.

$^1$H NMR (DMSO-d6): δ ppm 0.80 (m, 6H), 1.3 (m, 5H), 1.6 (m, 1H), 1.8 (m, 2H), 1.9 (s, 3H), 2.2 (m, 2H), 2.7 (m, 1H), 3.4 (m, 1H), 3.6 (m, 3H), 3.8 (m, 1H), 7.0 (br s, 4H), 7.8 (m, 2H); MS (ES+): 327.5 (100%, M+1).

| Analysis: | Calcd for $C_{16}H_{30}N_4O_3 \cdot 0.75\ CF_3CO_2H$: | C, 47.40; H, 6.43; N, 11.34 |
|---|---|---|
| | Found: | C, 48.13; H, 6.94; N, 11.58 |

EXAMPLE 94

(±) t-3-(1'-Acetylamino-2'-propyl)pentyl-c-4-[(tert-butoxycarbonylamino-tert-butoxycarbonylimino)methyl]aminocyclopentan-r-1-carboxylic Acid (101, Isomer-B at C-1', Scheme 11)

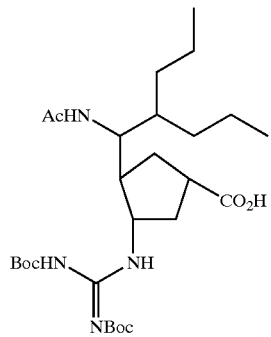

To a mixture of compound 97 (0.3 g, 0.54 mmol) in THF (5 mL) and MeOH (5 mL) was added 1 N NaOH (2.2 mL, 2.2 mmol). The reaction mixture was stirred at room temperature for 1 h and concentrated in vacuo to remove MeOH and THF. The aqueous layer was acidified with glacial AcOH and the solid obtained was collected by filtration, washed with water, hexane and dried in vacuo to furnish compound 101 in 87% yield, as white solid.

$^1$H NMR (DMSO-d6): δ ppm 0.80 (m, 6H), 0.95 (m, 2H), 1.06 (m, 2H), 1.28 (m, 5H), 1.37 (s, 9H), 1.46 (s, 9H), 1.58 (m, 1H), 1.70 (m, 1H), 1.78 (s, 3H), 1.93 (m, 1H), 2.16 (m, 2H), 2.70 (m, 1H), 3.81 (m, 1H), 4.19 (m, 1H), 7.35 (d, J=9.9 Hz, 1H), 8.42 (d, J=8.7 Hz, 1H), 11.48 (s, 1H), 12.19 (s, 1H); IR (KBr): 3317, 2958, 2933, 2872, 1724, 1641, 1614, 1418, 1368, 1156, 1127, 1056 cm$^{-1}$; MS (ES+): 541.7 (100%, M+1).

| Analysis: | Calcd for $C_{27}H_{48}N_4O_7$: | C, 59.97; H, 8.95; N, 10.36 |
|---|---|---|
| | Found: | C, 59.54; H, 8.81; N, 10.29 |

EXAMPLE 95

(±) t-3-(1'-Acetylaminopentyl)-c-4-[(aminoimino)methyl]aminocyclopentan-r-1-carboxylic Acid (102, Isomer-A at C-1', Scheme 11)

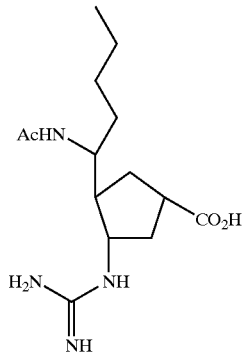

A mixture of compound 98 (4.2 mg, 0.0095 mmol), 1N sodium hydroxide (0.1 mL, 0.1 mmol), and water (0.2 mL) was stirred at room temperature for 2 h. The mixture was neutralized with 1N hydrochloric acid and diluted with water to yield compound 102 as 9.5 mmolar solution.

MS (ES+): 299.2 (M+1).

EXAMPLE 96

(±) t-3-(1'-Acetylaminopentyl)-c-4-[(aminoimino)methyl]aminocyclopentan-r-1-carboxylic Acid (103, Isomer-B at C-1', Scheme 11)

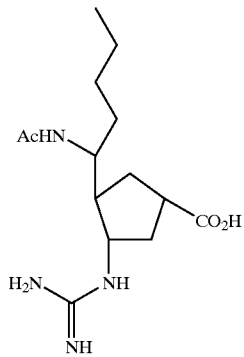

It was prepared from 99 (13 mg, 0.042 mmol) using the same procedure as for compound 102, as 19.5 mmolar solution.

MS (ES+): 299.2 (M+1).

EXAMPLE 97

(±) t-3-[(1'-Acetylamino-2'-ethyl)butyl]-c-4-[(aminoimino)methyl]aminocyclopentan-r-1-carboxylic Acid (104, Isomer-B at C-1', Scheme 11)

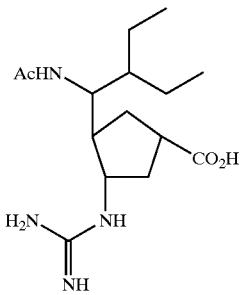

It was prepared from 100 (10.9 mg, 0.029 mmol) using the same procedure as for compound 102, as 33.4 mmolar solution.

MS (ES+): 313.4 (M+1).

EXAMPLE 98

(±) t-3-(1'-Acetylamino-2'-propyl)pentyl-c-4-[(aminoimino)methyl]aminocyclopentan-r-1-carboxylic Acid (105, Isomer-B at C-1', Scheme 11)

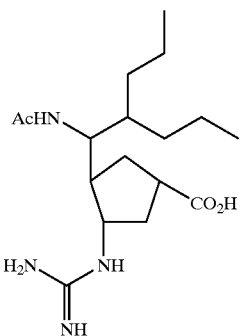

It was prepared from 101 (0.2 g, 0.37 mmol) using the same procedure as for compound 98. After trituration with ether, compound 105 was obtained as white solid in 65% yield.

$^1$H NMR (DMSO-d6): δ ppm 0.82 (m, 6H), 1.22 (m, 9H), 1.62 (m, 2H), 1.82 (m, 1H), 1.87 (s, 3H), 2.11 (m, 2H), 3.38 (m, 1H), 3.76 (m, 1H), 7.43 (br s, 4H), 7.67 (d, J=9.7 Hz, 1H), 8.43 (s, 1H), 12.5 (s, 1H); IR (KBr): 3318, 2959, 2933, 2872, 1724, 1641, 1615, 1419, 1369, 1156, 1126, 1056 cm$^{-1}$; MS (ES+): 341.5 (100%, M+1).

| Analysis: | | |
|---|---|---|
| Calcd for $C_{17}H_{32}N_4O_3 \cdot 0.5CF_3COOH$: | | C, 54.39; H, 8.24; N, 14.10 |
| Calcd for $C_{17}H_{32}N_4O_3 \cdot 0.5CF_3COOH \cdot 0.25H_2O$: | | C, 53.78; H, 8.27; N, 13.94 |
| Found: | | C, 53.89; H, 8.00; N, 13.92 |

EXAMPLE 99

(±) Methyl c-3-(1'-Acetylaminopentyl)-t-4-[(tert-butoxycarbonylamino-tert-butoxycarbonylimino)methyl]aminocyclopentan-r-1-carboxylate (106, Isomer-B at C-1', Scheme 12)

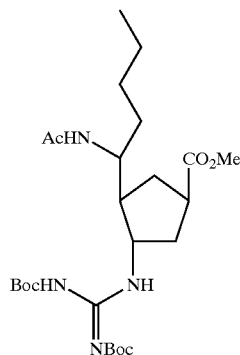

It was prepared from 92 (0.4 g, 1.48 mmol) using the same procedure as for compound 94, and was obtained in 60% yield, as white solid.

EXAMPLE 100

(±) Methyl c-3-(1'-Acetylaminopentyl)-t-4-[(aminoimino)methyl]aminocyclopentan-r-1-carboxylate (107, Isomer-B at C-1', Scheme 12)

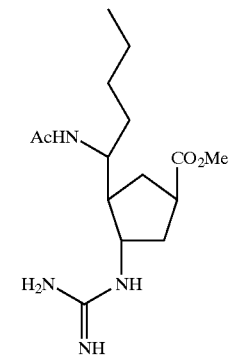

It was prepared from 106 (0.35 g, 0.68 mmol) using the same procedure as for compound 98, and was obtained in 80% yield as tan solid.

$^1$H NMR (DMSO-d6): δ ppm 0.80 (m, 3H), 1.3 (m, 6H), 1.6 (m, 2H), 1.8 (s, 3H), 1.9 (m, 2H), 2.1 (m, 1H), 2.9 (m, 1H), 3.5 (m, 1H), 3.6 (s, 3H), 3.9 (m, 2H), 7.2 (br s, 3H), 7.8 (m, 2H); MS (ES+): 313.1 (100%, M+1).

| Analysis: | Calcd for $C_{15}H_{28}N_4O_3 \cdot 1.15\ CF_3CO_2H$: | C, 46.84; H, 6.64; N, 12.62 |
|---|---|---|
| | Found: | C, 46.83; H, 6.74; N, 12.4 |

EXAMPLE 101

(±) c-3-(1-Acetylaminopentyl)-t-4-[(aminoimino)methyl]aminocyclopentan-r-1-carboxylic Acid (108, Isomer-B at C-1', Scheme 12)

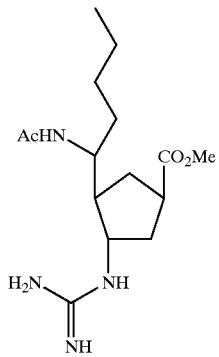

It was prepared from 107 (11 mg, 0.0248 mmol) using the same procedure as for compound 102, and was obtained as 24.8 mmolar solution.

MS (ES+): 299.5 (M+1).

EXAMPLE 102

(1S,4R)-(−)-4-Aminocyclopent-2-en-1-carboxylic Acid Hydrochloride (112, Scheme 13)

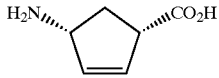

A mixture of (−)-(1R,4S)-2-azabicyclo[2.2.1]hept-5-en-3-one (109, 15 g, 137 mmol) and 1N HCl (375 mL) was heated at reflux for 1 h. The mixture was concentrated and the residue dried in vacuo to yield 112 in 95% yield. It was used as such for the next step.

EXAMPLE 103

(1R,4S)-(+)-4-Aminocyclopent-2-en-1-carboxylic Acid Hydrochloride (113, Scheme 13)

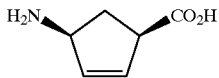

It was prepared from (+)-(1S,4R)-2-azabicyclo[2.2.1]hept-5-en-3-one (110, 4.9 g) according to the method used for compound 112.

EXAMPLE 104

(±)-cis-4-Aminocyclopent-2-en-1-carboxylic Acid Hydrochloride (114, Scheme 13)

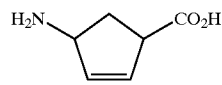

It was prepared from (±)-2-azabicyclo[2.2.1]hept-5-en-3-one (111, 3.2 g) according to the method used for compound 112.

EXAMPLE 105

(1S,4R)-(−)-Methyl-4-aminocyclopent-2-en-1-carboxylate Hydrochloride (115, Scheme 13)

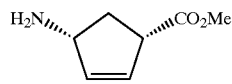

A mixture of (−)-(1R,4S)-2-azabicyclo[2.2.1]hept-5-en-3-one (109, 600 g, 5.51 mol) and 1N methanolic HCl (12 L) was heated at reflux for 10 h. The solvent was evaporated under reduced pressure and to the residue was added ether (800 mL), and cooled. The solid obtained was collected by filtration, washed with ether and dried to give 956 g (98%) of compound 115, as white crystalline solid, mp 106–108° C.

$^1$H NMR (DMSO-d$_6$): δ 1.98 (m, 1H), 2.52 (m, 1H), 3.6 (s, 3H), 3.68 (m, 1H), 4.15 (m 1H), 5.88 (d, 1H), 6.08 (d, 1H), 8.40 (m, 2H); MS (ES+): 142.11 (100%, M+1); IR (KBr): 3004, 1722, 1239, 1217 cm$^{-1}$.

| Analysis: | Calcd for C$_7$H$_9$NO$_3$: | C, 47.33; H, 6.81; N, 7.89 |
|---|---|---|
| | Found: | C, 47.12; H, 7.12; N, 7.85 |

EXAMPLE 106

(1S,4R)-(−)-Ethyl-4-aminocyclopent-2-en-1-carboxylate Hydrochloride (116, Scheme 13)

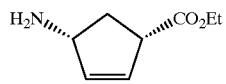

Method A:

It was prepared from (−)-(1R,4S)-2-azabicyclo[2.2.1]hept-5-en-3-one (109, 4.9 g) and ethanolic HCl according to the method used for compound 115.

Method B:

It was also prepared from compound 112 and ethanoil HCl according to the method used for compound 115.

EXAMPLE 107

(1R,4S)-(+)-Ethyl-4-aminocyclopent-2-en-1-carboxylate Hydrochloride (117, Scheme 13)

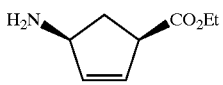

It was prepared from compound 113 (7.3 g) according to the method-B used for compound 116.

EXAMPLE 108

(±)-cis-Methyl-4-aminocyclopent-2-en-1-carboxylate Hydrochloride (118, Scheme 13)

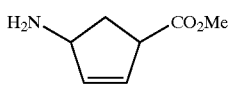

It was prepared from (±)-2-azabicyclo[2.2.1]hept-5-en-3-one (111, 11.2 g) and methanolic HCl according to the method used for compound 115.

EXAMPLE 109

(±)-cis-Ethyl-4-aminocyclopent-2-en-1-carboxylate Hydrochloride (119, Scheme 13)

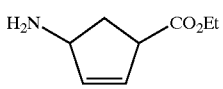

It was prepared from 114 (4.9 g) and ethanolic HCl according to the method-B used for compound 116.

EXAMPLE 110

(1S,4R)-(−)-Methyl-4-tert-butoxycarbonylaminocyclopent-2-en-1-carboxylate (120, Scheme 13)

To a mixture of compound 115 (950 g, 5.35 mol) and di-tert-butyldicarbonate (1226 g, 5.62 mol) in dichloromethane (12 L) at 0° C. was added triethylamine over a period of 2.5 h and the reaction mixture further stirred for 1 h. The reaction mixture was washed with water (2×8 L) and brine (2×4 L) and the organic layer separated and dried over MgSO$_4$. After filtration, the filtrate was concentrated and the residual thick syrup was crystallized from hexane to give 1196 g (92%) of compound 120 in 3 crops.

$^1$H NMR (CDCl$_3$): δ 1.44 (s, 9H), 1.85 (m, 1H), 2.51 (m, 1H), 3.47 (m, 1H), 3.71 (s, 3H), 4.78 (m, 1H), 4.88 (br s, 1H), 5.86 (m, 2H); MS (ES+): 242.25 (80%, M+1).

| Analysis: | Calcd for C$_{12}$H$_{19}$NO$_4$: | C, 59.73; H, 7.94; N, 5.80 |
|---|---|---|
|  | Found: | C, 59.57; H, 7.86; N, 5.79 |

EXAMPLE 111

(1S,4R)-(−)-Ethyl-4-tert-butoxycarbonylaminocyclopent-2-en-1-carboxylate (121, Scheme 13)

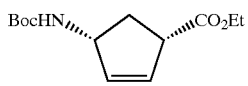

It was prepared from 116 (17.5 g) according to the method used for compound 120.

EXAMPLE 112

(1R,4S)-(+)-Ethyl-4-tert-butoxycarbonylaminocyclopent-2-en-1-carboxylate (122, Scheme 13)

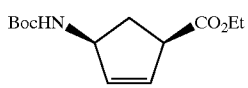

It was prepared from 117 (8.4 g) according to the method used for compound 120.

EXAMPLE 113

(±)-cis-Methyl-4-tert-butoxycarbonylaminocyclopent-2-en-1-carboxylate (123, Scheme 13)

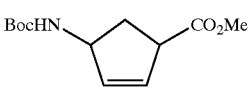

It was prepared from 118 (17.8 g) according to the method used for compound 120.

EXAMPLE 114

(±)-cis-Ethyl-4-tert-butoxycarbonylaminocyclopent-2-en-1-carboxylate (124, Scheme 13)

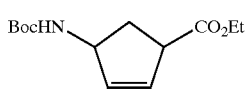

It was prepared from 119 (20.8 g) according to the method used for compound 120.

EXAMPLE 115

(3aR,4R,6S,6aS)-(+)-Methyl-4-tert-butoxycarbonylamino-3-(1'-ethylpropyl)-4,5,6,6a-tetrahydro-3aH-cyclopent[d]isoxazole-6-carboxylate
(125, Scheme 13)

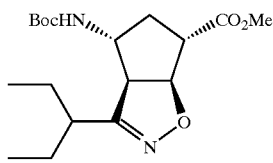

Method-A:

A mixture of 120 (949 g, 3.93 mol) and phenyl isocyanate (1.5 L, 13.8 mol) in benzene (10 L) was heated under reflux. To this mixture was added, a mixture of 2-ethyl-1-nitrobutane (918 g, 5.92 mol, 85% pure by $^1$H NMR) and triethylamine (55 mL, 0.40 mol) in benzene (2 L) over a period of 5 h. The reaction mixture was further stirred under reflux for 24 h. On cooling, the solids were removed by filtration, the filtrate was concentrated and to the residue was added ethyl ether (2 L). The mixture was allowed to stand overnight, the solids were again removed by filtration and the filtrate was concentrated in vacuo to give 1.991 Kg of a dark brown syrup.

The product obtained above was dissolved in THF (5.0 L) and ethanol (7.5 L). To this mixture was added, NaOH (454 g in 5 L cold water) and the mixture stirred at room temperature for 3 h. The mixture was then concentrated in vacuo. The residue was dissolved in water (10 L), extracted with ethyl ether (2×2 L) and the organic layers were discarded. The aqueous layer was acidified with acetic acid and extracted with ethyl acetate (2×7 L). The combined organic extracts were dried (MgSO$_4$) and the organic layer concentrated to give 1.75 Kg of the crude acid.

To the above product in methanol (19.5 L) was added conc. HCl (162 mL) and the mixture stirred at room temperature for 16 h. The mixture was neutralized with ammonium hydroxide and the solvent evaporated in vacuo to give 1.422 Kg of the crude ester. The crude product was dissolved in ethyl acetate (5 L), washed with water (5 L) and brine (5 L), and dried (MgSO$_4$). After filtration, the filtrate was concentrated and the residue was purified by passing through a column of silica gel using hexane/ethyl acetate (95/5 to 85/15) mixture as the eluent. The appropriate fractions were pooled together and concentrated to give 984 g (70.5%) of 125, mp 66° C.

| Analysis: | Calcd for C$_{18}$H$_{30}$N$_2$O$_5$: | C, 61.00; H, 8.53; N, 7.90 |
|---|---|---|
| | Found: | C, 61.13; H, 8.45; N, 7.84 |

$^1$H NMR (CDCl$_3$): δ ppm 0.87–0.95 (m, 6H), 1.44 (s, 9H), 1.58–1.78 (m, 4H), 2.0–2.15 (m, 2H), 2.51 (b s, 1H), 3.21 (d, J=8.1 Hz, 1H), 3.58 (d, J=8.8 Hz, 1H), 3.76 (s, 3H), 4.23 (b s, 1H), 5.21 (d, 1H, J=8.8 Hz), 5.59 (b s, 1H); MS (ES+): 355.64 (M+1).

Method-B:

The reaction of cyclopentene compound 120 with 1-nitro-2-ethylbutane and phenyl isocyanate was done the same way as described in method-A. After the reaction was complete (24 h reflux), the solids were removed by filtration, and the filtrate was concentrated. The residue was purified two times by passing through a silica gel column using ethyl acetate: hexane mixture as eluent.

Method-C:

A mixture of 120 (1.08 Kg, 4.46 mol) and 2-ethylbutyrohydroximinoyl chloride (prepared from 2-ethylbutyraldoxime and N-chlorosuccinimide, 614 g, 4.1 mol) in THF (8 L) was heated at reflux. To this mixture was added a mixture of triethylamine (340 mL, 2.4 mol) in THF over a period of 1.5 h. Additional amount of chloro-oxime (550 g, 3.7 mol) was added followed by a mixture of triethylamine (340 mL, 2.4 mol) in THF (340 mL) over 1 h period. This exact addition was repeated twice. Additional triethylamine (100 mL, 0.7 mol) was added in 30 min. The reaction mixture was further heated at reflux for 16 h. The reaction mixture was cooled and the insoluble solid was removed by filtration. The filtrate was concentrated and the residue was purified either by chromatography or through acid-base treatment as described in methods A and B.

EXAMPLE 116

(3aR,4R,6S,6aS)-(+)-Methyl-4-tert-butoxycarbonylamino-3-(1'-propylbutyl)-4,5,6,6a-tetrahydro-3aH-cyclopent[d]isoxazole-6-carboxylate
(126, Scheme 13)

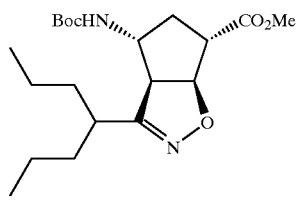

It was prepared from 120 (171 g) using the same procedure as for compound 125 (method-A).

EXAMPLE 117

(3aR,4R,6S,6aS)-(+)-Ethyl-4-tert-butoxycarbonylamino-3-(1'-ethylpropyl)-4,5,6,6a-tetrahydro-3aH-cyclopent[d]isoxazole-6-carboxylate
(127, Scheme 13)

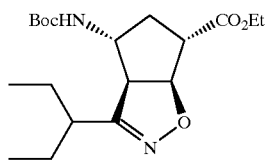

It was prepared from 121 (5.64 g) using the same procedure as for compound 125 (method-B).

EXAMPLE 118

(3aR,4R,6S,6aS)-(+)-Ethyl-4-tert-butoxycarbonylamino-3-(1'-propylbutyl)-4,5,6,6a-tetrahydro-3aH-cyclopent[d]isoxazole-6-carboxylate (128, Scheme 13)

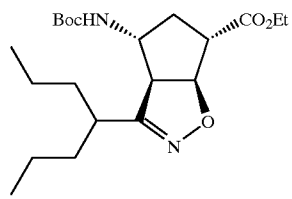

It was prepared from 121 (16.1 g) using the same procedure as for compound 125 (method-B).

EXAMPLE 119

(3aS,4S,6R,6aR)-(−)-Ethyl-4-tert-butoxycarbonylamino-3-(1'-ethylpropyl)-4,5,6,6a-tetrahydro-3aH-cyclopent[d]isoxazole-6-carboxylate (129, Scheme 13)

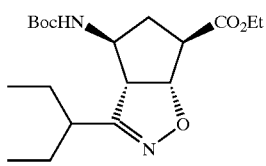

It was prepared from 122 (5.1 g) using the same procedure as for compound 125 (method-B).

EXAMPLE 120

(±)-Methyl-4-tert-butoxycarbonylamino-3-(1'-ethylpropyl)-4,5,6,6a-tetrahydro-3aH-cyclopent[d]isoxazole-6-carboxylate (NHBoc and Ester Groups cis to Each Other but trans to Isooxazoline Ring, 130, Scheme 13)

It was prepared from 123 (4.8 g) using the same procedure as for compound 125 (method-B).

EXAMPLE 121

(±)-Methyl-4-tert-butoxycarbonylamino-3-(1'-propylbutyl)-4,5,6,6a-tetrahydro-3aH-cyclopent[d]isoxazole-6-carboxylate (NHBoc and Ester Groups cis to Each Other but trans to Isooxazoline Ring, 131, Scheme 13)

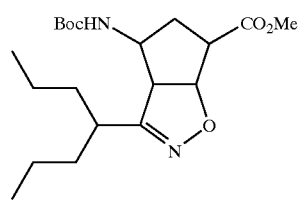

It was prepared from 123 (4.0 g) using the same procedure as for compound 125 (method-B).

EXAMPLE 122

(±)-Methyl-4-tert-butoxycarbonylamino-3-(2'-ethylbutyl)-4,5,6,6a-tetrahydro-3aH-cyclopent[d]isoxazole-6-carboxylate (NHBoc and Ester Groups cis to Each Other but trans to Isooxazoline Ring, 132, Scheme 13)

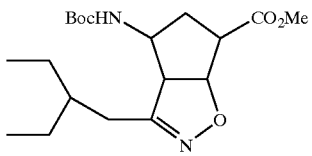

It was prepared from 123 (1.18 g) using the same procedure as for compound 125 (method-B).

EXAMPLE 123

(±)-Methyl-4-tert-butoxycarbonylamino-3-(n-butyl)-4,5,6,6a-tetrahydro-3aH-cyclopent[d]isoxazole-6-carboxylate (NHBoc and Ester Groups cis to Each Other but trans to Isooxazoline Ring, 133, Scheme 13)

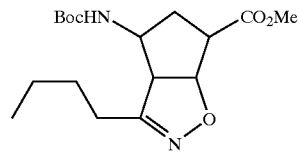

It was prepared from 123 (1.2 g) using the same procedure as for compound 125 (method-B).

EXAMPLE 124

(±)-Ethyl-4-tert-butoxycarbonylamino-3-(1'-ethylpropyl)-4,5,6,6a-tetrahydro-3aH-cyclopent[d]isoxazole-6-carboxylate (NHBoc and Ester Groups cis to Each Other but trans to Isooxazoline Ring, 134, Scheme 13)

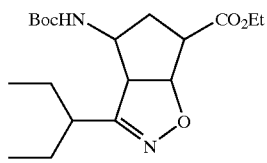

It was prepared from 124 (4.8 g) using the same procedure as for compound 125 (method-B).

EXAMPLE 125

(±)-Ethyl-4-tert-butoxycarbonylamino-3-(1'-methylpropyl)-4,5,6,6a-tetrahydro-3aH-cyclopent[d]isoxazole-6-carboxylate (Mixture at C-1', NHBoc and Ester Groups cis to Each Other but trans to Isooxazoline Ring, 135, Scheme 13)

It was prepared from 124 (3.5 g) using the same procedure as for compound 125 (method-B).

EXAMPLE 126

(±)-Ethyl-4-tert-butoxycarbonylamino-3-(1'-methylethyl)-4,5,6,6a-tetrahydro-3aH-cyclopent[d]isoxazole-6-carboxylate (NHBoc and Ester Groups cis to Each Other but trans to Isooxazoline Ring, 136, Scheme 13)

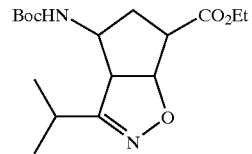

It was prepared from 124 (2.9 g) using the same procedure as for compound 125 (method-B).

EXAMPLE 127

(1S,2S,3R,4R,1'S)-(−)-Methyl 3-(1'-Acetylamino-2'-ethyl)butyl-4-tert-butoxycarbonylamino-2-hydroxycyclopentan-1-carboxylate (137, Scheme-14)

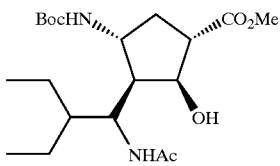

To a mixture of 125 (80 g, 0.226 mol) in methanol (1.6 L) were added conc. HCl (18.8 mL, 0.226 mol) and Adam's catalyst ($PtO_2$, 8.0 g) and the mixture was stirred very vigorously at 100 psi hydrogen pressure for 4 h. The catalyst was removed by filtration and the filtrate concentrated to give 82.7 g (93%) of (1S,2S,3R,4R,1'S)-(−)-Methyl 3-(1'-amino-2'-ethyl)butyl-4-tert-butoxycarbonyl-amino-2-hydroxycyclopentan-1-carboxylate, which was used as such for acetylation.

To the above obtained amine hydrochloride (66.2 g, 0.168 mol) in dichloromethane (600 mL), were added triethylamine (23.4 mL, 0.168 mol) and acetic anhydride (17.5 mL, 0.184 mol) at room temperature and stirred for 2 h. The reaction mixture was washed with water (600 mL). Water layer was back extracted with dichloromethane (200 mL). The combined organic layers were washed with water (300 mL) and brine (300 mL), and dried over magnesium sulfate. After filtration, the filtrate was concentrated and the residue purified by passing through a column of silica gel using hexane/ethyl acetate (1:1) as an eluent. The appropriate fractions were pooled together and concentrated to give 45 g (67%) of compound 137.

| Analysis: | Calcd for $C_{20}H_{36}N_2O_6$: | C, 59.98; H, 9.06; N, 6.99 |
|---|---|---|
| | Found: | C, 59.89; H, 8.91; N, 6.94 |

$^1$H NMR ($CDCl_3$): δ ppm 0.77–0.87 (m, 6H), 1.19–1.44 (m, 15H), 1.66–1.72 (m, 1H), 1.96–2.00 (m, 1H), 2.08 (s, 3H), 2.45–2.53 (m, 1H), 2.80–2.84 (m, 1H), 3.70 (s, 3H), 3.99–4.04 (m, 1H), 4.11–4.15 (m, 1H), 4.23 (d, J=5.2 Hz, 1H), 4.78 (d, J=9.3 Hz, 1H), 7.55 (d, J=10.0 Hz, 1H); MS (ES+): 401.75 (M+1).

EXAMPLE 128

(1S,2S,3R,4R,1'S)-(−)-Methyl 3-(1'-Acetylamino-2'-propyl)pentyl-4-tert-butoxycarbonyl-amino-2-hydroxycyclopentan-1-carboxylate (138, Scheme-14)

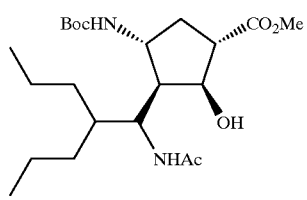

It was prepared from 126 (77 g) using the same procedure as for compound 137.

EXAMPLE 129

(1S,2S,3R,4R,1'S)-(−)-Ethyl 3-(1'-Acetylamino-2'-ethyl)butyl-4-tert-butoxycarbonyl-amino-2-hydroxycyclopentan-1-carboxylate (139, Scheme-14)

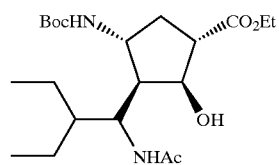

It was prepared from 127 (5 g) using the same procedure as for compound 137.

EXAMPLE 130

(1S,2S,3R,4R,1'S)-(−)-Methyl 3-(1'-Acetylamino-2'-propyl)pentyl-4-tert-butoxycarbonyl-amino-2-hydroxycyclopentan-1-carboxylate (140, Scheme-14)

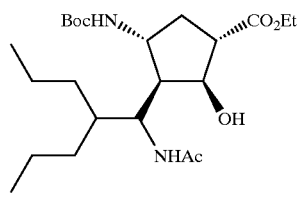

It was prepared from 128 (15 g) using the same procedure as for compound 137.

EXAMPLE 131

(1R,2R,3S,4S,1'R)-(+)-Ethyl 3-(1'-Acetylamino-2'-ethyl)butyl-4-tert-butoxycarbonyl-amino-2-hydroxycyclopentan-1-carboxylate (141, Scheme-14)

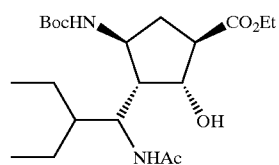

It was prepared from 129 (5.9 g) using the same procedure as for compound 137.

EXAMPLE 132

(±)-Methyl t-3-(1'-Acetylamino-2'-ethyl)butyl-c-4-tert-butoxycarbonylamino-t-2-hydroxycyclopentan-r-1-carboxylate (142, Isomer-A at C-1', Scheme-14)

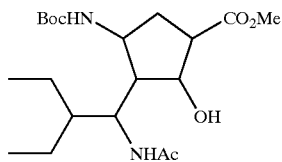

It was prepared from 130 (2.6 g) using the same procedure as for compound 137.

EXAMPLE 133

(±)-Methyl t-3-(1'-Acetylamino-2'-propyl)pentyl-c-4-tert-butoxycarbonylamino-t-2-hydroxycyclopentan-r-1-carboxylate (143, Isomer-A at C-1', Scheme-14)

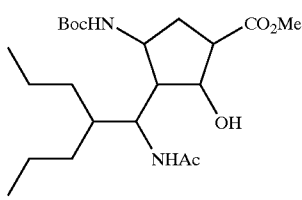

It was prepared from 131 (6.2 g) using the same procedure as for compound 137.

EXAMPLE 134

(±)-Methyl t-3-(1'-Acetylamino-3'-ethyl)pentyl-c-4-tert-butoxycarbonylamino-t-2-acetyloxycyclopentan-r-1-carboxylate (144, Isomer-A at C-1', Scheme-14)

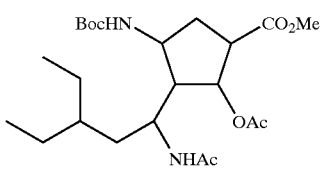

It was prepared from 132 (2.4 g) using the same procedure as for compound 137, except that during acetylation, excess of acetic anhydride (2.5 equivalent) and triethylamine (2.5 equivalent) were used.

EXAMPLE 135

(±)-Methyl t-3-(1'-Acetylamino-n-butyl)-c-4-tert-butoxycarbonylamino-t-2-acetyloxy-cyclopentan-r-1-carboxylate (145, Isomer-A at C-1', Scheme-14)

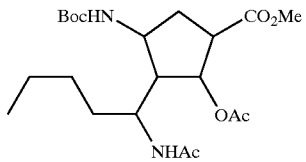

It was prepared from 133 (0.45 g) using the same procedure as for compound 137, except that during acetylation, excess of acetic anhydride (2.5 equivalent) and triethylamine (2.5 equivalent) were used.

EXAMPLE 136

(±)-Ethyl t-3-(1'-Acetylamino-2'-ethyl)butyl-c-4-tert-butoxycarbonylamino-t-2-hydroxycyclopentan-r-1-carboxylate (146, Isomer-A at C-1', Scheme-14)

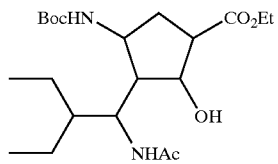

It was prepared from 134 (2.6 g) using the same procedure as for compound 137.

EXAMPLE 137

(±)-Ethyl t-3-(1'-Acetylamino-2'-methyl)butyl-c-4-tert-butoxycarbonylamino-t-2-hydroxycyclopentan-r-1-carboxylate (147, Isomer-A at C-1', Mixture at C-2', Scheme-14)

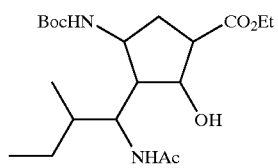

It was prepared from 135 (1.3 g) using the same procedure as for compound 137.

EXAMPLE 138

(±)-Ethyl t-3-(1'-Acetylamino-2'-methyl)propyl-c-4-tert-butoxycarbonylamino-t-2-hydroxycyclopentan-r-1-carboxylate (148, Isomer-A at C-1', Scheme-14)

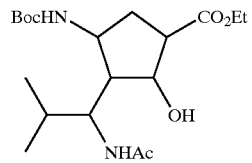

It was prepared from 136 (1.39 g) using the same procedure as for compound 137.

EXAMPLE 139

(1S,2S,3R,4R,1'S)-(−)-Methyl 3-(1'-Acetylamino-2'-ethyl)butyl-4-amino-2-hydroxy-cyclopentan-1-carboxylate Hydrochloride (149, Scheme-14)

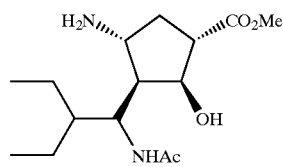

To a mixture of 137 (150 g, 0.375 mol) in ether (800 mL) was added 1N HCl in ether (1170 mL, 1.17 mol) and stirred at room temperature for 24 h and then heated at reflux for 2 h. After cooling, the solid was collected by filtration, washed with ether and dried in vacuo to give 126 g of 149. This was used as such for the next step.

EXAMPLE 140

(1S,2S,3R,4R,1'S)-(−)-Methyl 3-(1'-Acetylamino-2'-propyl)pentyl-4-amino-2-hydroxycyclopentan-1-carboxylate Hydrochloride (150, Scheme-14)

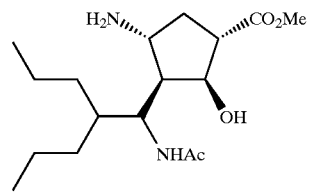

It was prepared from 138 (10.4 g) using the same procedure as for compound 149.

EXAMPLE 141

(1S,2S,3R,4R,1'S)-(−)-Ethyl 3-(1'-Acetylamino-2'-ethyl)butyl-4-amino-2-hydroxycyclo-pentan-1-carboxylate Trifluoroacetate (151, Scheme-14)

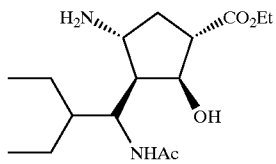

To a mixture of 139 (1.3 g, 3.14 mmol) in dichloromethane (20 mL) was added trifluoroacetic acid (4.0 mL) and stirred at room temperature for 6 h. It was concentrated and co-evaporated 2 times with dichloromethane and 2 times with ether. The residue was dried in vacuo to give 151, which was used as such for the next step.

EXAMPLE 142

(1R,2R,3S,4S,1'R)-(+)-Ethyl 3-(1'-Acetylamino-2'-ethyl)butyl-4-amino-2-hydroxy-cyclopentan-1-carboxylate Trifluoroacetate (152, Scheme-14)

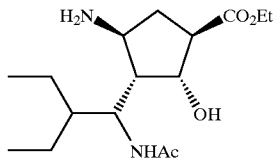

It was prepared from 141 (0.6 g) using the same procedure as for compound 151.

EXAMPLE 143

(±)-Methyl t-3-(1'-Acetylamino-2'-ethyl)butyl-c-4-amino-t-2-hydroxycyclopentan-r-1-carboxylate Trifluoroacetate (153, Isomer-A at C-1', Scheme-14)

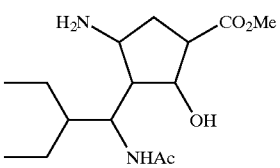

It was prepared from 142 (0.8 g) using the same procedure as for compound 151.

EXAMPLE 144

(±)-Methyl t-3-(1'-Acetylamino-2'-propyl)pentyl-c-4-amino-t-2-hydroxycyclopentan-r-1-carboxylate Trifluoroacetate (154, Isomer-A at C-1', Scheme-14)

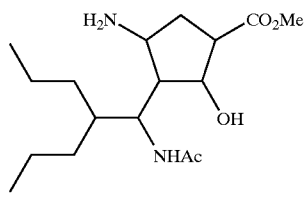

It was prepared from 143 (0.39 g) using the same procedure as for compound 151.

EXAMPLE 145

(±)-Methyl t-3-(1'-Acetylamino-3'-ethyl)pentyl-c-4-amino-t-2-acetyloxycyclopentan-r-1-carboxylate Trifluoroacetate (155, Isomer-A at C-1', Scheme-14)

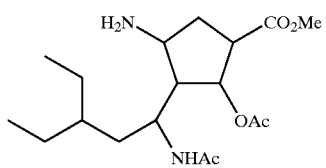

It was prepared from 144 (0.47 g) using the same procedure as for compound 151.

EXAMPLE 146

(±)-Methyl t-3-(1'-Acetylamino-n-butyl)-c-4-amino-t-2-acetyloxycyclopentan-r-1-carboxylate Trifluoroacetate (156, Isomer-A at C-1', Scheme-14)

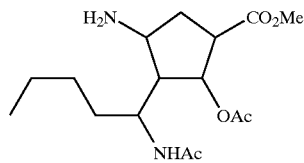

It was prepared from 145 (0.27 g) using the same procedure as for compound 151.

EXAMPLE 147

(±)-Ethyl t-3-(1'-Acetylamino-2'-ethyl)butyl-c-4-amino-t-2-hydroxycyclopentan-r-1-carboxylate Trifluoroacetate (157, Isomer-A at C-1', Scheme-14)

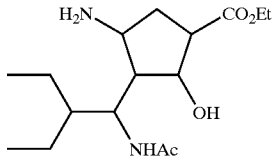

It was prepared from 146 (0.8 g) using the same procedure as for compound 151.

EXAMPLE 148

(±)-Ethyl t-3-(1'-Acetylamino-2'-methyl)butyl-c-4-amino-t-2-hydroxycyclopentan-r-1-carboxylate Trifluoroacetate (158, Isomer-A at C-1', Mixture at C-2', Scheme-14)

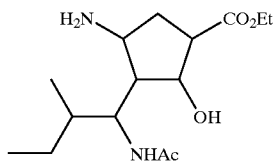

It was prepared from 147 (0.74 g) using the same procedure as for compound 151.

EXAMPLE 149

(±)-Ethyl t-3-(1'-Acetylamino-2'-methyl)propyl-c-4-amino-t-2-hydroxycyclopentan-r-1-carboxylate Trifluoroacetate (159, Isomer-A at C-1', Scheme-14)

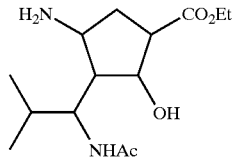

It was prepared from 148 (1.0 g) using the same procedure as for compound 151.

EXAMPLE 150

(1S,2S,3R,4R,1'S)-(−)-3-(1'-Acetylamino-2'-ethyl)butyl-4-amino-2-hydroxycyclopentan-1-carboxylic Acid (160, Scheme-14)

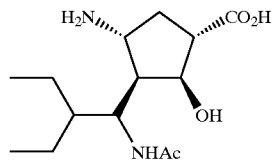

A mixture of 151 (14 mg, 0.0327 mmol) in 1N NaOH (0.1 mL) and water (0.2 mL) was stirred at room temperature for 2 h. The reaction mixture was neutralized with 1N HCl and diluted with water to give 32.7 mmolar solution.

MS (ES+): 287.4 (100%, M+1).

EXAMPLE 151

(1R,2R,3S,4S,1'R)-(+)-3-(1'-Acetylamino-2'-ethyl)butyl-4-amino-2-hydroxycyclopentan-1-carboxylic Acid (161, Scheme-14)

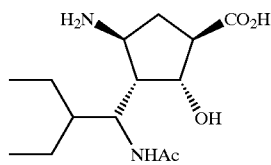

It was prepared from 152 (100 mg, 0.234 mmol) using the same procedure as for compound 160 and was obtained as 93.6 mmolar solution.

MS (ES+): 287.4 (100%, M+1).

EXAMPLE 152

(±)-t-3-(1'-Acetylamino-2'-ethyl)butyl-c-4-amino-t-2-hydroxycyclopentan-r-1-carboxylic Acid (162, Isomer-A at C-1', Scheme-14)

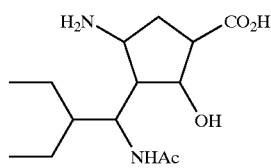

It was prepared from 153 (12.5 mg, 0.030 mmol) using the same procedure as for compound 160 and was obtained as 30.0 mmolar solution.

MS (ES+): 287.4 (100%, M+1).

EXAMPLE 153

(±)-t-3 -(1'-Acetylamino-2'-propyl)pentyl-c-4-amino-t-2-hydroxycyclopentan-r-1-carboxylic Acid (163, Isomer-A at C-1', Scheme-14)

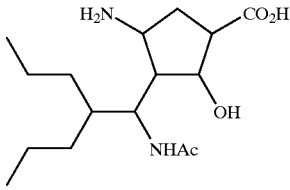

It was prepared from 154 (7.5 mg, 0.017 mmol) using the same procedure as for compound 160 and was obtained as 7.7 mmolar solution.

MS (ES+): 315.5 (100%, M+1).

EXAMPLE 154

(±)-t-3-(1'-Acetylamino-3'-ethyl)pentyl-c-4-amino-
t-2-hydroxycyclopentan-r-1-carboxylic Acid (164,
Isomer-A at C-1', Scheme-14)

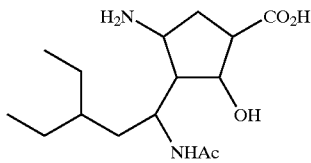

It was prepared from 155 (10.6 mg, 0.0225 mmol) using the same procedure as for compound 160 and was obtained as 21.5 mmolar solution.

MS (ES+): 301.4 (100%, M+1).

EXAMPLE 155

(±)-t-3-(1'-Acetylamino-n-butyl)-c-4-amino-t-2-
hydroxycyclopentan-r-1-carboxylic Acid (165,
Isomer-A at C-1', Scheme-14)

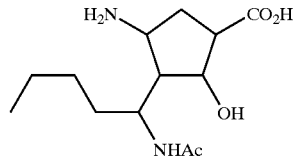

It was prepared from 156 (5.0 mg, 0.011 mmol) using the same procedure as for compound 160 and was obtained as 11.0 mmolar solution.

MS (ES+): 273.0 (100%, M+1).

EXAMPLE 156

(±)-t-3-(1'-Acetylamino-2'-methyl)butyl-c-4-amino-
t-2-hydroxycyclopentan-r-1-carboxylic Acid (166,
Isomer-A at C-1', Mixture at C-2', Scheme-14)

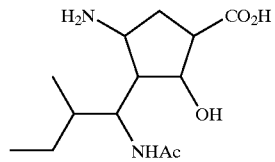

It was prepared from 158 (9.5 mg, 0.0229 mmol) using the same procedure as for compound 160 and was obtained as 9.36 mmolar solution.

MS (ES+): 273.5 (100%, M+1).

EXAMPLE 157

(±)-t-3-(1'-Acetylamino-2'-methyl)propyl-c-4-
amino-t-2-hydroxycyclopentan-r-1-carboxylic Acid
(167, Isomer-A at C-1', Scheme-14)

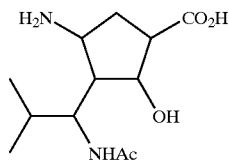

It was prepared from 159 (9.5 mg, 0.0237 mmol) using the same procedure as for compound 160 and was obtained as 12.9 mmolar solution.

MS (ES+): 259.4 (100%, M+1).

EXAMPLE 158

(1S,2S,3R,4R,1'S)-(−)-Ethyl 3-(1'-Acetylamino-2'-
ethyl)butyl-4-[(tert-butoxycarbonyl-amino-tert-
butoxycarbonylimino)methyl]amino-2-
hydroxycyclopentan-1-carboxylate (168, Scheme-
15)

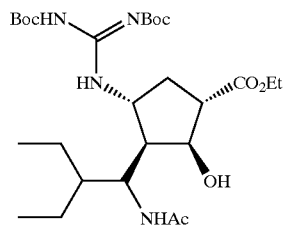

It was prepared from 151 (0.65 g) using the same procedure as for compound 94.

EXAMPLE 159

(±)-Methyl t-3-(1'-Acetylamino-2'-ethyl)butyl-c-4-
[(tert-butoxycarbonylamino-tert-
butoxycarbonylimino)methyl]amino-t-2-
hydroxycyclopentan-r-1-carboxylate (169, Isomer-A
at C-1', Scheme-15)

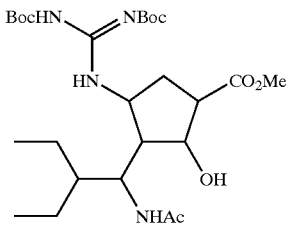

It was prepared from 153 (0.6 g) using the same procedure as for compound 94.

EXAMPLE 160

(±)-Methyl t-3-(1'-Acetylamino-3'-ethyl)pentyl-c-4-[(tert-butoxycarbonylamino-tert-butoxycarbonylimino)methyl]amino-t-2-acetyloxycyclopentan-r-1-carboxylate (170, Isomer-A at C-1', Scheme-15)

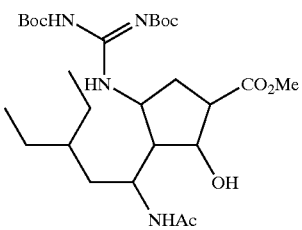

It was prepared from 155 (0.25 g) using the same procedure as for compound 94.

EXAMPLE 161

(±)-Methyl t-3-(1'-Acetylamino-n-butyl)-c-4-[(tert-butoxycarbonylamino-tert-butoxycarbonylimino)methyl]amino-t-2-acetyloxycyclopentan-r-1-carboxylate (171, Isomer-A at C-1', Scheme-15)

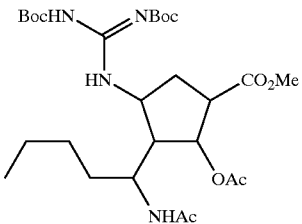

It was prepared from 156 (0.26 g) using the same procedure as for compound 94.

EXAMPLE 162

(1S,2S,3R,4R,1'S)-(−)-Ethyl 3-(1'-Acetylamino-2'-ethyl)butyl-4-[(N-tert-butoxycarbonyl-N-methylamino-N'-tert-butoxycarbonylimino)methyl]amino-2-hydroxycyclopentan-1-carboxylate (172, Scheme-15)

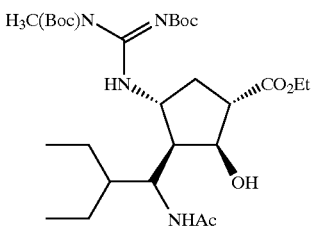

It was prepared from 151 (0.46 g) using the same procedure as for compound 94. The reagent used was 1,3-bis(tert-butoxycarbonyl)-N-methyl-2-(2,4-dinitrophenyl)-2-thiopseudourea instead of 1,3-bis(tert-butoxycarbonyl)-2-methyl-2-thiopseudourea and HgCl$_2$ was not required.

EXAMPLE 163

(1S,2S,3R,4R,1'S)-(−)-Ethyl 3-(1'-Acetylamino-2'-ethyl)butyl-4-[(amino-imino)methyl]-amino-2-hydroxycyclopentan-1-carboxylate (173, Scheme-15)

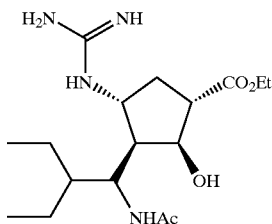

It was prepared from 168 (0.1 g) using the same procedure as for compound 151.

EXAMPLE 164

(±)-Methyl t-3-(1'-Acetylamino-2'-ethyl)butyl-c-4-[(amino-imino)methyl]amino-t-2-hydroxycyclopentan-r-1-carboxylate (174, Isomer-A at C-1', Scheme-14)

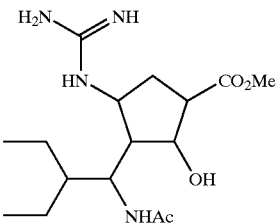

It was prepared from 169 (0.38 g) using the same procedure as for compound 151.

EXAMPLE 165

(±)-Methyl t-3-(1'-Acetylamino-3'-ethyl)pentyl-c-4-[(amino-imino)methyl]amino-t-2-acetyloxycyclopentan-r-1-carboxylate (175, Isomer-A at C-1', Scheme-15)

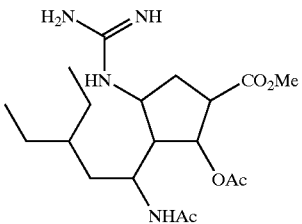

It was prepared from 170 (0.1 g) using the same procedure as for compound 151.

EXAMPLE 166

(±)-Methyl t-3-(1'-Acetylamino-n-butyl)-c-4-[(amino-imino)methyl]amino-t-2-acetyloxycyclopentan-r-1-carboxylate (176, Isomer-A at C-1', Scheme-15)

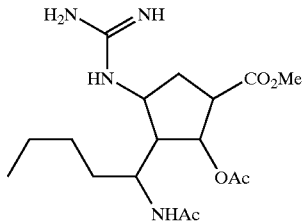

It was prepared from 171 (0.08 g) using the same procedure as for compound 151.

EXAMPLE 167

(1S,2S,3R,4R,1'S)-(−)-Ethyl-3-(1'-acetylamino-2'-ethyl)butyl-4-[(N-methylamino-imino)methyl]amino-2-hydroxycyclopentan-1-carboxylate (177, Scheme-15)

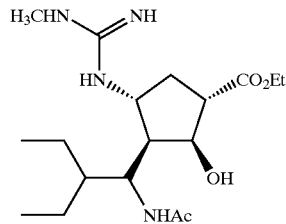

It was prepared from 172 (0.3 g) using the same procedure as for compound 151.

EXAMPLE 168

(1S,2S,3R,4R,1'S)-(−)-3-(1'-Acetylamino-2'-ethyl)butyl-4-[(aminoimino)methyl]amino-2-hydroxycyclopentan-1-carboxylic Acid (178, Scheme-15)

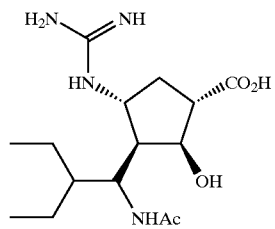

Method-A:
It was prepared from 173 (7.8 mg, 0.0166 mmol) using the same procedure as for compound 160 and was obtained as 7.2 mmolar solution.
MS (ES+): 329.5 (M+1).
Method-B:
To a mixture of 149 (3.0 g, 8.9 mmol) in DMF (20 mL) was added pyrazole carboxamidine hydrochloride (1.56 g, 10.6 mmol) and di-isopropylethylamine (3.9 mL, 22.4 mmol) and heated at 60° C. for 36 h. Additional amount of pyrazole carboxamidine hydrochloride (0.65 g) and di-isopropyl ethylamine (1 mL) were added and heated at 60° C. for another 12 h. The solvent was evaporated under reduced pressure. To the residue was added 1N NaOH (22 mL, 22 mmol) and stirred at room temperature for 5 h. The reaction mixture was extracted with ethyl acetate (3×25 mL) and the aqueous layer was concentrated. The solid was obtained, which was collected by filtration and dried to give 1.22 g (39%) of compound 178.

$^1$H NMR (D$_2$O): $^1$H NMR (D$_2$O): δ ppm 0.90 (m, 3H), 0.95 (m, 3H), 1.05 (m, 2H), 1.5 (m, 3H), 1.8 (m, 1H), 2.0 (s, 3H), 2.3 (m, 1H), 2.55 (m, 1H), 2.75 (m, 1H), 3.9 (m, 1H), 4.4 (m, 2H).

| Analysis: | Calcd for C$_{15}$H$_{28}$N$_4$O$_4$·H$_2$O: | C, 52.01; H, 8.73; N, 16.17 |
|---|---|---|
| | Found: | C, 51.64; H, 8.57; N, 16.14 |

EXAMPLE 169

(±)-t-3-(1'-Acetylamino-2'-ethyl)butyl-c-4-[(amino-imino)methyl]amino-t-2-hydroxycyclopentan-r-1-carboxylic Acid (179, Isomer-A at C-1', Scheme-15)

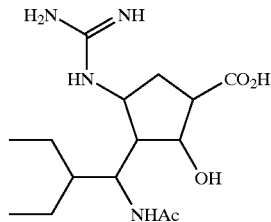

It was prepared from 174 (12.0 mg, 0.0263 mmol) using the same procedure as for compound 160 (method-A) and was obtained as 26.3 mmolar solution.
MS (ES+): 329.5 (M+1).

EXAMPLE 170

(±)-t-3-(1'-Acetylamino-3'-ethyl)pentyl-c-4-[(amino-imino)methyl]amino-t-2-hydroxycyclopentan-r-1-carboxylic Acid (180, Isomer-A at C-1', Scheme-15)

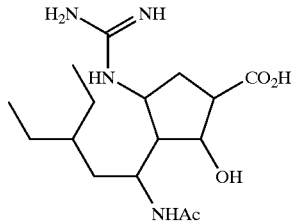

It was prepared from 175 (9.0 mg, 0.0176 mmol) using the same procedure as for compound 160 (method-A) and was obtained as 17.6 mmolar solution.
MS (ES+): 343.5 (M+1).

EXAMPLE 171

(±)-t-3-(1'-Acetylamino-n-butyl)-c-4-[(amino-imino)methyl]amino-t-2-hydroxycyclopentan-r-1-carboxylic Acid (181, Isomer-A at C-1', Scheme-15)

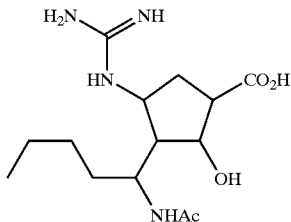

It was prepared from 176 (4.9 mg, 0.010 mmol) using the same procedure as for compound 160 (method-A) and was obtained as 10.0 mmolar solution.

MS (ES+): 315.0 (M+1).

EXAMPLE 172

(1S,2S,3R,4R,1'S)-(−)-3-(1'-Acetylamino-2'-ethyl)butyl-4-[(N-methylamino-imino)methyl]amino-2-hydroxycyclopentan-1-carboxylic Acid (182, Scheme-15)

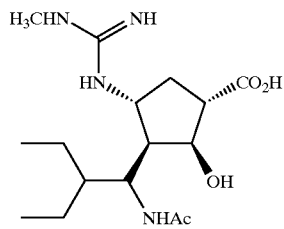

It was prepared from 177 (10.4 mg, 0.0203 mmol) using the same procedure as for compound 160 (method-A) and was obtained as 20.3 mmolar solution.

MS (ES+): 343.6 (M+1).

EXAMPLE 173

(1S,2S,3R,4R,1'S)-(−)-3-(1'-Acetylamino-2'-propyl)pentyl-4-[(amino-imino)methyl]amino-2-hydroxycyclopentan-1-carboxylic Acid (183, Scheme-15)

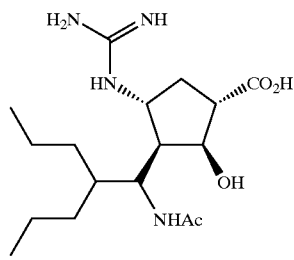

It was prepared from 150 (8.7 g) using the same procedure as for compound 178 (method-B).

EXAMPLE 174

(1S,2S,3R,4R,1'S)-(−)-Methyl 3-(1'-Acetylamino-2'-ethyl)butyl-4-tert-butoxycarbonyl-amino-2-(N-imidazolyl-thiocarbonyloxy)cyclopentan-1-carboxylate (184, Scheme-16)

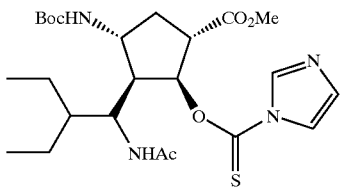

A mixture of 137 (100 g, 0.25 mol) and 1,1'-thiocarbonyldiimidazole (90 g, 0.5 mol) in anh. THF (1.3 L) was heated at reflux temperature for 16 h. The solvent was removed under reduced pressure and the residue dissolved in ethyl acetate (1 L) and washed with 0.5N HCl (3×1 L). Ethyl acetate layer was dried over $MgSO_4$ and after filtration, the filtrate was concentrated. The residue was re-crystallized from ethyl acetate/hexane to give 76 g (59.6%) of compound 184. The filtrate was concentrated and the residue purified by passing through a column of silica gel using ethyl acetate/hexane as an eluent to give additional 14 g (11%) of 184.

$^1$H NMR (CDCl$_3$): δ 0.75 (m, 3H), 0.9 (m, 3H), 1.15 (m, 3H), 1.4 (m, 9H), 1.9 (m, 2H), 2.0 (s, 3H), 2.5 (m, 2H), 3.1 (m, 1H), 3.75 (s, 3H), 4.25 (m, 1H), 4.5 (m, 1H), 5.0 (m, 1H), 6.0 (m, 1H), 6.4 (m, 1H), 7.05 (s, 1H), 7.7 (s, 1H), 8.4 (s, 1H)

| Analysis: | Calcd for $C_{24}H_{38}N_4O_6S$: | C, 56.45; H, 7.50; N, 10.97 |
|---|---|---|
| | Found: | C, 56.40; H, 7.50; N, 10.98 |

EXAMPLE 175

(1S,2S,3R,4R,1'S)-(−)-Methyl 3-(1'-Acetylamino-2'-propyl)pentyl-4-tert-butoxycarbonylamino-2-(N-imidazolyl-thiocarbonyloxy)cyclopentan-1-carboxylate (185, Scheme-16)

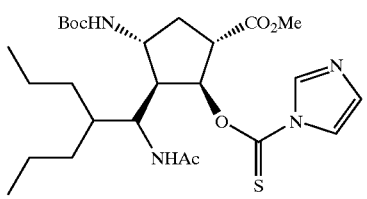

It was prepared from 138 (17.1 g) according to the same procedure used for compound 184.

EXAMPLE 176

(1S,2S,3R,4R,1'S)-(−)-Ethyl 3-(1'-Acetylamino-2'-ethyl)butyl-4-tert-butoxycarbonyl-amino-2-(N-imidazolyl-thiocarbonyloxy)cyclopentan-1-carboxylate (186, Scheme-16)

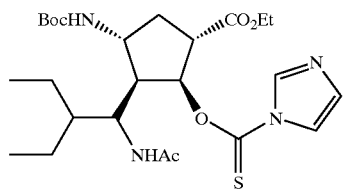

It was prepared from 139 (2.8 g) according to the same procedure used for compound 184.

EXAMPLE 177

(1S,2S,3R,4R,1'S)-(−)-Methyl 3-(1'-Acetylamino-2'-propyl)pentyl-4-tert-butoxycarbonyl-amino-2-(N-imidazolyl-thiocarbonyloxy)cyclopentan-1-carboxylate (187, Scheme-16)

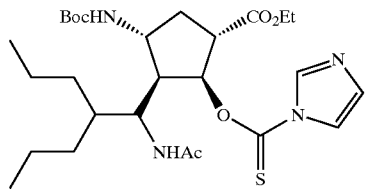

It was prepared from 140 (3.43 g) according to the same procedure used for compound 184.

EXAMPLE 178

(±)-Methyl t-3-(1'-Acetylamino-2'-ethyl)butyl-c-4-tert-butoxycarbonylamino-t-2-(N-imidazolyl-thiocarbonyloxy)cyclopentan-r-1-carboxylate (188, Isomer-A at C-1', Scheme-16)

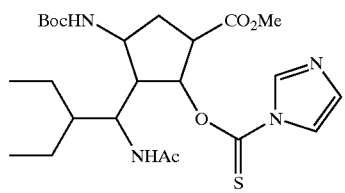

It was prepared from 142 (0.4 g) according to the same procedure used for compound 184.

EXAMPLE 179

(1R,3R,4R,1'S)-(−)-Methyl 3-(1'-Acetylamino-2'-ethyl)butyl-4-tert-butoxycarbonyl-aminocyclopentan-1-carboxylate (189, Scheme-16)

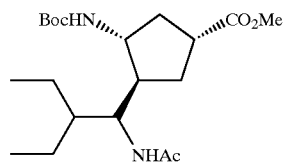

To a mixture of 184 (50 g, 0.098 mol) in toluene (1.3 L) at 70° C. were added tributyltin hydride (34 mL, 0.126 mol) followed by azobisisobutyronitrile (AIBN, 0.1 g, 0.06 mmol) and the mixture was stirred at 70° C. for 10 min. The solvent was removed in vacuo and the residue was dissolved in acetonitrile (1 L) and washed with hexanes (3×1 L). Acetonitrile layer was concentrated and the residue purified by passing through a column of silica gel using ethyl acetate:hexanes (0–50% mixture) as an eluent. The appropriate fractions were pooled together and concentrated to give 36 g (95%) of compound 189.

$^1$H NMR (DMSO-$d_6$): δ 0.8 (m, 6H), 1.2 (m, 5H), 1.4 (s, 9H), 1.6 (m, 2H), 1.85 (s, 3H), 1.9 (m, 1H), 2.1 (m, 2H), 2.7 (m, 1H), 3.55 (s, 3H), 3.7 (m, 1H), 3.8 (m, 1H) 6.72 (d, J=7.5 Hz, 1H), 7.20 (d, J=9.9 Hz, 1H)

| Analysis: | Calcd for $C_{20}H_{36}N_2O_5 \cdot 0.75H_2O$: | C, 60.35; H, 9.50; N, 7.04 |
|---|---|---|
| | Found: | C, 60.60; H, 9.49; N, 7.05 |

EXAMPLE 180

(1R,3R,4R,1'S)-(−)-Methyl 3-(1'-Acetylamino-2'-propyl)pentyl-4-tert-butoxycarbonyl-aminocyclopentan-1-carboxylate (190, Scheme-16)

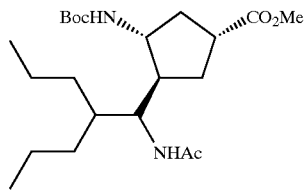

It was prepared from 185 (16.0 g) according to the same procedure used for compound 189.

EXAMPLE 181

(1R,3R,4R,1'S)-(−)-Ethyl 3-(1'-Acetylamino-2'-ethyl)butyl-4-tert-butoxycarbonyl-amino-cyclopentan-1-carboxylate (191, Scheme-16)

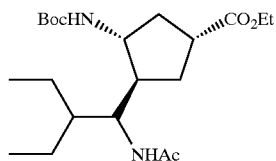

It was prepared from 186 (1.9 g) according to the same procedure used for compound 189.

EXAMPLE 182

(1R,3R,4R,1'S)-(−)-Methyl 3-(1'-Acetylamino-2'-propyl)pentyl-4-tert-butoxycarbonyl-aminocyclopentan-1-carboxylate (192, Scheme-16)

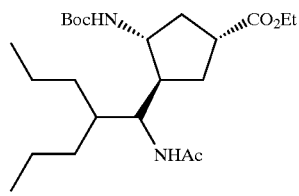

It was prepared from 187 (1.2 g) according to the same procedure used for compound 189.

EXAMPLE 183

(±)-Methyl t-3-(1'-Acetylamino-2'-ethyl)butyl-c-4-tert-butoxycarbonylaminocyclopentan-1-carboxylate (193, Isomer-A at C-1', Scheme-16)

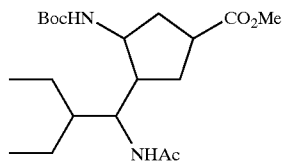

It was prepared from 188 (0.2 g) according to the same procedure used for compound 189.

EXAMPLE 184

(1R,3R,4R,1'S)-(−)-Methyl 3-(1'-Acetylamino-2'-ethyl)butyl-4-Aminocyclopentan-1-carboxylate Hydrochloride (194, Scheme-16)

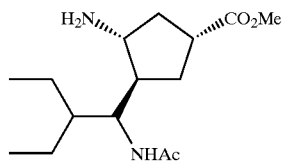

It was prepared from 189 (10.0 g) according to the same procedure used for compound 149.

EXAMPLE 185

(1R,3R,4R,1'S)-(−)-Methyl 3-(1'-Acetylamino-2'-propyl)pentyl-4-Aminocyclopentan-1-carboxylate Hydrochloride (195, Scheme-16)

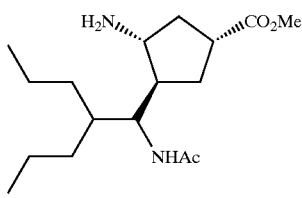

It was prepared from 190 (10.0 g) according to the same procedure used for compound 149.

EXAMPLE 186

(1R,3R,4R,1'S)-(−)-Ethyl 3-(1'-Acetylamino-2'-ethyl)butyl-4-Aminocyclopentan-1-carboxylate Trifluoroactate (196, Scheme-16)

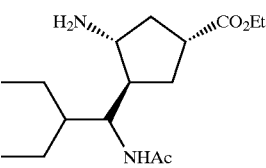

It was prepared from 191 (1.4 g) according to the same procedure used for compound 151.

EXAMPLE 187

(1R,3R,4R,1'S)-(−)-Ethyl-3-(1'-Acetylamino-2'-propyl)pentyl-4-aminocyclopentan-1-carboxylate Trifluoroacetate (197, Scheme-16)

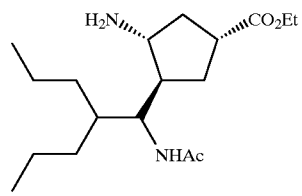

It was prepared from 192 (0.84 g) according to the same procedure used for compound 151.

EXAMPLE 188

(±)-Methyl t-3-(1'-Acetylamino-2'-ethyl)butyl-c-4-aminocyclopentan-1-carboxylate Trifluoroacetate (198, Isomer-A at C-1', Scheme-16)

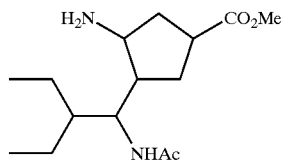

It was prepared from 193 (5.7 mg) according to the same procedure used for compound 151.

EXAMPLE 189

(1R,3R,4R,1'S)-(−)-3-(1'-Acetylamino-2'-ethyl)butyl-4-aminocyclopentan-1-carboxylic Acid (199, Scheme-16)

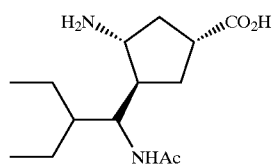

It was prepared from 196 (8.3 mg, 0.0233 mmol) using the same procedure as for compound 160 and was obtained as 23.3 mmolar solution.

MS (ES+): 271.4 (100%, M+1).

EXAMPLE 190

(±)-t-3-(1'-Acetylamino-2'-ethyl)butyl-c-4-aminocyclopentan-1-carboxylic Acid (200, Isomer-A at C-1', Scheme-16)

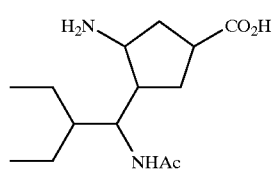

It was prepared from 198 (4.21 mg, 0.0148 mmol) using the same procedure as for compound 160 and was obtained as 14.8 mmolar solution.

MS (ES+): 271.4 (100%, M+1).

EXAMPLE 191

(1R,3R,4R,1'S)-(−)-Ethyl 3-(1'-Acetylamino-2'-ethyl)butyl-4-[(tert-butoxycarbonylamino-tert-butoxycarbonylimino)methyl]aminocyclopentan-1-carboxylate (201, Scheme-17)

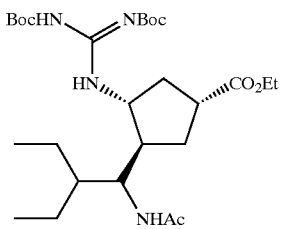

It was prepared from 196 (1.52 g) using the same procedure as for compound 94.

EXAMPLE 192

(1R,3R,4R,1'S)-(−)-Ethyl 3-(1'-Acetylamino-2'-propyl)pentyl-4-[(tert-butoxycarbonylamino-tert-butoxycarbonylimino)methyl]aminocyclopentan-1-carboxylate (202, Scheme-17)

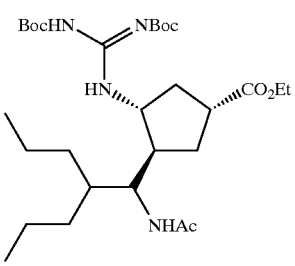

It was prepared from 197 (0.87 g) using the same procedure as for compound 94.

EXAMPLE 193

(±)-Methyl t-3-(1'-Acetylamino-2'-ethyl)butyl-c-4-[(tert-butoxycarbonylamino-tert-butoxycarbonylimino)methyl]aminocyclopentan-r-1-carboxylate (203, Isomer-A at C-1', Scheme-17)

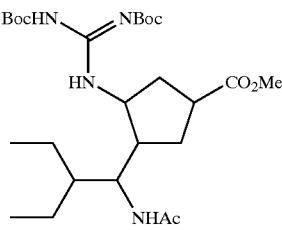

It was prepared from 198 (0.093 g) using the same procedure as for compound 94.

EXAMPLE 194

(1R,3R,4R,1'S)-(−)-Ethyl 3-(1'-Acetylamino-2'-ethyl)butyl-4-[(N-tert-butoxycarbonyl-N-methylamino-N'-tert-butoxycarbonylimino)methyl]aminocyclopentan-1-carboxylate (204, Scheme-17)

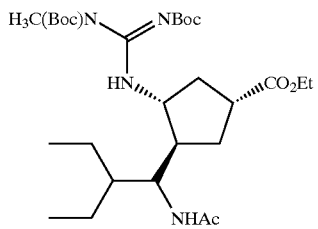

It was prepared from 196 (0.33 g) using the same procedure as for compound 94. The reagent used was 1,3-bis(tert-butoxycarbonyl)-N-methyl-2-(2,4-dinitrophenyl)-2-thiopseudourea instead of 1,3-bis(tert-butoxycarbonyl)-2-methyl-2-thiopseudourea.

EXAMPLE 195

(1R,3R,4R,1'S)-(−)-Ethyl 3-(1'-acetylamino-2'-ethyl)butyl-4-[(amino-imino)methyl]-aminocyclopentan-1-carboxylate Trifluoroacetate (205, Scheme-17)

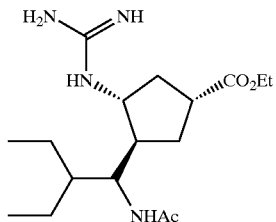

It was prepared from 201 (0.9 g) using the same procedure as for compound 151.

EXAMPLE 196

(1R,3R,4R,1'S)-(−)-Ethyl 3-(1'-Acetylamino-2'-propyl)pentyl-4-[(amino-imino)-methyl]aminocyclopentan-1-carboxylate Trifluoroacetate (206, Scheme-17)

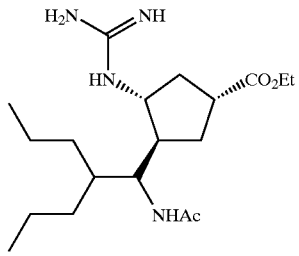

It was prepared from 202 (0.8 g) using the same procedure as for compound 151.

EXAMPLE 197

(±)-Methyl t-3-(1'-Acetylamino-2'-ethyl)butyl-c-4-[(amino-imino)methyl]-aminocyclo-pentan-r-1-carboxylate Trifluoroacetate (207, Isomer-A at C-1', Scheme-17)

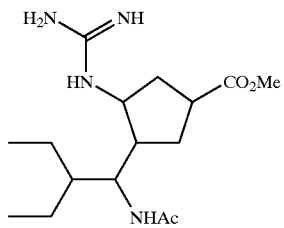

It was prepared from 203 (0.055 g) using the same procedure as for compound 151.

EXAMPLE 198

(1R,3R,4R,1'S)-(−)-Ethyl-3-(1'-acetylamino-2'-ethyl)butyl-4-[(N-methylamino-imino)methyl]aminocyclopentan-1-carboxylate Trifluoroacetate (208, Scheme-17)

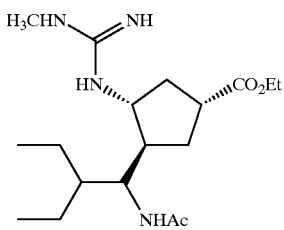

It was prepared from 204 (0.35 g) using the same procedure as for compound 151.

EXAMPLE 199

(1R,3R,4R,1'S)-(−)-3-(1'-Acetylamino-2'-ethyl)butyl-4-(aminoimino)methyl-aminocyclopentan-1-carboxylic Acid (209, Scheme-17)

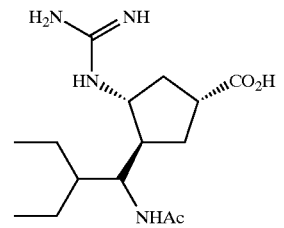

Method-A:
It was prepared from 205 (7.6 mg, 0.0167 mmol) using the same procedure as for compound 160 and was obtained as 16.7 mmolar solution.
MS (ES+): 313.4 (100%, M+1).
Method-B:
It was prepared from 194 (15.02 g) using the same procedure as for compound 178 (Method-B).
$^1$H NMR (D$_2$O): δ 0.90 (m, 6H), 1.1(m, 2H), 1.4 (m, 1H), 1.5 (m, 2H), 1.75 (m, 2H), 2.05 (s, 3H), 2.15 (m, 1H), 2.35 (m, 2H), 2.8 (m, 1H), 3.65 (m, 1H), 4.0 (m, 1H).

EXAMPLE 200

(1R,3R,4R,1'S)-(−)-3-(1'-Acetylamino-2'-propyl)pentyl-4-[(amino-imino)methyl]aminocyclopentan-1-carboxylic Acid (210, Scheme-17)

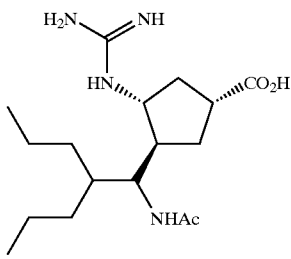

Method-A:

It was prepared from 206 (9.69 mg, 0.0197 mmol) using the same procedure as for compound 160 and was obtained as 14.9 mmolar solution.

MS (ES+): 341.7 (100%, M+1).

Method-B:

It was prepared from 153 (8.4 g) using the same procedure as for compound 178 (Method-B).

$^1$H NMR (D$_2$O): δ 0.90 (m, 6H), 1.1 (m, 2H), 1.4 (m, 6H), 1.6 (m, 1H), 1.75 (m, 2H), 2.05 (s, 3H), 2.15 (m, 1H), 2.3 (m, 1H), 2.4 (m, 1H), 2.78 (m, 1H), 3.6 (m, 1H), 3.9 (m, 1H)

EXAMPLE 201

(±)-t-3-(1'-Acetylamino-2'-ethyl)butyl-c-4-[(amino-imino)methyl]-aminocyclopentan-r-1-carboxylic Acid (211, Isomer-A at C-1', Scheme-17)

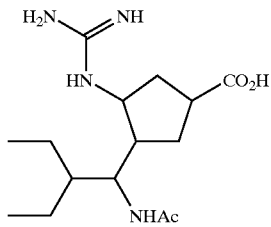

It was prepared from 207 (18 mg, 0.0342 mmol) using the same procedure as for compound 160 and was obtained as 34.2 mmolar solution.

MS (ES+): 313.4 (100%, M+1).

EXAMPLE 202

(1R,3R,4R,1'S)-(−)-3-(1'-Acetylamino-2'-ethyl)butyl-4-[(N-methylamino-imino)methyl]aminoclopentan-1-carboxylic Acid (212, Scheme-17)

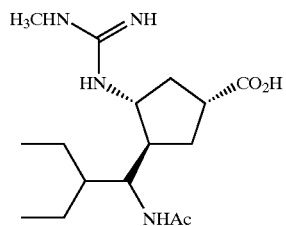

It was prepared from 208 (10.7 mg, 0.0235 mmol) using the same procedure as for compound 160 and was obtained as 30.18 mmolar solution.

MS (ES+): 327.6 (100%, M+1).

EXAMPLE 203

(1S,2S,3R,4R,1'S)-(−)-Methyl 3-(1'-Acetylamino-2'-ethyl)butyl-4-tert-butoxycarbonylamino-2-methanesulfonyloxycyclopentan-1-carboxylate (213, Scheme-18)

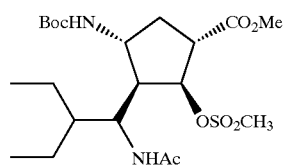

To a mixture of 137 (1.0 g, 2.4 mmol) in dichloromethane (40 mL) was added methanesulfonyl chloride (0.37 mL, 4.8 mmol) and triethylamine (1.0 mL, 7.2 mmol) at 4° C. The reaction mixture was stirred for 16 h at 4° C. To the mixture was added water (10 mL) and extracted with dichloromethane (3×10 mL). The combined organic extracts were washed with brine (20 mL) and dried (MgSO$_4$). After filtration, the filtrate was concentrated and the residue purified by passing through a column of silica gel to give 0.8 g (68%) of compound 213.

MS (ES+1): 493.8 (M+1).

EXAMPLE 204

(3R,4R,1'S)-(−)-Methyl-3-(1'-Acetylamino-2'-ethyl)butyl-4-tert-butoxycarbonylamino-cyclopent-1-en-1-carboxylate (214, Scheme-18)

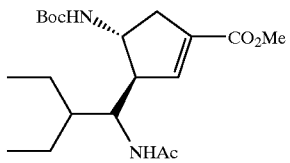

To a mixture of 213 (0.4 g, 0.81 mmol) in THF (5 mL) at 4° C. was added freshly prepared sodium ethoxide (2.43 mmol) in ethanol (1.5 mL) and stirred for 30 min. The mixture was neutralized with acetic acid and concentrated. The residue was taken in dichloromethane (20 mL) and washed with water and brine and dried (MgSO$_4$). After filtration, the filtrate was concentrated and the residue purified on silica gel column to give 0.11 g (37%) of 214.

MS (ES+): 397.8 (M+1).

EXAMPLE 205

(3R,4R,1'S)-(−)-Methyl 3-(1'-Acetylamino-2'-ethyl)butyl-4-aminocyclopent-1-en-1-carboxylate Hydrochloride (215, Scheme-18)

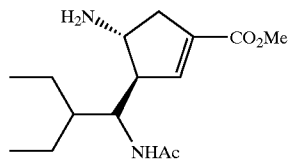

It was prepared from 214 (23 mg, 0.81 mmol) according to the method used for compound 149 and used as such for the next step.

MS (ES+): 297.5 (M+1).

EXAMPLE 206

(3R,4R,1'S)-(−) 3-(1'-Acetylamino-2'-ethyl)butyl-4-aminocyclopent-1-en-1-carboxylic Acid (216, Scheme-18)

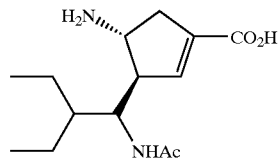

The mixture of 216, obtained above, was treated the same way as compound 160 and was obtained as 58 mmolar solution.

EXAMPLE 207

(3R,4R,1'S)-(−)-Methyl 3-(1'-Acetylamino-2'-ethyl)butyl-4-[(tert-butoxycarbonylamino-tert-butoxycarbonylimino)methyl]aminocyclopent-1-en-1-carboxylate (217, Scheme-18)

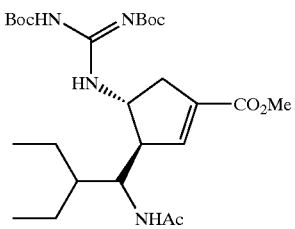

A mixture of 215 (4.23 g, 13.6 mmol), N-tert-butoxycarbonyl-N'-tert-butoxycarbonyl-N''-trifluoromethanesulfonylguanidine (5.87 g, 15 mmol) and triethylamine (4.1 mL, 29.2 mmol) in dichloromethane (70 mL) was stirred at room temperature for 16 h. The reaction mixture was washed with saturated sodium bicarbonate solution, water, and brine and dried (MgSO$_4$). After filtration, the filtrate was concentrated and the residue purified by passing through a column of silica gel to give 3.9 g (60%) of compound 217.

MS (ES+): 526.08 (M+1).

EXAMPLE 208

(3R,4R,1'S)-(−)-3-(1'-Acetylamino-2'-ethyl)butyl-4-[(tert-butoxycarbonylamino-tert-butoxycarbonylimino)methyl]aminocyclopent-1-en-1-carboxylic Acid (218, Scheme-18)

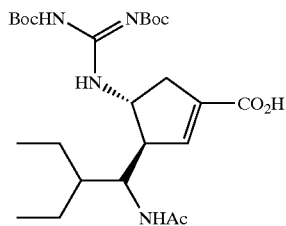

A mixture of 217 (1.8 g, 3.4 mmol), THF (10 mL), ethanol (10 mL), water (10 mL) and 1N NaOH (10 mL) was stirred at room temperature for 8 h. The reaction mixture was concentrated and the residual aqueous layer was washed with ether (20 mL) and acidified with acetic acid. The solid was collected by filtration, washed with water and dried to give 1.6 g (92%) of compound 218.

MS (ES+): 512.0 (M+1).

EXAMPLE 209

(3R,4R,1'S)-(−)-3-(1'-Acetylamino-2'-ethyl)butyl-4-[(amino-imino)methyl]amino-cyclopent-1-en-1-carboxylic Acid Hydrochloride (219, Scheme-18)

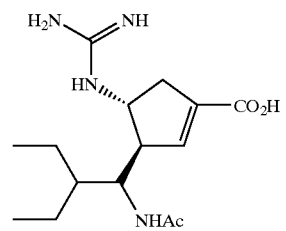

A mixture of 218 (1.52 g, 2.98 mmol) and 3N HCl (20 mL, 60 mmol) was stirred for 24 h. The reaction mixture was concentrated and dried. The residue on crystallization with ethanol/ether gave 0.85 g (83%) of compound 219.

MS (ES+): 311.4 (M+1).

| Analysis: | Calcd for $C_{15}H_{26}N_4O_3$·HCl: | C, 51.94; H, 7.56; N, 16.15 |
|---|---|---|
| | Found: | C, 51.84; H, 7.75; N, 16.03 |

Biochemistry

The in vitro assay is based on the method reported by von Itzstein et al. (EP Application 92309634.6). The neuraminidase from the H1N9 strain of influenza was obtained by the method described by Laver et al. Virology 1984, 137, p. 314–323. Values for the $IC_{50}$ were measured via spectrofluorometric technique which uses the flouorogenic substrate, 2'-(4-methylumbelliferyl)-α-D-acetylneuramic acid. This substrate is cleaved by neuraminidase to yield a fluorescent product which can be quantified. The assay mixture contains inhibitors at various concentrations (four to six points) and enzyme in 32.5 mM MES [(2-(N-morpholino) ethanesulfonic acid]buffer, 4 mM $CaCl_2$ at pH=6.5 (total volume=80 μL). The reaction is started by the addition of 20 μL of the substrate to a final concentration of 75 μM. After 10 min at 37° C., 150 μl of 0.2M glycine/NaOH (pH=10.2) is added to 0.1 mL of the reaction mixture to terminate the reaction. A blank is run with the same substrate solution with no enzyme. Fluorescence is read using a spectrafluor Fluorometer (excitation: 360 nm and emission: 450 nm) and readings from substrate blanks were subtracted from the sample readings. The $IC_{50}$ is calculated by plotting percent inhibition of NA activity versus the inhibitor concentration, and determination of each point is performed in duplicate.

Biological Data

The following table provides the neuraminidase enzyme inhibition data ($IC_{50}$ values).

+>100 μM; ++1–100 μM; +++<1 μM.

| Compound no. | Flu A | Flu B |
|---|---|---|
| 65 | ++ | ++ |
| 86 | ++ | ++ |
| 160 | +++ | +++ |
| 162 | +++ | +++ |
| 163 | +++ | +++ |
| 165 | ++ | ++ |
| 166 | +++ | ++ |
| 178 | +++ | +++ |
| 179 | +++ | +++ |
| 180 | +++ | +++ |
| 181 | +++ | +++ |
| 182 | +++ | +++ |
| 183 | +++ | +++ |
| 199 | +++ | +++ |
| 200 | +++ | +++ |
| 209 | +++ | +++ |
| 210 | +++ | +++ |
| 211 | +++ | +++ |
| 212 | +++ | +++ |
| 219 | +++ | +++ |

Crystallography

Complexes between neuraminidase and inhibition molecules were prepared by transferring H1N9 neuraminidase crystals into 2 mL of the phosphate buffer solution in which the inhibitor has been dissolved. The concentration of the inhibitor compound was adjusted to be 2 mM. The crystal was allowed to equilibrate in the buffer solution for about one day and then removed from the solution and mounted in a glass capillary for X-ray diffraction data collection. All X-ray intensity measurements were recorded with a Siemens X-100 multiwire area detector on a Rigaku RU-300 rotating anode generator operating at 100 mA and 50 KV and a copper anode. The crystal to detector distance was 160 mm and the detector was offset 2.2 Å data. Intensity data were measured on 0.1 Å oscillation frames at 240 s of exposure per fame. Each crystal yielded 600–700 frames of data before radiation damage to the crystals prevented further data collection.

The intensity data were processed using the XENGEN package of programs. The integrated intensities were scaled and merged to produce a final data set containing only unique reflections. All refinement was carried out using the program XPLOR. The starting model for refinement was the 2.0 Å refined native N9 structure. Difference Fourier maps to 2.2 Å were calculated using the calculated phases from the refined model. Analysis of the electron density maps was performed on a Silicon Graphics Indigo Extreme 2 computer graphics workstation using the graphics program QUANTA. Idealized models for the inhibitor molecules were manually fitted to the difference electron density. These inhibitor models were later included in the XPLOR refinement.

Dosage and Formulation

The antiviral compounds of this invention can be administered as treatment for viral infections by any means that produce contact of the active agent's site for action with the viral neuraminidase in the body of a human, mammal, bird, or other animal. They can be administered by a conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms, the kind of concurrent treatment; the frequency of treatment; and the effect desire. A daily dosage of active ingredient can be expected to be about 0.001 to 1000 milligram (mg) per kilogram (kg) of body weight, with the preferred dose being 0.1 to about 30 mg/kg.

Dosage forms (compositions sutiable for administration) contain from about 1 mg to about 500 mg of active ingredient per unit. In these pharmaceutical compositions, the active ingredient will ordinarily be present in an amount of about 0.5–95% weight based on the total weight of the composition.

The active ingredient can be administered orally in solid dosage forms, such as capsules, tablets, and powders, or in liquid dosage forms, such as elixirs, syrups and suspensions. It can also be administered parenterally, in sterile liquid dosage forms. The active ingredient can also be administered intranasally (nose drops) or by inhalation of a drug powder mist. Other dosage forms are potentially possible such as administration transdermally, via a patch mechanism or ointment.

Gelatin capsules contain the active ingredient and powdered carriers, such as lactose, starch, cellulose derivatives, biocompatible polymers, magnesium stearate, stearic acid, and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and protect the tablet from the atmosphere, or enteric coated for selective disintegration in the gastrointestinal tract.

Liquid dosage forms for oral administration can contain coloring and flavoring to increase patient acceptance. They may also contain buffering agents, surfactants and preservatives. Liquid oral products can be developed to have sustained-release properties. They may also contain cyclodextrin derivatives to enhance the solubility of the active ingredient and to promote its oral uptake.

In general, water, a suitable oil, saline, aqueous dextrose (glucose), and related sugar solutions and glycol such as propylene glycol or polyethylene glycol are suitable carriers for parental solutions. Solutions for parenteral administration preferably contain a water-soluble salt of the active ingredient, suitable stabilizing agents, and, if necessary, buffering agents. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in Remington's Pharmaceutical Sciences, Mack Publishing Company and in the Handbook of Pharmaceuticals Excipients, American Pharmaceutical Association, both standard reference texts in this field.

Useful pharmaceutical dosage forms for administration of the compounds according to the present invention can be illustrated as follows:

Hard Shell Capsules

A large number of unit capsules are prepared by filling standard two-piece hard gelatin capsules each with 100 mg of powdered active ingredient, 150 mg of lactose, 50 mg of cellulose, and 6 mg of magnesium stearate.

Soft Gelatin Capsules

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets

A large number of tablets are prepared by conventional procedures so that the dosage unit was 100 mg of active ingredient, 0.2 mg of colloidal silicon dioxide, 5 mg of magnesium stearate, 275 mg of microcrystalline cellulose, 11 mg of starch, and 98.8 mg of lactose. Appropriate aqueous and non-aqueous coatings may be applied to increase palatability, improve elegance and stability or delay absorption.

Immediate Release Tablets/Capsules

These are solid oral dosage forms made by conventional and novel processes. These units are taken orally without water for immediate dissolution and delivery of the medication. The active ingredient is mixed in liquid containing ingredient such as sugar, gelatin, pectin, and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Moreover, the compounds of the present invention can be administered in the form of nose drops, or metered dose and a nasal or buccal inhalers. The drug is delivered from a nasal solution as a fine mist or from a powder as an aerosol.

Various modifications of the invention in addition to those shown and described herein will be apparent to those skilled in the art from the foregoing description. Such modifications are also intended to fall within the scope of the appended claims.

The foregoing disclosure includes all the information deemed essential enable those skilled in the art to practice the claimed invention. Because the cited application may provide further useful information, these cited materials are hereby incorporated by reference in their entirety.

What is claimed is:

1. A compound represented by the formulae:

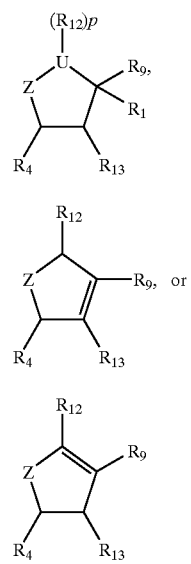

wherein

U is CH and p is 1

Z is —C($R_2$)($R_3$), —CH—N($R_2$)($R_3$), C($R_3$)[($CH_2$)$_n R_2$], CH—C($R_3$)($R_8$)($CH_2$)$_n R_2$, C[($CH_2$)$_n R_2$]—[CH($R_3$)($R_8$)], C[($R_3$)][CH($CH_2$)$_n R_2$($R_8$)];

$R_1$ is H, ($CH_2$)$_n$OH, ($CH_2$)$_n$$NH_2$, ($CH_2$)$_n$$NR_{10}R_{11}$, ($CH_2$)$_n$$OR_{11}$, ($CH_2$)$_n$$SR_{11}$, ($CH_2$)$_n$ halogen $R_9$ is ($CH_2$)$_n$$CO_2$H, ($CH_2$)$_n$$SO_3$H, ($CH_2$)$_n$$PO_3$$H_2$, ($CH_2$)$_n$$NO_2$, C($SCH_3$)$_3$, esters thereof, or salts thereof; or $R_1$ $R_9$ together represent

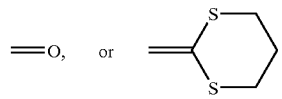

$R_2$ is $NHC(O)R_5$, $NHC(S)R_5$, $NHSO_2R_5$, $C(O)NHR_5$, $SO_2NHR_5$, $CH_2S(O)R_5$, or $CH_2SO_2R_5$;

$R_3$ and $R_8$ individually is H, $(CH_2)_n C(O)R_{10}$, $(CH_2)_n CO_2R_{10}$, $(CH_2)_m OR_{10}$, $CH(OR_{10})CH(R_{10})_m$, $C(O)N(R_{10})_m$, $C(O)N(OR_{10})R_{10}$, $(CH_2)_n N(R_{10})_m$, $CH(R_{10})$ when m is 2, $(CH_2)_n(R_{10})_m$, $CH_2CH(OR_{10})CH_2OR_{10}$, $CH(OR_{10})CH(OR_{10})CH_2OR_{10}$, $CH_2OR_{10}$, $CH(OR_{10})CH_2NHR_{10}$, $CH_2CH(OR_{10})CH_2NHR_{10}$, $CH(OR_{10})CH(OR_{10})CH_2NHR_{10}$, $C(=NR_{10})N(R_{10})_m$, $NHR_{10}$, $NHC(=NR_{10})N(R_{10})_m$, provided that at least one of $R_2$, $R_3$ and $R_8$ is other than H;

$R_4$ is $(CH_2)_n OH$, $(CH_2)_n OR_{11}$, $(CH_2)_n OC(O)R_{11}$, $(CH_2)_n NHC(=NR_{11})NHR_{11}$, $(CH_2)_n NR_{10}R_{11}$, $(CH_2)_n NH_2$, $(CH_2)_n C(=NH)(NH_2)$, $(CH_2)_n NHC(=NR_{11})NH_2$, $(CH_2)_n NHC(=NR_7)NH_2$, $(CH_2)_n CN$, $(CH_2)_n N_3$, $C(=NH)NH_2$, $C(NR_7)NH_2$, or $C(NR_{11})NH_2$;

$R_5$ is H, lower alkyl, cyclo alkyl, halogen substituted alkyl, aryl, substituted aryl or $CF_3$;

$R_7$ is H, $(CH_2)_n OH$, $(CH_2)_n CN$, $(CH_2)_n NH_2$, or $(CH_2)_n NO_2$;

$R_{10}$ is H, lower alkyl, lower alkylene, branched alkyl, cyclic alkyl, $(CH_2)_n$ aromatic, $(CH_2)_n$ substituted aromatic, or when m is 2 both $R_{10}$ groups can also be interconnected to form an N substituted heterocyclic ring, or other 5- or 6-membered heterocyclic ring;

$R_{11}$ is lower alkyl, branched alkyl, $(CH_2)_m$ aromatic, $SO_2R_{10}$, $C(O)R_{10}$ or $C(O)OR_{10}$;

$R_{12}$ and $R_{13}$ is $(CH_2)_n OH$, $(CH_2)_n NH_2$, $(CH_2)_n NR_{10}R_{11}$, $(CH_2)_n OR_{11}$, $(CH_2)_n F$, $(CH_2)_n OC(O)R_{11}$, or $(CH_2)_n NHC(O)R_{11}$, and $R_{12}$ can also be H;

m is 1 or 2;

n is 0–4;

p is 0 or 1;

and pharmaceutically acceptable salts thereof.

2. The compound of claim 1, wherein said lower alkyl group contains 1 to 8 carbon atoms; and said lower alkylene group contains 2 to 8 carbon atoms.

3. The compound of claim 1, wherein said lower alkyl group contains 1 to 3 carbon atoms; and said lower alkylene group contains 2 to 3 carbon atoms.

4. The compound of claim 1, wherein said alkyl group $R_5$, $R_{10}$ and $R_{11}$ is selected from the group consisting of methyl, ethyl, propyl, isopropyl, t-butyl, cyclopentyl, and cyclohexyl, the aromatic group is selected from the group consisting of phenyl and alkyl substituted aromatic groups; the substituted cycloalkyl group contains 3–8 carbon atoms in the ring and are substituted with 1 or 2 alkyl groups having 1–6 carbon atoms, hydroxy group or both; and the alkylene group is selected from the group consisting of vinyl, 1-propenyl, allyl, isopropenyl, 2-methyl-2-propenyl and cyclopentenyl.

5. The compound of claim 1, wherein said salt is from acid selected from the group consisting of hydrochloric, hydrobromic, sulfuric, nitric, perchloric, fumaric, maleic, phosphoric, glycollic, lactic, salicylic, succinic, toluene-p-sulphonic, tartaric, acetic, citric, methanesulphonic, formic, benzoic, malonic, napthalene-2-sulphonic, trifluoroacetic and benzenesulphonic acids.

6. The compound of claim 1, wherein said salt is a sodium or ammonium salt.

7. A compound being selected from the group consisting of (+) 4-Azidocyclopent-2-en-1-one, (+) 3β-{(1'-acetylamino'bis(ethoxycarbonyl)}methyl-4α-azidocyclopentan-1-one, (+) 3β-{1'-Acetylamino-1'-bis(ethoxycarbonyl)}methyl-4α-tert-butoxycarbonylamino-cyclopentan-1-one, (+) 2-{3β-{1'-Acetylamino-1'-bis(ethoxycarbonyl)}methyl-4α-tert-butoxycarbonyl-amino-1-cyclopentylidene}-1,3-dithiane, (+) 2-{3β-(1'-Acetylamino-1'-carboxy)methyl-4α-tert-butoxycarbonylamino-1-cyclopentylidene}-1,3-dithiane, (+) 2-{3β-{1'-Acetylamino-1'-{(N-methoxy-N-methyl)aminocarbonyl}methyl]-4α-tert-butoxycarbonylamino-1-cyclopentylidene}-1,3-dithiane, (+) 2-{3β-(1'-Acetylamino-1'-formyl)methyl-4α-tert-butoxycarbonylamino-1-cyclopentylidene}-1,3-dithiane, (+) 2-{3β-(1'-Acetylamino-1'-ethoxycarbonyl)methyl-4α-tert-butoxycarbonylamino-1-cyclopentylidene}-1,3-dithiane, (+) 2-{3β-(1'-Acetylamino-2'-hydroxy)ethyl-4α-tert-butoxycarbonylamino-1-cyclopentylidene}-1,3-dithiane, (+) 2-{3β-(1'-acetylamino-2'-ethoxy)ethyl-4α-(tert-butoxycarbonyl)amino-1-cyclopentylidene}-1,3-dithiane, (+) Methyl-3β-(1'-acetylamino-2'-ethoxy)ethyl-4α-(tert-butoxycarbonyl)aminocyclopentan-1-carboxylate and (+) Methyl 3β-(1'-acetylamino-2'-ethoxy)ethyl-4α-aminocyclopentan-r-1-carboxylate, (+) 3β-(1'-Acetylamino-2'-ethoxy)ethyl-4α-aminocyclopentan-1-carboxylic acid, (+) 3β-(1'-Acetylamino-2'-ethoxy)ethyl-4α-{(aminoimino)methyl}aminocyclopentan-1-carboxylic acid, (+) t-3-(1'-Acetylamino-1'-di(ethoxycarbonyl)}methyl-c-4-tert-butoxycarbonylamino-t-1-(trismethylthio)methyl}cyclopentan-r-1-ol, (+) t-3-[1'-Acetylamino-1'-carboxy)}methyl-c-4-tert-butoxycarbonylamino-t-1-[(trismethylthio)methyl]cyclopentan-r-1-ol, (+) t-3-[1'-Acetylamino-1'-[(N-methoxy-N-methyl)aminocarbonyl]methyl]-c-4-tert-butoxycarbonylamino-t-1-[(trismethylthio)methyl]cyclopentan-r-1-ol, (+) t-3-(1'-Acetylamino-1'-formyl)methyl-c-4-tert-butoxycarbonylamino-t-1-[(trismethylthio)methyl]cyclopentan-r-1-ol, (+) t-3-{(1'-Acetylamino-3'-ethyl-2'-oxo)pentyl}-c-4-tert-butoxycarbonylamino-t-1-{(trismethylthio)methyl]cyclopentan-r-1-ol, (+) t-3-{(1'-Acetylamino-3'-ethyl-2'-hydroxy)pentyl}-c-4-tert-butoxycarbonylamino-t-1-{(trismethylthio)methyl}cyclopentan-r-1-ol, (+) Methyl c-3-{(1'-acetylamino-3'-ethyl-2'-hydroxy)pentyl}-t-4-tert-butoxycarbonyl-amino-t-1-hydroxycyclopentan-r-1-carboxylate, (+) Methyl c-3-{(1'-acetylamino-3'-ethyl-2'-hydroxy)pentyl}-t-4-{(tert-butoxycarbonyl-amino-tert-butoxycarbonylimino)methyl}amino-t-1-hydroxycyclopentan-r-1-carboxylate, (+) c-3-{(1'-Acetylamino-3'-ethyl-2'-hydroxy)pentyl}-t-4-{aminoiminomethyl}-amino-t-1-hydroxycyclopentan-r-1-carboxylic acid, (+) c-3-{(1'-Acetylamino-3'-ethyl-2'-hydroxy)pentyl}-t-4-{aminoiminomethyl}-amino-t-1-hydroxycyclopentan-r-1-carboxylic acid, (+) 2-{3β-(1'-Acetylamino-3'-ethyl)-2'-pentenyl-4α-tert-butoxycarbonylamino-1-cyclopentylidene}-1,3-dithiane, (+) Methyl 3β-(1'-Acetylamino-3'-ethyl)-2'-pentenyl-4α-(tert-butoxycarbonyl)amino-cyclopentan-1-carboxylate, (+)

Methyl 3β-(1'-Acetylamino-3'-ethyl)-2'-pentenyl-4α-aminocyclopentan-1-carboxylate, (+) 3β-(1'-Acetylamino-3'-ethyl)-2'-pentenyl-4α-aminocyclopentan-1-carboxylic acid, (+) Methyl 3β-(1'-acetylamino-3'-ethyl)pentyl-4α-aminocyclopentan-1-carboxylate, (+) 3β-(1'-Acetylamino-3'-ethyl)pentyl-4α-aminocyclopentan-1-carboxylate, (+) Methyl 3β-(1'-Acetylamino-3'-ethyl)-2'-pentenyl-4α-aminocyclopentan-1-carboxylate, (+) Methyl 3β-(1'-acetylamino-3'-ethyl)pentyl-4α-aminocyclopentan-1-carboxylate, (+) 3β-(1'-Acetylamino-3'-ethyl)pentyl-4α-aminocyclopentan-1-carboxylic acid, (+) 2-{3β-(1'-Acetylamino)-2'-pentenyl-4α-tert-butoxycarbonylamino-1-cyclopent-ylidene}-1,3-dithiane, (+) Methyl 3β-(1'-acetylamino)-2'-pentenyl-4α-tert-butoxycarbonylaminocyclopentan-1-carboxylate, (+) Methyl 3β-(1'-acetylamino)pentyl-4α-tert-butoxyarbonylaminocyclopentan-1-carboxylate, (+) Methyl 3β-(1'-acetylamino)pentyl-4α-aminocyclopentan-1-carboxylate, (+) 3β-(1'-Acetylamino)pentyl-4α-aminocyclopentan-1-carboxylic acid, (+) Methyl cyclopent-3-ene-1-carboxylate, and (+) Ethyl cyclopent-3-ene-1-carboxylate, (+) Methyl t-3-(1'-acetylaminopentyl)-t-4-hydroxycyclopentan-r-1-carboxylate, (+) Methyl t-3-(1'-acetylaminopentyl)-t-4-hydroxycyclopentan-r-1-carboxylate, (+) Methyl t-3-(1-acetylamino-2-ethyl)butyl-t-4-hydroxycyclopentan-r-1-carboxylate, (+) Methyl t-3-[(1'-acetylamino-2'-ethyl)butyl]-t-4-hydroxycyclopentan-r-1-carboxylate, (+) Methyl t-3-(1'-acetylamino-2'-propyl)pentyl-t-4-hydroxycyclopentan-r-1-carboxylate, (+) Ethyl t-3-(1'-acetylamino-2'-cyclohexyl)ethyl-t-4-hydroxycyclopentan-r-1-carboxylate, (+) Ethyl t-3-(1'-acetylamino-2'-ethyl)hexyl-t-4-hydroxycyclopentan-r-1-carboxylate, (+) Ethyl t-3-(1'-acetylamino-2'-methyl)propyl-t-4-hydroxycyclopentan-r-1-carboxylate, (+) Ethyl t-3-(1'-acetylamino-1'-cyclohexyl)methyl-t-4-hydroxycyclopentan-r-1-carboxylate, (+) t-3-(1'-Acetylaminopentyl)-t-4-hydroxycyclopentan-r-1-carboxylic acid, (+) t-3-(1'-Acetylaminopentyl)-t-4-hydroxycyclopentan-r-1-carboxylic acid, (+) t-3-(1'-Acetylaminopentyl)-t-4-hydroxycyclopentan-r-1-carboxylic acid, (+) t-3-(1'-Acetylamino-2'-ethyl)butyl-t-4-hydroxycyclopentan-r-1-carboxylic acid, (+) t-3-(1'-Acetylamino-2'-ethyl)butyl-t-4-hydroxycyclopentan-r-1-carboxylic acid, (+) t-3-(1'-Acetylamino-2'-propyl)pentyl-t-4-hydroxycyclopentan-r-1-carboxylic acid, (+) t-3-(1'-Acetylamino-2'-cyclohexyl)ethyl-t-4-hydroxycyclopentan-r-1-carboxylic acid, (+) t-3-(1'-Acetylamino-2'-ethyl)hexyl-t-4-hydroxycyclopentan-r-1-carboxylic acid, (+) t-3-(1'-Acetylamino-2'-methyl)propyl-t-4-hydroxycyclopentan-r-1-carboxylic acid, (+) t-3-(1'-Acetylamino-1'-cyclohexyl)methyl-t-4-hydroxycyclopentan-r-1-carboxylic acid, (+) Methyl t-3-(1'-acetylaminopentyl)-t-4-methanesulfonyloxycyclopentan-r-1-carboxylate, (+) Methyl t-3-(1'-acetylaminopentyl)-t-4-methanesulfonyloxycyclopentan-r-1-carboxylate, (+) Methyl-t-3-(1'-Acetylamino-2'-ethyl)butyl-t-4-methanesulfonyloxycyclopentan-r-1-carboxylate, (+) Methyl t-3-(1'-acetylamino-2'-propyl)pentyl-t-4-methanesulfonyloxycyclopentan-r-1-carboxylate, (+) Methyl t-3-(1'-acetylaminopentyl)-c-4-azidocyclopentan-r-1-carboxylate, (+) Methyl-t-3-(1'-acetylaminopentyl)-c-4-azidocyclopentan-r-1-carboxylate, (+) Methyl t-3-[(1'-acetylamino-2'-ethyl)butyl]-c-4-azidocyclopentan-r-1-carboxylate, (+) Methyl t-3-(1'-acetylamino-2'-propyl)pentyl-c-4-azidocyclopentan-r-1-carboxylate, (+) Methyl t-3-(1'-acetylaminopentyl)-c-4-aminocyclopentan-r-1-carboxylate, (+) Methyl t-3-(1'-acetylaminopentyl)-c-4-aminocyclopentan-r-1-carboxylate, (+) Methy t-3-[(1'-acetylamino-2'-ethyl)butyl]-c-4-aminocyclopentan-r-1-carboxylate, (+) Methyl t-3-(1'-acetylamino-2'-propyl)pentyl-c-4-aminocyclopentan-r-1-carboxylate, (+) t-3-(1'-Acetylaminopentyl)-c-4-aminocyclopentan-r-1-carboxylic acid, (+) t-3-(1'-Acetylaminopentyl)-c-4-aminocyclopentan-r-1-carboxylic acid, (+) t-3-[(1'-Acetylamino-2'-ethyl)butyl]-c-4-aminocyclopentan-r-1-carboxylic acid, (+) t-3-(1'-Acetylamino-2'-propyl)pentyl-c-4-aminocyclopentan-r-1-carboxylic acid, (+) Methyl c-3-(1'-acetylaminopentyl)-c-4-hydroxycyclopentan-r-1-carboxylate, (+) c-3-(1'-Acetylaminopentyl)-c-4-hydroxycyclopentan-r-1-carboxylic acid, (+) Methyl c-3-(1'-acetylaminopentyl)-c-4-methanesulfonyloxycyclopentan-r-1-carboxylate, (+) Methyl-c-3-(1'-acetylaminopentyl)-t-4-azidocyclopentan-r-1-carboxylate, (+) Methyl c-3-(1'-acetylaminopentyl)-t-4-aminocyclopentan-r-1-carboxylate, (+) c-3-(1'-Acetylaminopentyl)-t-4-aminocyclopentan-r-1-carboxylic acid, (+) Methyl t-3-(1'-acetylaminopentyl)-c-4-{(tert-butoxycarbonylamino-tert-butoxycarbonylimino)methyl}aminocyclopentan-r-1-carboxylate, (+) Methyl t-4-(1'-acetylaminopentyl)-c-4-{(tert-butoxycarbonylamino-tert-butoxy carbonylimino)methyl}aminocyclopentan-r-1-carboxylate, (+) Methyl t-3-{(1'-acetylamino-2'-ethyl)butyl}-c-4-{(tert-butoxycarbonylamino-tert-butoxy carbonylimino)methyl}aminocyclopentan-r-1-carboxylate, (+) Methyl t-3-(1'-acetylamino-2'-propyl)pentyl-c-4-{(tert-butoxycarbonylamino-tert-butoxycarbonylimino)methyl}aminocyclopentan-r-1-carboxylate, (+) Methyl t-3-(1'-acetylaminopentyl)-c-4-{(aminoimino)methyl}aminocyclopentan-r-1-carboxylate, (+) Methyl t-3-(1'-acetylaminopentyl)-c-4-{(aminoimino)methyl}aminocyclopentan-r-1-carboxylate, (+) Methyl t-3-{(1'-acetylamino-2'-ethyl)butyl}-c-4-{(aminoimino)methyl}amino- cyclopentan-r-1-carboxylate, (+) t-3-(1'-Acetylamino-2'-propyl)pentyl-c-4-{(tert-butoxycarbonylamino-tert-butoxycarbonylimino)methyl}aminocyclopentan-r-1-carboxylic acid, (+) t-3-(1'-Acetylaminopentyl)-c-4-{(aminoimino)methyl}aminocyclopentan-r-1-carboxylic acid, (+) t-3-(1'-Acetylaminopentyl)-c-4-{(aminoimino)methyl}aminocyclopentan-r-1-carboxylic acid, (+) t-3-{(1'-Acetylamino-2'-ethyl)butyl}-c-4-{(aminoimino)methyl}aminocyclopentan-r-1-carboxylic acid, (+) t-3-(1'-Acetylamino-2'-propyl)pentyl-c-4-{(aminoimino)methyl}aminocyclopentan-r-1-carboxylic acid, (+) Methyl c-3-(1'-acetylaminopentyl)-t-4-{(tert-butoxycarbonylamino-tert-butoxy carbonylimino)methyl}aminocyclopentan-r-1-carboxylate, (+) Methyl c-3-(1'-Acetylaminopentyl)-t-4-{(aminoimino)methyl}aminocyclopentan-r-1-carboxylate, (+) c-3-(1-Acetylaminopentyl)-t-4-{(aminoimino)methyl}aminocyclopentan-r-1-carboxylic acid, (1S,4R)-(−)-4-Aminocyclopent-2-en-1-carboxylic acid, (1R,4S)-(+)-4-Aminocyclopent-2-en-1-carboxylic acid, (+)-cis-4-

Aminocyclopent-2-en-1-carboxylic acid, (1S,4R)-(−)-Methyl-4-aminocyclopent-2-en-1-carboxylate, (1S,4R)-(−)-Ethyl-4-aminocyclopent-2-en-1-carboxylate, (1R,4S)-(+)-Ethyl-4-aminocyclopent-2-en-1-carboxylate, (+)-cis-Methyl-4-aminocyclopent-2-en-1-carboxylate, (+)-cis-Ethyl-4-aminocyclopent-2-en-1-carboxylate, (1S,4R)-(−)-Methyl-4-tert-butoxycarbonylaminocyclopent-2-en-1-carboxylate, (1S,4R)-(−)-Ethyl-4-tert-butoxycarbonylaminocyclopent-2-en-1-carboxylate, (1R,4S)-(+)-Ethyl-4-tert-butoxycarbonylaminocyclopent-2-en-1-carboxylate, (+)-cis-Methyl-4-tert-butoxycarbonylaminocyclopent-2-en-1-carboxylate, (+)-cis-Ethyl-4-tert-butoxycarbonylaminocyclopent-2-en-1-carboxylate, (1S,2S,3R,4R,1'S)-(−)-Methy 3-(1'-acetyamino-2'-ethyl)butyl-4-tert-butoxycarbonyl-amino-2-hydroxycyclopentan-1-carboxylate, (1S,2S,3R,4R,1'S)-(−)-Methyl 3-(1'-acetylamino-2'-propyl)pentyl-4-tert-butoxycarbonyl-amino-2-hydroxycyclopentan-1-carboxylate, (1S,2S,3R,4R,1'S)-(−)-Ethyl 3-(1'-acetylamino-2'-ethyl)butyl-4-tert-butoxycarbonyl-amino-2-hydroxycyclopentan-1-carboxylate, (1S,2S,3R,4R,1'S)-(−)-Methyl 3-(1'-acetylamino-2'-propyl)pentyl-4-tert-butoxycarbonyl-amino-2-hydroxycyclopentan-1-carboxylate, (1R,2R,3S,4S,1'R)-(+)-Ethyl 3-(1'-acetylamino-2'-ethyl)butyl-4-tert-butoxycarbonyl-amino-2-hydroxycyclopentan-1-carboxylate, (+)-Methyl t-3-(1'-acetylamino-2'-ethyl)butyl-c-4-tert-butoxycarbonylamino-t-2-hydroxycyclopentan-r-1-carboxylate, (+)-Methyl t-3-(1'-acetylamino-2'-propyl)pentyl-c-4-tert-butoxycarbonylamino-t-2-hydroxycyclopentan-r-1-carboxylate, (+)-Methyl t-3-(1'-acetylamino-3'-ethyl)pentyl-c-4-tert-butoxycarbonylamino-t-2-acetyloxycyclopentan-r-1-carboxylate, (+)-Methyl t-3-(1'-acetylamino-n-butyl)-c-4-tert-butoxycarbonylamino-t-2-acetyloxy-cyclopentan-r-1-carboxylate, (+)-Ethyl t-3-(1'-acetylamino-2'-ethyl)butyl-c-4-tert-butoxycarbonylamino-t-2-hydroxycyclopentan-r-1-carboxylate, (+)-Ethyl t-3-(1'-acetylamino-2'-methyl)butyl-c-4-tert-butoxycarbonylamino-t-2-hydroxycyclopentan-r-1-carboxylate, (+)-Ethyl t-3-(1'-acetylamino-2'-methyl)propyl-c-4-tert-butoxycarbonylamino-t-2-hydroxycyclopentan-r-1-carboxylate, (1S,2S,3R,4R,1'S)-(−)-Methyl 3-(1'-acetylamino-2'-ethyl)butyl-4-amino-2-hydroxy-cyclopentan-1-carboxylate, (1S,2S,3R,4R,1'S)-(−)-Methyl 3-(1'-acetylamino-2'-propyl)pentyl-4-amino-2-hydroxycyclopentan-1-carboxylate, (1S,2S,3R,4R,1'S)-(−)-Ethyl 3-(1'-acetylamino-2'-ethyl)butyl-4-amino-2-hydroxycyclo-pentan-1-carboxylate, 1R,2R,3S,4S,1'R)-(+)-Ethyl 3-(1'-acetylamino-2'-ethyl)butyl-4-amino-2-hydroxy-cyclopentan-1-carboxylate, (+)-Methyl t-3-(1'-acetylamino-2'-ethyl)butyl-c-4-amino-t-2-hydroxycyclopentan-r-1-carboxylate, (+)-Methyl t-3-(1'-acetylamino-2'-propyl)pentyl-c-4-amino-t-2-hydroxycyclopentan-r-1-carboxylate, (+)-Methyl t-3-(1'-acetylamino-3'-ethyl)pentyl-c-4-amino-t-2-acetyloxycyclopentan-r-1-carboxylate, (+)-Methyl t-3-(1'-acetylamino-n-butyl)-c-4-amino-t-2-acetyloxycyclopentan-r-1-carboxylate, (+)-Ethyl t-3-(1'-acetylamino-2'-ethyl)butyl-c-4-amino-t-2-hydroxycyclopentan-r-1-carboxylate, (+)-Ethyl t-3-(1'-acetylamino-2'-methyl)butyl-c-4-amino-t-2-hydroxycyclopentan-r-1-carboxylate, (+)-Ethyl t-3 -(1'-acetylamino-2'-methyl)propyl-c-4-amino-t-2-hydroxycyclopentan-r-1-carboxylate, (1S,2S,3R,4R,1'S)-(−)-3-(1'-Acetylamino-2'-ethyl)butyl-4-amino-2-hydroxycyclopentan-1-carboxylic acid, (1R,2R,3S,4S,1'R)-(+)-3-(1'-Acetylamino-2'-ethyl)butyl-4-amino-2-hydroxy-cyclopentan-1-carboxylic acid, (+)-t-3-(1'-Acetylamino-2'-ethyl)butyl-c-4-amino-t-2-hydroxycyclopentan-r-1-carboxylic acid, (+)-t-3-(1'-Acetylamino-2'-propyl)pentyl-c-4-amino-t-2-hydroxycyclopentan-r-1-carboxylic acid, (+)-t-3-(1'-Acetylamino-3'-ethyl)pentyl-c-4-amino-t-2-hydroxycyclopentan-r-1-carboxylic acid, (+)-t-3-(1'-Acetylamino-n-butyl)-c-4-amino-t-2-hydroxycyclopentan-r-1-carboxylic acid, (+)-t-3-(1'-Acetylamino-2'-methyl)butyl-c-4-amino-t-2-hydroxycyclopentan-r-1-carboxylic acid, (+)-t-3-(1'-Acetylamino-2'-methyl)propyl-c-4-amino-t-2-hydroxycyclopentan-r-1-carboxylic acid, (1S,2S,3R,4R,1'S)-(−)-Ethyl 3-(1'-acetylamino-2'-ethyl)butyl-4-{(tert-butoxycarbo-nyl-amino-tert-butoxycarbonylimino)methyl}amino-2-hydroxycyclopentan-1-carboxylate, (+)-Methyl t-3-(1'-acetylamino-2'-ethyl)butyl-c-4-{(tert-butoxycarbonylamino-tert-butoxycarbonylimino)methyl}amino-t-2-hydroxycyclopentan-r-1-carboxylate, (+)-Methyl t-3-(1'-acetylamino-3'-ethyl)pentyl-c-4-{(tert-butoxycarbonylamino-tert-butoxycarbonylimino)methyl}amino-t-2-acetyloxycyclopentan-r-1-carboxylate, (+)-Methyl t-3-(1'-acetylamino-n-butyl)-c-4-{(tert-butoxycarbonylamino-tert-butoxycarbonylimino)methyl}amino-t-2-acetyloxycyclopentan-r-1-carboxylate, (1S,2S,3R,4R,1'S)-(−)-Ethyl 3-(1'-acetylamino-2'-ethyl)butyl-4-{(N-tert-butoxycarbonyl-N-methylamino-N'-tert-butoxycarbonylimino)methyl}amino-2-hydroxycyclopentan-1-carboxylate, (1S,2S,3R,4R,1'S)-(−)-Ethyl 3-(1'-acetylamino-2'-ethyl)butyl-4-{(amino-imino)methyl}-amino-2-hydroxycyclopentan-1-carboxylate, (+)-Methyl t-3-(1'-acetylamino-2'-ethyl)butyl-c-4-{(amino-imino)methyl}amino-t-2-hydroxycyclopentan-r-1-carboxylate, (+)-Methyl t-3-(1'-acetylamino-3'-ethyl)pentyl-c-4-{(amino-imino)methyl}amino-t-2-acetyloxycyclopentan-r-1-carboxylate, (+)-Methyl t-3-(1'-acetylamino-n-butyl)-c-4-{(amino-imino)methyl}amino-t-2-acetyloxycyclopentan-r-1-carboxylate, (1S,2S,3R,4R,1'S)-(−)-Ethyl-3-(1'-acetylamino-2'-ethyl)butyl-4-{(N-methylamino-imino)methyl}amino-2-hydroxycyclopentan-1-carboxylate, (1S,2S,3R,4R,1'S)-(−)-3-(1'-Acetylamino-2'-ethyl)butyl-4-{(aminoimino) methyl}amino-2-hydroxycyclopentan-1-carboxylic acid, (+)-t-3-(1'-Acetylamino-2'-ethyl)butyl-c-4-{(amino-imino)methyl}amino-t-2-hydroxycyclopentan-r-1-carboxylic acid, (+)-t-3-(1'-Acetylamino-3'-ethyl)pentyl-c-4-{(amino-imino)methyl}amino-t-2-hydroxycyclopentan-r-1-carboxylic acid, (+)-t-3-(1'-Acetylamino-n-butyl)-c-4-{(amino-imino)methyl}amino-t-2-hydroxycyclopentan-r-1-carboxylic acid, (1S,2S,3R,4R,1'S)-(−)-3-(1'-Acetylamino-2'-ethyl)butyl-4-{(N-methylamino-imino)methyl}amino-2-hydroxycyclopentan-1-carboxylic acid, (1S,2S,3R,4R,1'S)-(−)-3-(1'-Acetylamino-2'-propyl)pentyl-4-{(amino-imino)methyl}amino-2-hydroxycyclopentan-1-carboxylic acid, (1S,2S,3R,4R,1'S)-(−)-Methyl 3-(1'-acetylamino-2'-ethyl)butyl-4-tert-butoxycarbonyl-amino-2-(N-imidazolyl-thiocarbonyloxy)cyclopentan-1-carboxylate, (1S,2S,3R,4R,1'S)-(−)-Methyl 3-(1'-acetylamino-2'-propyl)pentyl-4-tert-butoxycarbonylamino-2-(N-imidazolyl-thiocarbonyloxy)cyclopentan-1-carboxylate, (1S,2S,3R,4R,1'S)-(−)-Ethyl 3-(1'-acetylamino-2'-ethyl)butyl-4-tert-butoxycarbonyl-amino-2-(N-imidazolyl-thiocarbonyloxy)cyclopentan-1-carboxylate, (1S,2S,3R,4R,1'S)-(−)-Methyl 3-(1'-acetylamino-2'-propyl)pentyl-4-tert-butoxycarbonyl-amino-2-(N-imidazolyl-thiocarbonyloxy)cyclopentan-1-carboxylate, (+)-Methyl t-3-(1'-acetylamino-2'-ethyl)butyl-c-4-tert-butoxycarbonylamino-t-2-(N-imidazolyl-thiocarbonyloxy)cyclopentan-r-1-carboxylate, (1R,3R,4R,1'S)-(−)-Methyl 3-(1'-acetylamino-2'-ethyl)butyl-4-tert-butoxycarbonyl-aminocyclopentan-1-carboxylate, (1R,3R,4R,1'S)-(−)-Methyl 3-(1'-acetylamino-2'-propyl)pentyl-4-tert-butoxycarbonyl-aminocyclopentan-1-carboxylate, (1R,3R,4R,1'S)-(−)-Ethyl 3-(1'-acetylamino-2'-ethyl)butyl-4-tert-butoxycarbonyl-amino-cyclopentan-1-carboxylate, (1R,3R,4R,1'S)-(−)-Methyl 3-(1'-acetylamino-2'-propyl)pentyl-4-tert-butoxycarbonyl-aminocyclopentan-1-carboxylate, (+)-Methyl t-3-(1'-acetylamino-2'-ethyl)butyl-c-4-tert-butoxycarbonylaminocyclo-pentan-1-carboxylate, (1R,3R,4R,1'S)-(−)-Methyl 3-(1'-acetylamino-2'-ethyl)butyl-4-aminocyclopentan-1-carboxylate, (1R,3R,4R,1'S)-(−)-Methyl 3-(1'-acetylamino-2'-propyl)pentyl-4-aminocyclopentan-1-carboxylate, (1R,3R,4R,1'S)-(−)-Ethyl 3-(1'-acetylamino-2'-ethyl)butyl-4-aminocyclopentan-1-carboxylate, (1R,3R,4R,1'S)-(−)-Ethyl-3-(1'-acetylamino-2'-propyl)pentyl-4-aminocyclopentan-1-carboxylate, (+)-Methyl t-3-(1'-acetylamino-2'-ethyl)butyl-c-4-aminocyclopentan-1-carboxylate, (1R,3R,4R,1'S)-(−)-3-(1'-Acetylamino-2'-ethyl)butyl-4-aminocyclopentan-1-carboxylic acid, (+)-t-3-(1'-Acetylamino-2'-ethyl)butyl-c-4-aminocyclopentan-1-carboxylic acid, (1R,3R,4R,1'S)-(−)-Ethyl 3-(1'-acetylamino-2'-ethyl)butyl-4-{(tert-butoxycarbonyl-amino-tert-butoxycarbonylimino)methyl}aminocyclopentan-1-carboxylate, (1R,3R,4R,1'S)-(−)-Ethyl 3-(1'-acetylamino-2'-propyl)pentyl-4-{(tert-butoxycarbonyl-amino-tert-butoxycarbonylimino)methyl}aminocyclopentan-1-carboxylate, (+)-Methyl t-3-(1'-acetylamino-2'-ethyl)butyl-c-4-{(tert-butoxycarbonylamino-tert-butoxycarbonylimino)methyl}aminocyclopentan-r-1-carboxylate, (1R,3R,4R,1'S)-(−)-Ethyl 3-(1'-acetylamino-2'-ethyl)butyl-4-{(N-tert-butoxycarbonyl-N-methylamino-N'-tert-butoxycarbonylimino)methyl}aminocyclopentan-1-carboxylate, (1R,3R,4R,1'S)-(−)-Ethyl 3-(1'-acetylamino-2'-ethyl)butyl-4-{(amino-imino)methyl}-aminocyclopentan-1-carboxylate, (1R,3R,4R,1'S)-(−)-Ethyl 3-(1'-acetylamino-2'-propyl)pentyl-4-{(amino-imino)-methyl}aminocyclopentan-1-carboxylate, (+)-Methyl t-3-(1'-acetylamino-2'-ethyl)butyl-c-4-{(amino-imino)methyl}-aminocyclo-pentan-r-1-carboxylate, (1R,3R,4R,1'S)-(−)-Ethyl-3-(1'-acetylamino-2'-ethyl)butyl-4-{(N-methylamino-imino)methyl}aminocyclopentan-1-carboxylate, (1R,3R,4R,1'S)-(−)-3-(1'-Acetylamino-}2'-ethyl)butyl-4-(aminoimino)methyl-aminocyclopentan-1-carboxylic acid, (1R,3R,4R,1'S)-(−)-3-(1'-Acetylamino-2'-propyl)pentyl-4-{(amino-imino)methyl}aminocyclopentan-1-carboxylic acid, (+)-t-3-(1'-Acetylamino-2'-ethyl)butyl-c-4-{(amino-imino)methyl}-aminocyclopentan-r-1-carboxylic acid, (1R,3R,4R,1'S)-(−)-3 -(1'-Acetylamino-2'-ethyl)butyl-4-{(N-methylamino-imino)methyl}aminoclopentan-1-carboxylic acid, (1S,2S,3R,4R,1'S)-(−)-Methyl 3-(1'-acetylamino-2'-ethyl)butyl-4-tert-butoxy-carbonylamino-2-methanesulfonyloxycyclopentan-1-carboxylate, (3R,4R,1'S)-(−)-Methyl-3-(1'-acetylamino-2'-ethyl)butyl-4-tert-butoxycarbonyl-amino-cyclopent-1-en-1-carboxylate, (3R,4R,1'S)-(−)-Methyl 3-(1'-acetylamino-2'-ethyl)butyl-4-aminocyclopent-1-en-1-carboxylate hydrochloride, (3R,4R,1'S)-(−) 3-(1'-Acetylamino-2'-ethyl)butyl-4-aminocyclopent-1-en-1-carboxylic acid, (3R,4R,1'S)-(−)-Methyl 3-(1'-acetylamino-2'-ethyl)butyl-4-{(tert-butoxycarbonyl-amino-tert-butoxycarbonylimino)methyl}aminocyclopent-1-en-1-carboxylate, (3R,4R,1'S)-(−)-3-(1'-Acetylamino-2'-ethyl)butyl-4-{(tert-butoxycarbonylamino-tert-butoxycarbonylimino)methyl}aminocyclopent-1-en-1-carboxylic acid, (3R,4R,1's)-(−)-3-(1'-Acetylamino-2'-ethyl)butyl-4-{(amino-imino)methyl}amino-cyclopent-1-en-1-carboxylic acid; and pharmaceutically acceptable salts thereof.

8. The compound of claim 1 being selected from the group consisting of (+) t-3-(1'-Acetylamino-2'-ethyl)butyl-t-4-hydroxycyclopentan-r-1-carboxylic acid (+) t-3-[(1'-Acetylamino-2'-ethyl)butyl]-c-4-aminocyclopentan-r-1-carboxylic acid (1S,2S,3R,4R,1'S)-(−)-3-(1'-Acetylamino-2'-ethyl)butyl-4-amino-2-hydroxycyclo pentan-1-carboxylic acid, (+)-t-3-(1'-Acetylamino-2'-ethyl)butyl-c-4-amino-t-2-hydroxycyclopentan-r-1-carboxylic acid, (+)-t-3-(1'-Acetylamino-2'-propyl)pentyl-c-4-amino-t-2-hydroxycyclopentan-r-1-carboxylic acid, (+)-t-3-(1'-Acetylamino-n-butyl)-c-4-amino-t-2-hydroxycyclopentan-r-1-carboxylic acid, (+)-t-3-(1'-Acetylamino-2'-methyl)butyl-c-4-amino-t-2-hydroxycyclopentan-r-1-carboxylic acid, (1S,2S,3R,4R,1'S)-(−)-3-(1'-Acetylamino-2'-ethyl)butyl-4-{aminoimino)methyl}amino-2-hydroxycyclopentan-1-carboxylic acid, (+)-t-3-(1'-Acetylamino-2'-ethyl)butyl-c-4-{amino-imino)methyl}amino-t-2-hydroxycyclopentan-r-1-carboxylic acid, (+)-t-3-(1'-Acetylamino-3'-ethyl)pentyl-c-4-{(amino-imino)methyl}amino-t-2-hydroxycyclopentan-r-1-carboxylic acid, (+)-t-3-(1'-Acetylamino-n-butyl)-c-4-[(amino-imino)methyl]amino-t-2-hydroxycyclopentan-r-1-carboxylic acid, (1S,2S,3R,4,R1'S)-(−)-3-(1'-Acetylamino-2'-ethyl)butyl-4-{(N-methylamino-imino)methyl}amino-2-hydroxycyclopentan-1-carboxylic acid, (1S,2S,3R,4R,1'S)-(−)-3-(1'-Acetylamino-2'-propyl)pentyl-4-{(amino-imino)methyl}amino-2-hydroxycyclopentan-1-carboxylic acid, (1R,3R,4R,1'S)-(−)-3-(1'-Acetylamino-2'-ethyl)butyl-4-aminocyclopentan-1-carboxylic acid, (+)-t-3-(1'-Acetylamino-2'-ethyl)butyl-c-4-aminocyclopentan-1-carboxylic acid, (1R,3R,4R,1'S)-(−)-3-(1'-Acetylamino-2'-ethyl)butyl-4-(aminoimino)methyl-aminocyclopentan-1-carboxylic acid, (1R,3R,4R,1'S)-(−)-3-(1'-Acetylamino-2'-propyl)pentyl-4-{(amino-imino)methyl}aminocyclopentan-1-carboxylic acid, (+)-t-3-(1'-Acetylamino-2'-ethyl)butyl-c-4-{(amino-imino)methyl}-aminocyclopentan-r-1-carboxylic acid, (1R,3R,4R,1'S)-(−)-3-(1'-Acetylamino-2'-ethyl)butyl-4-{(N-methylamino-imino)methyl}aminocyclopentan-1-carboxylic acid, (3R,4R,1'S)-(−)-3-(1'-Acetylamino-2'-ethyl)butyl-4-{(amino-imino)methyl}amino-cyclopent-1-en-1-carboxylic acid; and pharmaceutically acceptable salts thereof.

9. The compound of claim 7 being (1S,2S,3R,4R,1'S)-(−)-Methyl-3-(1'-acetylamino-2'-ethyl)butyl-4-amino-2-hydroxy-cyclopentan-1-carboxylate; or a pharmaceutically acceptable salt thereof.

10. The compound of claim 7 being (1S,2S,3R,4R,1'S)-(−)-Methyl-3-(1'-acetylamino-2'-propyl)pentyl-4-amino-2-hydroxy-cyclopentan-1-carboxylate; or a pharmaceutically acceptable salt thereof.

11. The compound of claim 7 being (1S,2S,3R,4R,1'S)-(−)-Ethyl-3-(1'-acetylamino-2'-ethyl)butyl-4-amino-2-hydroxy-cyclopentan-1-carboxylate; or a pharmaceutically acceptable salt thereof.

12. The compound of claim 9 being (1R,2R,3S,4S,1'R)-(+)-Ethyl-3-(1'-acetylamino-2'-ethyl)butyl-4-amino-2-hydroxy-cyclopentan-1-carboxylate; or a pharmaceutically acceptable salt thereof.

13. The compound of claim 7 being (1S,2S,3R,4R,1'S)-(−)-3-(1'-Acetylamino-2'-ethyl)butyl-4-amino-2-hydroxy-cyclopentan-1-carboxylic acid; or a pharmaceutically acceptable salt thereof.

14. The compound of claim 7 being (1R,2R,3S,4S,1'R)-(+)-3-(1'-Acetylamino-2'-ethyl)butyl-4-amino-2-hydroxy-cyclopentan-1-carboxylic acid; or a pharmaceutically acceptable salt thereof.

15. The compound of claim 7 being (1S,2S,3R,4R,1'S)-(−)-Ethyl-3-(1'-acetylamino-2'-ethyl)butyl-4-[(aminoimino)-methyl]amino-2-hydroxy-cyclopentan-1-carboxylate; or a pharmaceutically acceptable salt thereof.

16. The compound of claim 7 being (1S,2S,3R,4R,1'S)-(−)-Ethyl-3-(1'-acetylamino-2'-ethyl)butyl-4-[(N-methylamino-imino)methyl]amino-2-hydroxycyclopentan-1-carboxylate; or a pharmaceutically acceptable salt thereof.

17. The compound of claim 7 being (3R,4R,1'S)-(−)-Methyl-3-(1'-acetylamino-2'-ethyl)butyl-4-aminocyclopent-1-en-1-carboxylate; or a pharmaceutically acceptable salt thereof.

18. The compound of claim 7 being (3R,4R,1'S)-(−)-3-(1'-Acetylamino-2'-ethyl)butyl-4-aminocyclopent-1-en-1-carboxylic acid; or a pharmaceutically acceptable salt thereof.

19. The compound of claim 7 being (3R,4R,1'S)-(−)-3-(1'-Acetylamino-2'-ethyl)butyl-4-[(aminoimino)methyl]amino-cyclopent-1-en-1-carboxylic acid; or a pharmaceutically acceptable salt thereof.

20. The compound of claim 7 being (1S,2S,3R,4R,1'S)-(−)-3-(1'-Acetylamino-2'-ethyl)butyl-4-[(aminoimino)methyl]-amino-2-hydroxycyclopentan-1-carboxylic acid; or a pharmaceutically acceptable salt thereof.

21. The compound of claim 7 being (1S,2S,3R,4R,1'S)-(−)-3-(1'-Acetylamino-2'-ethyl)butyl-4-[(N-methylamino-imino)methyl]amino-2-hydroxycyclopentan-1-carboxylic acid; or a pharmaceutically acceptable salt thereof.

22. The compound of claim 7 being (1S,2S,3R,4R,1'S)-(−)-3-(1'-Acetylamino-2'-propyl)pentyl-4-[(aminoimino)-methyl]amino-2-hydroxycyclopentan-1-carboxylic acid; or a pharmaceutically acceptable salt thereof.

23. The compound of claim 7 being (1R,3R,4R,1'S)-(−)-Methyl-3-(1'-acetylamino-2'-ethyl)butyl-4-aminocyclopentan-1-carboxylate; or a pharmaceutically acceptable salt thereof.

24. The compound of claim 7 being (1R,3R,4R,1'S)-(−)-Ethyl-3-(1'-acetylamino-2'-ethyl)butyl-4-aminocyclopentan-1-carboxylate; or a pharmaceutically acceptable salt thereof.

25. The compound of claim 7 being (1R,3R,4R,1'S)-(−)-Ethyl-3-(1'-acetylamino-2'-propyl)pentyl-4-aminocyclopentan-1-carboxylate; or a pharmaceutically acceptable salt thereof.

26. The compound of claim 7 being (1R,3R,4R,1'S)-(−)-3-(1'-Acetylamino-2'-ethyl)butyl-4-aminocyclopentan-1-carboxylic acid; or a pharmaceutically acceptable salt thereof.

27. The compound of claim 7 being (1R,3R,4R,1'S)-(−)-Ethyl-3-(1'-acetylamino-2'-ethyl)butyl-4-[(aminoimino)-methyl]aminocyclopentan-1-carboxylate; or a pharmaceutically acceptable salt thereof.

28. The compound of claim 7 being (1R,3R,4R,1'S)-(−)-Ethyl-3-(1'-acetylamino-2'-ethyl)butyl-4-[(N-methylamino-imino)methyl]aminocyclopentan-1-carboxylate; or a pharmaceutically acceptable salt thereof.

29. compound of claim 7 being (1R,3R,4R,1'S)-(−)-3-(1'-Acetylamino-2'-ethyl)butyl-4-[(aminoimino)methyl]-aminocyclopentan-1-carboxylic acid; or a pharmaceutically acceptable salt thereof.

30. The compound of claim 7 being (1R,3R,4R,1'S)-(−)-3-(1'-Acetylamino-2'-propyl)pentyl-4-[(aminoimino)methyl]-aminocyclopentan-1-carboxylic acid; or a pharmaceutically acceptable salt thereof.

31. The compound of claim 7 being (1R,3R,4R,1'S)-(−)-3-(1'-Acetylamino-2'-ethyl)butyl-4-[(N-methylamino-imino)methyl]aminocyclopentan-1-carboxylic acid; or a pharmaceutically acceptable salt thereof.

32. The compound of claim 7 being (1S,2S,3R,4R,1'S)-(−)-3-(1'-Acetylamino-2'-propyl)pentyl-4-amino-2-hydroxy-cyclopentan-1-carboxylic acid; or a pharmaceutically acceptable salt thereof.

33. The compound of claim 7 being (1R,2R,3S,4S,1'R)-(+)-3-(1'-Acetylamino-2'-propyl)pentyl-4-amino-2-hydroxy-cyclopentan-1-carboxylic acid; or a pharmaceutically acceptable salt thereof.

34. The compound of claim 7 being (1R,2R,3S,4S,1'R)-(+)-3-(1'-Acetylamino-2'-ethyl)butyl-4-[(aminoimino)-methyl]-amino-2-hydroxycyclopentan-1-carboxylic acid; or a pharmaceutically acceptable salt thereof.

35. The compound of claim 7 being (1R,2R,3S,4S,1'R)-(+)-3-(1'-Acetylamino-2'-propyl)pentyl-4-[(aminoimino)-methyl]amino-2-hydroxycyclopentan-1-carboxylic acid; or a pharmaceutically acceptable salt thereof.

36. The compound of claim 7 being (1R,3R,4R,1'S)-(−)-3-(1'-Acetylamino-2'-propyl)pentyl-4-aminocyclo-pentan-1-carboxylic acid; or a pharmaceutically acceptable salt thereof.

37. The compound of claim 7 being (1S,3S,4S,1'R)-(+)-3-(1'-Acetylamino-2'-ethyl)butyl-4-aminocyclopentan-1-carboxylic acid; or a pharmaceutically acceptable salt thereof.

38. The compound of claim 7 being (1S,3S,4S,1'R)-(+)-3-(1'-Acetylamino-2'-ethyl)butyl-4-[(aminoimino)methyl]-aminocyclopentan-1-carboxylic acid; or a pharmaceutically acceptable salt thereof.

39. The compound of claim 7 being (1S,3S,4S,1'R)-(+)-3-(1'-Acetylamino-2'-propyl)pentyl-4-[(aminoimino)methyl]-aminocyclopentan-1-carboxylic acid; or a pharmaceutically acceptable salt thereof.

40. A composition for inhibiting influenza virus nueraminidase, comprising: a pharmaceutically acceptable carrier and an amount effective for inhibiting influenza virus nueraminidase of a compound according to claim 1.

41. A method of treating influenza virus infection, comprising the step of: administering to a patient in need thereof a pharmaceutically acceptable carrier and an amount effective for inhibiting influenza virus nueraminidase of a compound according to claim 1.

* * * * *

UNITED STATES PATENT AND TRADEMARK OFFICE
CERTIFICATE OF CORRECTION

PATENT NO. : 6,562,861 B1
APPLICATION NO. : 09/555131
DATED : May 13, 2003
INVENTOR(S) : Yarlagadda S. Babu et al.

It is certified that error appears in the above-identified patent and that said Letters Patent is hereby corrected as shown below:

Claim 1, page 127, line 12
"$(R_{10})_m$, $C(0)N(0R_{10})R_{10}$, $(CH_2)_nN(R_{10})_m$, $CH(R_{10})$" should be replaced with
--$(R_{10})_m$, $C(0)N(0R_{10})R_{10}$, $(CH_2)_nN(R_{10})_m$, $CH(R_{10})_m$--

Claim 12, page 135, line 9
"The compound of claim 9 being (1R,2R,3S,4S,1'R)-" should be replaced with
-- The compound of claim 7 being (1R,2R,3S,4S,1'R)- --

Signed and Sealed this

Eleventh Day of December, 2007

JON W. DUDAS
*Director of the United States Patent and Trademark Office*